(12) United States Patent
Cheung et al.

(10) Patent No.: US 7,465,807 B2
(45) Date of Patent: Dec. 16, 2008

(54) PROCESS FOR PREPARING BENZIMIDAZOLE THIOPHENES

(75) Inventors: Mui Cheung, Durham, NC (US); Kyle Allen Emmitte, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 295 days.

(21) Appl. No.: 10/575,210

(22) PCT Filed: Oct. 12, 2004

(86) PCT No.: PCT/US2004/033585

§ 371 (c)(1),
(2), (4) Date: Apr. 10, 2006

(87) PCT Pub. No.: WO2005/037827

PCT Pub. Date: Apr. 28, 2005

(65) Prior Publication Data

US 2007/0060576 A1    Mar. 15, 2007

Related U.S. Application Data

(60) Provisional application No. 60/511,991, filed on Oct. 16, 2003.

(51) Int. Cl.
*C07D 409/04* (2006.01)
(52) U.S. Cl. ............................................. 548/304.7
(58) Field of Classification Search ............... 548/304.7
See application file for complete search history.

(56) References Cited

U.S. PATENT DOCUMENTS

| 5,990,146 A | 11/1999 | Boschelli et al. |
| 6,162,804 A | 12/2000 | Bilodeau et al. |

FOREIGN PATENT DOCUMENTS

| ES | 8701172 A1 * | 2/1987 |
| WO | 0012089 A | 3/2000 |
| WO | 01/66525 A | 9/2003 |
| WO | WO-2004/014899 A | 2/2004 |
| WO | 2004/041777 A | 5/2004 |
| WO | 2005/075465 A | 8/2005 |

OTHER PUBLICATIONS

Tarasov et al.; Reaction of 1-(ortho-Aminophenyl)-1,2,3-triazole-5-thiols wiht cyclizing reagents; Russian J of Org Chem; 2004; 40/6; 870-873.
B.D. Palmer et al.,; Structure-Activity Relationships for 1-Phenylbenzimidazoles as selective ATP Site Inhibitors of the Platelet-Derived Growth Factor Receptor; J. Med. Chem.; 1998; 5457-5465; 41.
Corral et al. Reactions of Methyl 3-Hydroxythiophene-2-carboxylate. Part 4. Synthesis of Methyl 2-Azolyl-3-hydroxythiophene-2-carboxylates; J. Het. Chem.; 1987; 1301-1303; 24.

* cited by examiner

*Primary Examiner*—Laura L. Stockton
(74) *Attorney, Agent, or Firm*—Bonnie L. Deppenbrock

(57) ABSTRACT

The present invention provides a process for preparing benzimidazole thiophene compounds.

7 Claims, No Drawings

PROCESS FOR PREPARING BENZIMIDAZOLE THIOPHENES

CROSS REFERENCES TO RELATED APPLICATIONS

This application is a 371 Application of PCT/US2004/033585, filed 12 Oct. 2004, which claims priority to U.S. Application Ser. No. 60/511,991, filed 16 Oct. 2003.

BACKGROUND OF THE INVENTION

The present invention relates to a novel process for preparing compounds of formula (I):

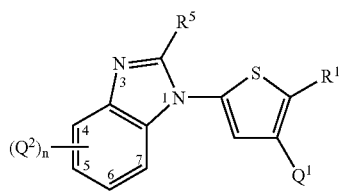

wherein all variables are as defined hereinbelow.

or a pharmaceutically acceptable salt, solvate or physiologically functional derivative thereof.

Compounds of formula (I), pharmaceutical formulations containing the same, therapeutic uses thereof and processes for their preparation are described in PCT Application No. PCT/US03/24272, filed 4 Aug. 2003, to GlaxoSmithKline.

BRIEF SUMMARY OF THE INVENTION

The present invention provides a novel synthetic process for preparing the compounds of formula (I). According to a first aspect of the invention there is provided a process for preparing a compound of formula (I):

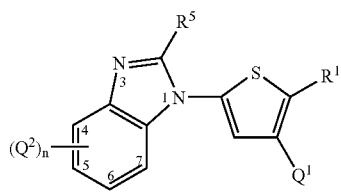

wherein:

$R^1$ is selected from the group consisting of H, alkyl, alkenyl, alkynyl, —C(O)$R^7$, —CO$_2R^7$, —C(O)N$R^7R^8$, —C(O)N($R^7$)O$R^8$, —C(O)N($R^7$)—$R^2$—O$R^8$, —C(O)N($R^7$)-Ph, —C(O)N($R^7$)—$R^2$-Ph, —C(O)N($R^7$)C(O)$R^8$, —C(O)N($R^7$)CO$_2R^8$, —C(O)N($R^7$)C(O)N$R^7R^8$, —C(O)N($R^7$)S(O)$_2R^8$, —$R^2$—O$R^7$, —$R^2$—O—C(O)$R^7$, —C(S)$R^7$, —C(S)N$R^7R^8$, —C(S)N($R^7$)-Ph, —C(S)N($R^7$)—$R^2$-Ph, —$R^2$—S$R^7$, —C(=N$R^7$)N$R^7R^8$, —C(=N$R^7$)N($R^8$)-Ph, —C(=N$R^7$)N($R^8$)—$R^2$-Ph, —$R^2$—N$R^7R^8$, —CN, —O$R^7$, —S(O)$_fR^7$, —S(O)$_2$N$R^7R^8$, —S(O)$_2$N($R^7$)-Ph, —S(O)$_2$N($R^7$)—$R^2$-Ph, —N$R^7R^8$, N($R^7$)-Ph, —N($R^7$)—$R^2$-Ph, —N($R^7$)—SO$_2R^8$ and Het;

Ph is phenyl optionally substituted from 1 to 3 times with a substituent selected from the group consisting of halo, alkyl, —OH, —$R^2$—OH, —O-alkyl, —$R^2$—O-alkyl, —NH$_2$, —N(H)alkyl, —N(alkyl)$_2$, —CN and —N$_3$;

Het is a 5-7 membered heterocycle having 1, 2, 3 or 4 heteroatoms selected from N, O and S, or a 5-6 membered heteroaryl having 1, 2, 3 or 4 heteroatoms selected from N, O and S, each optionally substituted from 1 to 2 times with a substituent selected from the group consisting of halo, alkyl, oxo, —OH, —$R^2$—OH, —O-alkyl, —$R^2$—O-alkyl, —NH$_2$, —N(H)alkyl, —N(alkyl)$_2$, —CN and —N$_3$;

$Q^1$ is a group of formula: —($R^2$)$_a$—($Y^1$)$_b$—($R^2$)$_c$—$R^3$ a, b and c are the same or different and are each independently 0 or 1 and at least one of a or b is 1;

n is 0, 1, 2, 3 or 4;

$Q^2$ is a group of formula: —($R^2$)$_{aa}$—($Y^2$)$_{bb}$—($R^2$)$_{cc}$—$R^4$ or two adjacent $Q^2$ groups are selected from the group consisting of alkyl, alkenyl, —O$R^7$, —S(O)$_fR^7$ and —N$R^7R^8$ and together with the carbon atoms to which they are bound, they form a $C_{5-6}$cycloalkyl, $C_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S;

aa, bb and cc are the same or different and are each independently 0 or 1;

each $Y^1$ and $Y^2$ is the same or different and is independently selected from the group consisting of —O—, —S(O)$_f$—, —N($R^7$)—, —C(O)—, —OC(O)—, —CO$_2$—, —C(O)N($R^7$)—, —C(O)N($R^7$)S(O)$_2$—, —OC(O)N($R^7$)—, —OS(O)$_2$—, —S(O)$_2$N($R^7$)—, —S(O)$_2$N($R^7$)C(O)—, —N($R^7$)S(O)$_2$—, —N($R^7$)C(O)—, —N($R^7$)CO$_2$— and —N($R^7$)C(O)N($R^7$)—;

each $R^2$ is the same or different and is independently selected from the group consisting of alkylene, alkenylene and alkynylene;

each $R^3$ and $R^4$ is the same or different and is each independently selected from the group consisting of H, halo, alkyl, alkenyl, alkynyl, —C(O)$R^7$, —C(O)N$R^7R^8$, —CO$_2R^7$, —C(S)$R^7$, —C(S)N$R^7R^8$, —C(=N$R^7$)$R^8$, —C(=N$R^7$)N$R^7R^8$, —C$R^7$=N—O$R^7$, —O$R^7$, —S(O)$_fR^7$, —S(O)$_2$N$R^7R^8$, —N$R^7R^8$, —N($R^7$)C(O)$R^8$, —N($R^7$)S(O)$_2R^8$, —NO$_2$, —CN, —N$_3$ and a group of formula (ii):

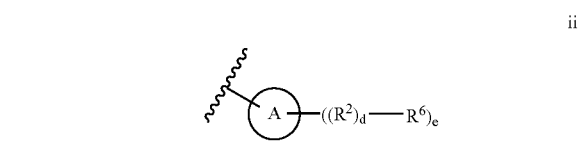

wherein:

Ring A is selected from the group consisting of $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S;

each d is 0 or 1;

e is 0, 1, 2, 3 or 4;

each $R^6$ is the same or different and is independently selected from the group consisting of H, halo, alkyl, alkenyl, alkynyl, cycloalkyl, cycloalkenyl, Ph, Het, —CH(OH)—$R^2$—OH, —C(O)$R^7$, —CO$_2R^7$, —CO$_2$—$R_2$-Ph, —CO$_2$—$R^2$-Het, —C(O)N$R^7R^8$, —C(O)N($R^7$)C(O)$R^7$, —C(O)N($R^7$)CO$_2R^7$, —C(O)N($R^7$)C(O)N$R^7R^8$, —C(O)N($R^7$)S(O)$_2R^7$, —C(S)

R⁷, —C(S)NR⁷R⁸, —C(=NR⁷)R⁸, —C(=NR⁷)NR⁷R⁸, —CR⁷=N—OR⁸, =O, —OR⁷, —OC(O)R⁷, —OC(O)Ph, —OC(O)Het, —OC(O)NR⁷R⁸, —O—R²—S(O)₂R⁷, —S(O)ᵣR⁷, —S(O)₂NR⁷R⁸, —S(O)₂Ph, —S(O)₂Het, —NR⁷R⁸, —N(R⁷)C(O)R⁸, —N(R⁷)CO₂R⁸, —N(R⁷)—R²—CO₂R⁸, —N(R⁷)C(O)NR⁷R⁸, —N(R⁷)—R²—C(O)NR⁷R⁸, —N(R⁷)C(O)Ph, —N(R⁷)C(O)Het, —N(R⁷)Ph, —N(R⁷)Het, —N(R⁷)C(O)NR⁷—R²—NR⁷R⁸, —N(R⁷)C(O)N(R⁷)Ph, —N(R⁷)C(O)N(R⁷)Het, —N(R⁷)C(O)N(R⁷)—R²-Het, —N(R⁷)S(O)₂R⁸, —N(R⁷)—R²—S(O)₂R⁸, —NO₂, —CN and —N₃;

wherein when Q¹ is defined where b is 1 and c is 0, R³ is not halo, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —S(O)ᵣR⁷, —S(O)₂NR⁷R⁸, —NR⁷R⁸, —N(R⁷)C(O)R⁸, —N(R⁷)S(O)₂R⁸, —NO₂, —CN or —N₃;

wherein when Q² is defined where bb is 1 and cc is 0, R⁴ is not halo, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —S(O)ᵣR⁷, —S(O)₂NR⁷R⁸, —NR⁷R⁸, —N(R⁷)C(O)R⁸, —N(R⁷)S(O)₂R⁸, —NO₂, —CN or —N₃;

R⁵ is selected from the group consisting of H, halo, alkyl, cycloalkyl, OR⁷, —S(O)ᵣR⁷, —NR⁷R⁸, —NHC(O)R⁷, —NHC(O)NR⁷R⁸ and —NHS(O)₂R⁷;

f is 0, 1 or 2; and each R⁷ and each R⁸ are the same or different and are each independently selected from the group consisting of H, alkyl, alkenyl, alkynyl, cycloalkyl and cycloalkenyl;

or a pharmaceutically acceptable salt, solvate or physiologically functional derivative thereof.

The process comprises the step of reacting one equivalent of a compound of formula (III):

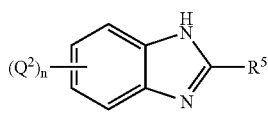

III or an acid addition salt thereof, with one equivalent of a compound of formula (IV):

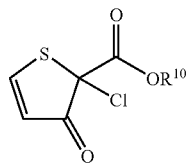

IV wherein R¹⁰ is selected from alkyl, alkenyl, alkynyl, cycloalkyl, cycloalkenyl and suitable carboxylic acid protecting groups;

in the presence of a base additive.

In one embodiment, the present invention further comprises the step of converting the compound of formula (I) to a pharmaceutically acceptable salt, solvate or physiologically functional derivative thereof.

In one embodiment, the present invention further comprises the step of converting the compound of formula (I) or a pharmaceutically acceptable salt, solvate or physiologically functional derivative thereof into a different compound of formula (I) or a pharmaceutically acceptable salt, solvate or physiologically functional derivative thereof.

DETAILED DESCRIPTION OF THE INVENTION

As used herein, the terms "alkyl" (and "alkylene") refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl groups may be optionally substituted one or more times with a halogen. Thus, the term "alkyl" includes trifluoromethyl and trifluoroethyl, among other halogenated alkyls.

As used herein, the term "alkenyl" refers to straight or branched hydrocarbon chains containing from 2 to 8 carbon atoms (unless a different number of atoms is specified) and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted one or more times with a halogen.

As used herein, the term "alkynyl" refers to straight or branched hydrocarbon chains containing from 2 to 8 carbon atoms (unless a different number of atoms is specified) and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted one or more times with a halogen.

As used herein, the term "cycloalkyl" refers to a non-aromatic monocyclic carbocyclic ring having from 3 to 8 carbon atoms (unless a different number of atoms is specified) and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more substituents selected from the group consisting of halo, $C_{1-3}$alkyl (including haloalkyl, e.g., perfluoroalkyl), —OH, —O—$C_{1-3}$alkyl, —NH₂, —NH($C_{1-3}$alkyl) —N($C_{1-3}$alkyl)₂, —CN and —N₃. Preferred cycloalkyl groups include $C_{3-6}$cycloalkyl and substituted $C_{3-6}$cycloalkyl.

As used herein, the term "cycloalkenyl" refers to a non-aromatic monocyclic carbocyclic ring having from 3 to 8 carbon atoms (unless a different number of atoms is specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on any available carbon with one or more substituents selected from the group consisting of halo, $C_{1-3}$alkyl (including haloalkyl, e.g., perfluoroalkyl), —OH, —O—$C_{1-13}$alkyl, —NH₂, —NH($C_{1-3}$alkyl), —N($C_{1-3}$alkyl)₂, —CN and —N₃.

The term "halo" or "halogen" refers to fluorine, chlorine, bromine and iodine.

The term "oxo" as used herein refers to the group =O attached directly to a carbon atom of a hydrocarbon ring (i.e., cycloalkenyl, aryl, heterocycle or heteroaryl ring) as well as —N-oxides, sulfones and sulfoxides wherein the N or S are atoms of a heterocyclic or heteroaryl ring.

The term "aryl" refers to monocyclic carbocyclic groups and fused bicyclic carbocyclic groups having from 6 to 13 carbon atoms (unless a different number of atoms is specified) and having at least one aromatic ring. Examples of particular aryl groups include but are not limited to phenyl and naphthyl. One particular aryl group according to the invention is phenyl.

The terms "heterocycle" and "heterocyclic" refer to monocyclic saturated or unsaturated non-aromatic groups and fused bicyclic saturated or unsaturated non-aromatic groups, having the specified number of members and containing 1, 2, 3 or 4 heteroatoms selected from N, O and S (unless a different number of heteroatoms is specified). Examples of particular heterocyclic groups include but are not limited to tetrahydrofuran, dihydropyran, tetrahydropyran, pyran, tetrahydropyran, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like.

The term "heteroaryl" refers to aromatic monocyclic groups and fused bicyclic groups wherein at least one ring is aromatic, having the specified number of members and containing 1, 2, 3, or 4 heteroatoms selected from N, O and S (unless a different number of heteroatoms is specified). Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The compounds of formula (I) are defined wherein:

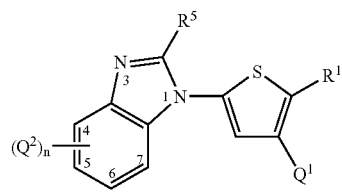

I wherein:
$R^1$ is selected from the group consisting of H, alkyl, alkenyl, alkynyl, —C(O)$R^7$, —CO$_2R^7$, —C(O)NR$^7R^8$, —C(O)N($R^7$)O$R^8$, —C(O)N($R^7$)—$R^2$—O$R^8$, —C(O)N($R^7$)-Ph, —C(O)N($R^7$)—$R^2$-Ph, —C(O)N($R^7$)C(O)$R^8$, —C(O)N($R^7$)CO$_2R^8$, —C(O)N($R^7$)C(O)NR$^7R^8$, —C(O)N($R^7$)S(O)$_2R^8$, —$R^2$—O$R^7$, —$R^2$—O—C(O)$R^7$, —C(S)$R^7$, —C(S)NR$^7R^8$, —C(S)N($R^7$)-Ph, —C(S)N($R^7$)—$R^2$-Ph, —$R^2$—S$R^7$, —C(=N$R^7$)NR$^7R^8$, —C(=N$R^7$)N($R^8$)-Ph, —C(=N$R^7$)N($R^8$)—$R^2$-Ph, —$R^2$—NR$^7R^8$, —CN, —O$R^7$, —S(O)$_rR^7$, —S(O)$_2$NR$^7R^8$, —S(O)$_2$N($R^7$)-Ph, —S(O)$_2$N($R^7$)—$R^2$-Ph, —NR$^7R^8$, N($R^7$)-Ph, —N($R^7$)—$R^2$-Ph, —N($R^7$)—SO$_2R^8$ and Het;
Ph is phenyl optionally substituted from 1 to 3 times with a substituent selected from the group consisting of halo, alkyl, —OH, —$R^2$—OH, —O-alkyl, —$R^2$—O-alkyl, —NH$_2$, —N(H)alkyl, —N(alkyl)$_2$, —CN and —N$_3$;

Het is a 5-7 membered heterocycle having 1, 2, 3 or 4 heteroatoms selected from N, O and S, or a 5-6 membered heteroaryl having 1, 2, 3 or 4 heteroatoms selected from N, O and S, each optionally substituted from 1 to 2 times with a substituent selected from the group consisting of halo, alkyl, oxo, —OH, —$R^2$—OH, —O-alkyl, —$R^2$—O-alkyl, —NH$_2$, —N(H)alkyl, —N(alkyl)$_2$, —CN and —N$_3$;
$Q^1$ is a group of formula: —($R^2$)$_a$—($Y^1$)$_b$—($R^2$)$_c$—$R^3$
a, b and c are the same or different and are each independently 0 or 1 and at least one of a or b is 1;
n is 0, 1, 2, 3 or 4;
$Q^2$ is a group of formula: —($R^2$)$_{aa}$—($Y^2$)$_{bb}$—($R^2$)$_{cc}$—$R^4$
or two adjacent $Q^2$ groups are selected from the group consisting of alkyl, alkenyl, —O$R^7$, —S(O)$_rR^7$ and —NR$^7R^8$ and together with the carbon atoms to which they are bound, they form a $C_{5-6}$cycloalkyl, $C_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S;
aa, bb and cc are the same or different and are each independently 0 or 1;
each $Y^1$ and $Y^2$ is the same or different and is independently selected from the group consisting of —O—, —S(O)$_r$—, —N($R^7$)—, —C(O)—, —OC(O)—, —CO$_2$—, —C(O)N($R^7$)—, —C(O)N($R^7$)S(O)$_2$—, —OC(O)N($R^7$)—, —OS(O)$_2$—, —S(O)$_2$N($R^7$)—, —S(O)$_2$N($R^7$)C(O)—, —N($R^7$)S(O)$_2$—, —N($R^7$)C(O)—, —N($R^7$)CO$_2$— and —N($R^7$)C(O)N($R^7$)—;
each $R^2$ is the same or different and is independently selected from the group consisting of alkylene, alkenylene and alkynylene;
each $R^3$ and $R^4$ is the same or different and is each independently selected from the group consisting of H, halo, alkyl, alkenyl, alkynyl, —C(O)$R^7$, —C(O)NR$^7R^8$, —CO$_2R^7$, —C(S)$R^7$, —C(S)NR$^7R^8$, —C(=N$R^7$)$R^8$, —C(=N$R^7$)NR$^7R^8$, —C$R^7$=N—O$R^7$, —O$R^7$, —S(O)$_rR^7$, —S(O)$_2$NR$^7R^8$, —NR$^7R^8$, —N($R^7$)C(O)$R^8$, —N($R^7$)S(O)$_2R^8$, —NO$_2$, —CN, —N$_3$ and a group of formula (ii):

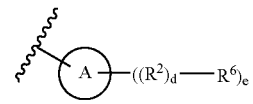

ii wherein:
Ring A is selected from the group consisting of $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S
each d is 0 or 1;
e is 0, 1, 2, 3 or 4;
each $R^6$ is the same or different and is independently selected from the group consisting of H, halo, alkyl, alkenyl, alkynyl, cycloalkyl, cycloalkenyl, Ph, Het, —CH(OH)—$R^2$—OH, —C(O)$R^7$, —CO$_2R^7$, —CO$_2$—$R_2$-Ph, —CO$_2$—$R^2$-Het, —C(O)NR$^7R^8$, —C(O)N($R^7$)C(O)$R^7$, —C(O)N($R^7$)CO$_2R^7$, —C(O)N($R^7$)C(O)NR$^7R^8$, —C(O)N($R^7$)S(O)$_2R^7$, —C(S)$R^7$, —C(S)NR$^7R^8$, —C(=N$R^7$)$R^8$, —C(=N$R^7$)NR$^7R^8$, —C$R^7$=N—O$R^8$, =O, —O$R^7$, —OC(O)$R^7$, —OC(O)Ph, —OC(O)Het, —OC(O)NR$^7R^8$, —O—$R^2$—S(O)$_2R^7$, —S(O)$_rR^7$, —S(O)$_2$NR$^7R^8$, —S(O)$_2$Ph, —S(O)$_2$Het, —NR$^7R^8$, —N($R^7$)C(O)$R^8$, —N($R^7$)CO$_2R^8$, —N($R^7$)—$R^2$—CO$_2R^8$, —N($R^7$)C(O)N$R^7R^8$, —N($R^7$)—$R^2$C(O)N$R^7R^8$, —N($R^7$)C(O)Ph, —N($R^7$)C(O)Het, —N($R^7$)Ph, —N($R^7$)Het, —N($R^7$)C(O)N$R^7$—$R^2$—N$R^7R^8$, —N($R^7$)C(O)N($R^7$)Ph, —N($R^7$)C(O)N($R^7$)Het, —N($R^7$)C(O)N($R^7$)—$R^2$-Het, —N($R^7$)S(O)$_2R^8$, —N($R^7$)—$R^2$—S(O)$_2R^8$, —NO$_2$, —CN and —N$_3$;

$R^5$ is selected from the group consisting of H, halo, alkyl, cycloalkyl, —O$R^7$, —S(O)$_fR^7$, —N$R^7R^8$, —NHC(O)$R^7$, —NHC(O)N$R^7R^8$ and —NHS(O)$_2R^7$;

f is 0, 1 or 2; and each $R^7$ and each $R^8$ are the same or different and are each independently selected from the group consisting of H, alkyl, alkenyl, alkynyl, cycloalkyl and cycloalkenyl;

and pharmaceutically acceptable salts, solvates and physiologically functional derivatives thereof.

In one embodiment, the compounds of formula (I) are defined wherein $R^1$ is selected from the group consisting of alkyl, alkenyl, alkynyl, —C(O)$R^7$, —CO$_2R^7$, —C(O)N$R^7R^8$, —C(O)N($R^7$)—$R^2$—O$R^8$, —$R^2$—O$R^7$, —C(S)N$R^7R^8$, —C(=N$R^7$)N$R^7R^8$, —CN, —S(O)$_fR^7$, —S(O)$_2$N$R^7R^8$, and Het, or any subset thereof. In one embodiment, the compounds of formula (I) are defined wherein $R^1$ is selected from the group consisting of —C(O)$R^7$, —CO$_2R^7$, —C(S)N$R^7R^8$, Het, and —C(O)N$R^7R^8$, or any subset thereof. In one embodiment, the compounds of formula (I) are defined wherein $R^1$ is selected from the group consisting of —C(O)$R^7$, —CO$_2R^7$ and —C(O)N$R^7R^8$, or any subset thereof. In one particular embodiment, $R^1$ is selected from the group consisting of —CO$_2R^7$ and —C(O)N$R^7R^8$, or any subset thereof. In one embodiment, $R^1$ is —CO$_2R^7$. In one embodiment, $R^1$ is —C(O)N$R^7R^8$.

Specific examples of groups defining $R^1$ include but are not limited to —COH, —COCH$_3$, —COOH, —COOCH$_3$, —C(O)NH$_2$, —CONH(alkyl), —CON(alkyl)(alkyl), —CONH(Et-OH), —CONH(benzyl), —CONH(phenyl), —S(O)$_2$NH$_2$ and —S(O)$_2$N(H)CH$_3$, —CH$_2$OH, —C(S)NH$_2$, —CN, and -tetrazole, or any subset thereof. In one particular embodiment, $R^1$ is selected from the group consisting of —CO$_2$H and —C(O)NH$_2$.

$Q^1$ is defined as a group of formula: —($R^2$)$_a$—($Y^1$)$_b$—($R^2$)$_c$—$R^3$.

In the foregoing formula, a, b and c are the same or different and are each independently 0 or 1.

In one embodiment, $Q^1$ is defined wherein a is 0. In the embodiment wherein a is 1 and thus the ($R^2$)$_a$ group is present, $R^2$ is typically alkylene or alkenylene, more particularly alkylene. In one particular embodiment, $Q^1$ is defined where a is 1 and ($R^2$)$_a$ is $C_{1-3}$alkylene.

In one embodiment, $Q^1$ in the compounds of formula (I) is defined where b is 1; thus $Y^1$ is present. In one such embodiment, $Y^1$ is selected from —O—, —S(O)$_f$—, —N($R^7$)—, —C(O)—, —OC(O)—, —CO$_2$—, —C(O)N($R^7$)—, —C(O)N($R^7$)S(O)$_2$—, —OC(O)N($R^7$)—, —OS(O)$_2$—, —S(O)$_2$N($R^7$)—, —S(O)$_2$N($R^7$)C(O)—, —N($R^7$)S(O)$_2$—, —N($R^7$)C(O)—, —N($R^7$)CO$_2$— and —N($R^7$)C(O)N($R^7$)—. In one particular embodiment, $Y^1$ is selected from —O—, —N($R^7$)—, —C(O)—, —OC(O)—, —C(O)N($R^7$)—, —OS(O)$_2$—, —S(O)$_2$N($R^7$)—, —N($R^7$)S(O)$_2$—, and —N($R^7$)C(O)—, or any subset thereof. In another particular embodiment, $Y^1$ is selected from —O—, —N($R^7$)—, —C(O)—, —OS(O)$_2$—, —N($R^7$)S(O)$_2$—, and —N($R^7$)C(O)—, or any subset thereof. In one particular embodiment, b is 1 and $Y^1$ is —O—, —N($R^7$)—, —C(O)— or —OS(O)$_2$—, or any subset thereof. In one particular embodiment, b is 1 and $Y^1$ is —O—. In another particular embodiment, b is 1 and $Y^1$ is —N($R^7$)— and $R^7$ is H or alkyl, more particularly H. In another particular embodiment, b is 1 and $Y^1$ is —C(O)—. In another particular embodiment, b is 1 and $Y^1$ is —OS(O)$_2$—.

The variable c in the formula $Q^1$ can be 0 or 1. In one embodiment, c is 1. In one such embodiment ($R^2$)$_c$ is alkylene or alkenylene, more particularly alkylene. In one particular embodiment, $Q^1$ is defined where c is 1 and ($R^2$)$_c$ is $C_{1-3}$alkylene.

In one embodiment, the compounds of formula (I) are defined to include a substitution at the position indicated by $Q^1$; thus, when a, b and c are all 0, then $R^3$ is not H. In one particular embodiment the compounds of the present invention are defined wherein, at least one of a or b is 1. In one particular embodiment, $Q^1$ is defined wherein both b and c are 1. In one particular embodiment, $Q^1$ is defined wherein a is 0 and both b and c are 1.

Consistent with the definition of b, $Y^1$ and c, the group $R^3$ may be selected from the group consisting of H, halo, alkyl, alkenyl, alkynyl, —C(O)$R^7$, —C(O)N$R^7R^8$, —CO$_2R^7$, —C(S)$R^7$, —C(S)N$R^7R^8$, —C(=N$R^7$)$R^8$, —C(=N$R^7$)N$R^7R^8$, —C$R^7$=N—O$R^7$, —O$R^7$, —S(O)$_fR^7$, —S(O)$_2$N$R^7R^8$, —N$R^7R^8$, —N($R^7$)C(O)$R^8$, —N($R^7$)S(O)$_2R^8$, —NO$_2$, —CN, —N$_3$ and a group of formula (ii):

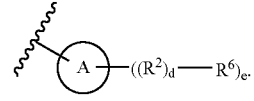

ii

In one embodiment, $R^3$ in the definition of $Q^1$ is selected from the group consisting of H, alkyl, alkenyl, alkynyl, and a group of formula (ii), or any subset thereof. In one particular embodiment, $R^3$ is selected from the group consisting of H, alkyl, alkenyl and alkynyl, or any subset thereof. In one embodiment, when $R^3$ is alkyl, $R^3$ is $C_{2-6}$alkyl.

In one particular embodiment, $R^3$ is a group of formula (ii).

in formula (ii) is referred to herein as "Ring A." Ring A is selected from $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S. In $Q^1$, Ring A may be bonded to $R^2$, $Y^1$ (when c is 0) or the thiophene ring (when a, b and c are 0) through any suitable carbon or heteroatom. In one embodiment, $Q^1$ is defined wherein $R^3$ is a group of formula (ii) and Ring A is selected from $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S. In one embodiment, $Q^1$ is defined wherein $R^3$ is a group of formula (ii) and Ring A is selected from aryl, 5-10 membered heterocycle having 1, 2 or 3 heteroatoms selected from N, O and S and 5-10 membered heteroaryl having 1, 2 or 3 heteroatoms selected from N, O and S. In one particular embodiment, $Q^1$ is defined wherein $R^3$ is a group of formula (ii) and Ring A is selected from aryl and 5-10 membered heteroaryl having 1, 2 or 3 heteroatoms selected from N, O and S.

In one embodiment, $Q^1$ is defined wherein $R^3$ is a group of formula (ii) and Ring A is selected from the group consisting of cycloalkyl, tetrahydropyran, tetrahydrofuran, morpholine, piperidine, phenyl, naphthyl, thiophene, furan, pyrrole, pyrrolidine, pyrrolidinone, imidazole, benzofuran, benzimidazole, pyridyl,

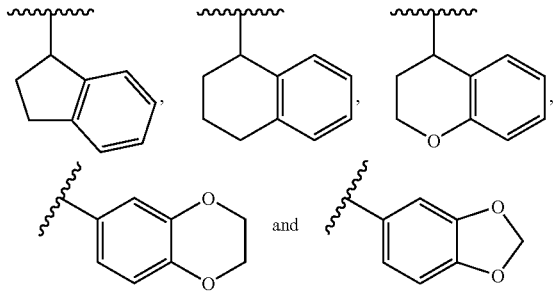

or any subset thereof. In one particular embodiment, Ring A is phenyl. In one particular embodiment Ring A is pyridyl.

Particular, more specific, examples of groups defining $Q^1$ in the compounds of formula (I) are selected from the group consisting of:

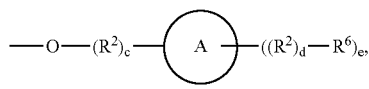

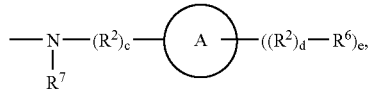

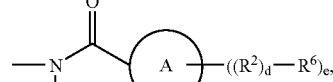

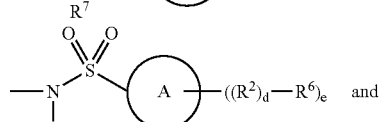

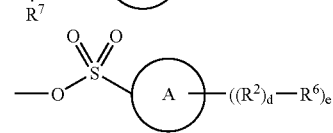

or any subset thereof.
One particular group defining $Q^1$ is

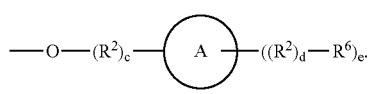

In one particular embodiment, $Q^1$ is

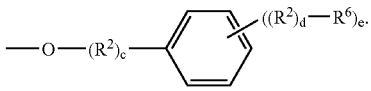

In one particular embodiment, $Q^1$ is

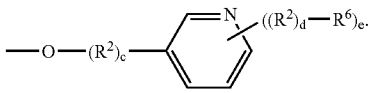

In one particular embodiment, $Q^1$ is

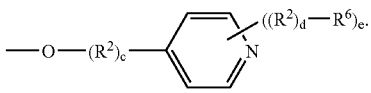

In one embodiment the compounds of formula (I) are defined wherein $R^3$ is a group of formula (ii) and d is 0 or 1. In a particular embodiment, wherein $R^3$ is a group of formula (ii) and d is 1, $R^2$ is $C_{1-3}$alkylene. In one embodiment, d is 0.

In one embodiment, wherein the compounds of formula (I) are defined wherein $R^3$ is a group of formula (ii), e is 0, 1, 2 or 3. In one particular embodiment, e is 0 or 1. In one embodiment, e is 1. In one embodiment, e is 2.

In one embodiment, wherein the compounds of formula (I) are defined wherein $R^3$ is a group of formula (ii), each $R^6$ is the same or different and is independently selected from the group consisting, of H, halo, alkyl, alkenyl, alkynyl, cycloalkyl, Ph, Het, —CH(OH)—$R^2$—OH, —C(O)$R^7$, —C(O)N$R^7R^8$, =O, —O$R^7$, —S(O)$_f R^7$, —S(O)$_2$N$R^7R^8$, —SO$_2$Ph, —N$R^7R^8$, —N($R^7$)C(O)$R^8$, —N($R^7$)CO$_2R^8$, —N($R^7$)S(O)$_2R^8$, —NO$_2$, —CN and —N$_3$, or any subset thereof. In one particular embodiment, $R^3$ is a group of formula (ii) and each $R^6$ is the same or different and is independently selected from the group consisting of H, halo, alkyl, alkenyl, alkynyl, cycloalkyl, —O$R^7$, —S(O)$_f R^7$, —S(O)$_2$N$R^7R^8$, —N$R^7R^8$, —N($R^7$)S(O)$_2R^8$, —NO$_2$ and —CN or any subset thereof. In one particular embodiment, $R^3$ is a group of formula (ii) and each $R^6$ is the same or different and is independently selected from the group consisting of H, halo, alkyl, —O$R^7$, —S(O)$_f R^7$, —S(O)$_2$N$R^7R^8$ and —NO$_2$, or any subset thereof.

More specifically, in one embodiment wherein $R^3$ is a group of formula (ii), each $R^6$ is the same or different and is independently selected from the group consisting of H, F, Cl, Br, I, methyl, trifluoromethyl, ethyl, propyl, isopropyl, cyclopropyl, iso-butyl, t-butyl, ethenyl, propenyl, acetylene, O-methyl, O-difluoromethyl, O-trifluoromethyl, O-ethyl, O-propyl, O-isopropyl, O-cyclopropyl, —SO$_2$-methyl, —SO$_2$NH$_2$, —NH$_2$, —NH(alkyl), —N(alkyl)alkyl, —NH(cyclopropyl), —NHSO$_2$-methyl, —NO$_2$, and —CN, or any subset thereof.

In one embodiment, $Q^1$ is defined such that when b is 1 and c is 0, $R^3$ is not halo, —C(O)$R^7$, —C(O)N$R^7R^8$, —CO$_2R^7$, —C(S)$R^7$, —C(S)N$R^7R^8$, —C(=N$R^7$)$R^8$, —C(=N$R^7$)N$R^7R^8$, —C$R^7$=N—O$R^7$, —O$R^7$, —S(O)$_f R^7$, —S(O)$_2$N$R^7$, —N$R^7R^8$, —N($R^7$)C(O)$R^8$, —N($R^7$)S(O)$_2R^8$, —NO$_2$, —CN or —N$_3$.

In one embodiment, wherein when $R^1$ is —$CO_2CH_3$ and n is 0, $Q^1$ is not —OH. In one embodiment, $Q^1$ is not —OH.

In one embodiment, n is 0, 1 or 2, or any subset thereof. In one particular embodiment, n is 0, and thus the benzimidazole ring is unsubstituted at positions C-4, C-5, C-6 and C-7. In one embodiment, n is 2 and $Q^2$ is at C-5 and C-6. In another particular embodiment, n is 1. In one particular embodiment n is 2.

$Q^2$ is a group of formula —$(R^2)_{aa}$—$(Y^2)_{bb}$—$(R^2)_{cc}$—$R^4$. $Q^2$ may be located at any of C-4, C-5, C-6 and/or C-7 of the benzimidazole ring. In one embodiment, n is 1 and $Q^2$ is at C-5. In one embodiment, n is 1 and $Q^2$ is at C-6.

In the foregoing formula, aa, bb and cc are the same or different and are each independently 0 or 1.

In one embodiment, aa is 0; thus the group $(R^2)_{aa}$ is not present. In the embodiment wherein aa is 1, $(R^2)_{aa}$ is typically alkylene or alkenylene, more particularly alkylene. In one particular embodiment, $Q^2$ is defined where aa is 1 and $(R^2)_{aa}$ is $C_{1-3}$alkylene.

In one embodiment, the compounds of formula (I) are defined wherein bb is 0. In another embodiment, $Q^2$ in the compounds of formula (I) is defined where bb is 1; thus $Y^2$ is present. In one such embodiment, $Y^2$ is selected from —O—, —S(O)$_f$—, —N(R$^7$)—, —C(O)—, —OC(O)—, —CO$_2$—, —C(O)N(R$^7$)—, —C(O)N(R$^7$)S(O)$_2$—, —OC(O)N(R$^7$)—, —OS(O)$_2$—, —S(O)$_2$N(R$^7$)—, —S(O)$_2$N(R$^7$)C(O)—, —N(R$^7$)S(O)$_2$—, —N(R$^7$)C(O)—, —N(R$^7$)CO$_2$— and —N(R$^7$)C(O)N(R$^7$)—. In one particular embodiment, bb is 1 and $Y^2$ is selected from —O—, —S(O)$_f$—, —N(R$^7$)—, —C(O)—, —OC(O)—, —CO$_2$—, —C(O)N(R$^7$)—, —OS(O)$_2$—, —N(R$^7$)S(O)$_2$—, —N(R$^7$)C(O)—, —N(R$^7$)CO$_2$— and —N(R$^7$)C(O)N(R$^7$)—, or any subset thereof. In another particular embodiment, bb is 1 and $Y^2$ is selected from —O—, —S(O)$_f$—, —N(R$^7$)—, —CO$_2$—, —C(O)N(R$^7$)—, —N(R$^7$)S(O)$_2$—, and —N(R$^7$)C(O)—, —N(R$^7$)CO$_2$—N(R$^7$)C(O)N(R$^7$)—, or any subset thereof. In one particular embodiment, $Q^2$ is defined wherein bb is 1 and $Y^2$ is selected from —O—, —S(O)$_f$—, —N(R$^7$)—, —CO$_2$— and —C(O)N(R$^7$)—, or any subset thereof. In one particular embodiment, $Q^2$ is defined wherein bb is 1 and $Y^2$ is —O—. In one particular embodiment, $Q^2$ is defined wherein bb is 1 and $Y^2$ is —S(O)$_f$—, wherein f is 2. In another particular embodiment, bb is 1 and $Y^2$ is —N(R$^7$)— and R$^7$ is H or alkyl, more particularly H. In another particular embodiment, bb is 1 and $Y^2$ is —CO$_2$—. In another particular embodiment, bb is 1 and $Y^2$ is —C(O)N(R$^7$)—.

The variable cc in the formula $Q^2$ can be 0 or 1. In one embodiment, cc is 1. In one such embodiment $(R^2)_{cc}$ is alkylene or alkenylene, more particularly alkylene. In one particular embodiment, $Q^2$ is defined where cc is 1 and $(R^2)_{cc}$ is $C_{1-3}$alkylene.

Consistent with the definition of bb, $Y^2$ and cc, the group $R^4$ may be selected from the group consisting of H, halo, alkyl, alkenyl, alkynyl, —C(O)R$^7$, —C(O)NR$^7$R$^8$, —CO$_2$R$^7$, —C(S)R$^7$, —C(S)NR$^7$R$^8$, —C(=NR$^7$)R$^8$, —C(=NR$^7$)NR$^7$R$^8$, —CR$^7$=N—OR$^7$, —OR$^7$, —S(O)$_f$R$^7$, —S(O)$_2$NR$^7$R$^8$, —NR$^7$R$^8$, —N(R$^7$)C(O)R$^8$, —N(R$^7$)S(O)$_2$R$^8$, —NO$_2$, —CN, —N$_3$ and a group of formula (ii):

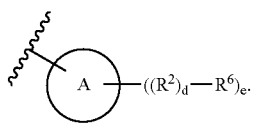

ii

In one embodiment, R$^4$ in the definition of $Q^2$ is selected from the group consisting H, halo, alkyl, alkenyl, alkynyl, —C(O)NR$^7$R$^8$, —OR$^7$, —S(O)$_f$R$^7$, —S(O)$_2$NR$^7$R$^8$, —NR$^7$R$^8$, —N(R$^7$)C(O)R$^8$, —N(R$^7$)S(O)$_2$R$^8$, —NO$_2$, —CN, —N$_3$ and a group of formula (ii), or any subset thereof. In one particular embodiment, R$^4$ is selected from the group consisting of H, halo, alkyl, —OR$^7$, —S(O)$_f$R$^7$, —S(O)$_2$NR$^7$R$^8$, —NR$^7$R$^8$, and a group of formula (ii), or any subset thereof. In one embodiment, R$^4$ is selected from H, halo, alkyl, —OR$^7$, —NR$^7$R$^8$, and a group of formula (ii), or any subset thereof.

In one particular embodiment, R$^4$ is a group of formula (ii). In the embodiment, wherein R$^4$ is a group of formula (ii), Ring A is selected from $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S. In one embodiment, wherein R$^4$ is a group of formula (ii), Ring A is selected from $C_{5-6}$cycloalkyl, $C_{5-6}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S. In $Q^2$, Ring A may be bonded to the R$^2$, Y$^2$ (when cc is 0) or the benzimidazole (when aa, bb and cc are 0) through any suitable carbon or heteroatom. In one embodiment, $Q^2$ is defined wherein R$^4$ is a group of formula (ii) and Ring A is selected from aryl, 5-10 membered heterocycle having 1, 2 or 3 heteroatoms selected from N, O and S and 5-10 membered heteroaryl having 1, 2 or 3 heteroatoms selected from N, O and S. In one particular embodiment, $Q^2$ is defined wherein R$^4$ is a group of formula (ii) and Ring A is selected from aryl and 5-10 membered heterocycle having 1, 2 or 3 heteroatoms selected from N, O and S.

In one embodiment, $Q^2$ is defined wherein R$^4$ is a group of formula (ii) and Ring A is selected from the group consisting of cycloalkyl, oxetane, oxazole, thiazole, morpholine, piperidine, piperazine, phenyl, naphthyl, thiophene, furan, pyrrolidine, pyrrolidinone, imidazole, triazole, imidazolidinone, benzofuran, benzodioxolane, benzimidazole and pyridyl, or any subset thereof. In one particular embodiment, Ring A is selected from morpholine, piperidine, piperazine, phenyl, pyrrolidinone, imidazolidinone and pyrrolidine, or any subset thereof.

More specifically, in one embodiment, each R$^4$ is the same or different and is independently selected from the group consisting of H, F, Cl, Br, I, methyl, trifluoromethyl, ethyl, propyl, isopropyl, cyclopropyl, iso-butyl, t-butyl, ethenyl, propenyl, acetylene, O-methyl, O-trifluoromethyl, O-ethyl, O-propyl, O-isopropyl, O-cyclopropyl, —SO$_2$-methyl, —SO$_2$NH$_2$, —NH$_2$, —NH(alkyl), —N(alkyl)alkyl, —NH(cyclopropyl), —NHC(O)-methyl, —NHC(O)NH$_2$, —NHSO$_2$-methyl, morpholino and piperizinyl, or any subset thereof.

Particular, more specific, examples of groups defining $Q^2$ in the compounds of formula (I) are selected from the group consisting of:

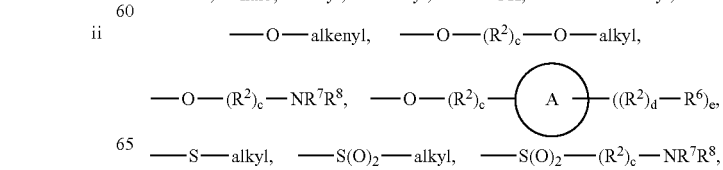

-continued

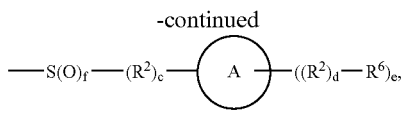

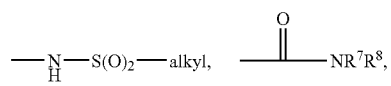

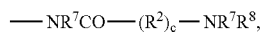

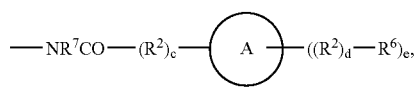

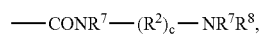

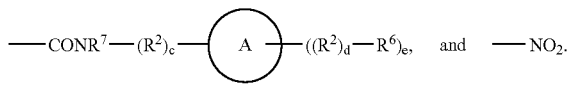

In one embodiment, $Q^2$ is —O-alkyl. In one particular embodiment, $Q^2$ is halo.

In one embodiment the compounds of formula (I) are defined wherein $R^4$ is a group of formula (ii) and d is 0 or 1. In a particular embodiment, wherein $R^4$ is a group of formula (ii) and d is 1, $R^2$ is $C_{1-3}$alkylene. In one embodiment, d is 0.

In one embodiment, wherein the compounds of formula (I) are defined wherein $R^4$ is a group of formula (ii), e is 0, 1, 2 or 3. In one particular embodiment, e is 0 or 1. In one embodiment, e is 0. In one embodiment, e is 1. In one embodiment, e is 2.

In one embodiment, wherein the compounds of formula (I) are defined wherein $R^4$ is a group of formula (ii), each $R^6$ is the same or different and is independently selected from the group consisting of H, halo, alkyl, alkenyl, alkynyl, Het, —C(O)$R^7$, —CO$_2R^7$, —C(O)NR$^7R^8$, =O, —OR$^7$, —S(O)$_fR^7$, —S(O)$_2$NR$^7R^8$, —NR$^7R^8$ and —N(R$^7$)S(O)$_2R^8$, or any subset thereof. In one particular embodiment, each $R^6$ is the same or different and is independently selected from the group consisting of H, halo, alkyl, =O, —OR$^7$, —S(O)$_fR^7$, —S(O)$^2$NR$^7R^8$ and —NR$^7R^8$, or any subset thereof.

More specifically, in one embodiment, each $R^6$ is the same or different and is independently selected from the group consisting of H, methyl, ethyl, propyl, isopropyl, iso-butyl, t-butyl, ethenyl, propenyl, cyclopropyl, pyrimidyl, —C(O)-alkyl, —CO$_2$-alkyl, —C(O)NH$_2$, acetylene, oxo, O-methyl, O-ethyl, O-propyl, O-isopropyl, O-cyclopropyl, —SO$_2$-methyl, —SO$_2$NH$_2$, —NH$_2$, —NH(alkyl), —N(alkyl)alkyl, —NH(cyclopropyl) and —NHSO$_2$-methyl, or any subset thereof.

In another embodiment of the present invention, two adjacent $Q^2$ groups are selected from the group consisting of alkyl, alkenyl, —OR$^7$, —S(O)$_fR^7$ and —NR$^7R^8$ and together with the carbon atoms to which they are bound, they form a $C_{5-6}$cycloalkyl, $C_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S. By "two adjacent $Q^2$ groups" is meant that two $Q^2$ groups are bonded to adjacent carbon atoms (e.g., C-4 and C-5). For example, in one embodiment two adjacent $Q^2$ groups are —OR$^7$ and together with the atoms to which they are bonded, they form a heterocyclic group such as:

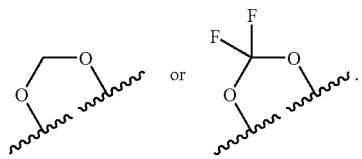

In another embodiment, two adjacent $Q^2$ groups are alkyl and together with the atoms to which they are bonded, they form a cycloalkyl group such as:

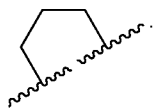

In another embodiment two adjacent $Q^2$ groups are defined as —OR$^7$ and —NR$^7R^8$ respectively and together with the atoms to which they are bonded, they form a heterocyclic group such as:

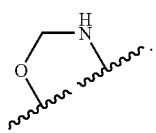

From these examples, additional embodiments can be readily ascertained by those skilled in the art. Preferably the compounds of formula (I) are defined wherein when n is 2, two adjacent $Q^2$ groups together with the atoms to which they are bonded do not form a $C_{5-6}$cycloalkyl, $C_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S.

In one embodiment, $Q^2$ is defined such that when bb is 1 and cc is 0, $R^4$ is not halo, —C(O)$R^7$, —C(O)NR$^7R^8$, —CO$_2R^7$, —C(S)$R^7$, —C(S)NR$^7R^8$, —C(=NR$^7$)$R^8$, —C(=NR$^7$)NR$^7R^8$, —CR$^7$=N—OR$^7$, —OR$^7$, —S(O)$_fR^7$, —S(O)$_2$NR$^7R^8$, —NR$^7R^8$, —N(R$^7$)C(O)R$^8$, —N(R$^7$)S(O)$_2R^8$, —NO$_2$, —CN or —N$_3$;

In one embodiment, $R^5$ is selected from the group consisting of H, halo, alkyl, —NR$^7R^8$ and —S(O)$_fR^7$, or any subset thereof. In another embodiment, $R^5$ is selected from the group consisting of H, halo, alkyl and —NR$^7R^8$, or any subset thereof. In one particular embodiment, $R^5$ is H. In one particular embodiment, $R^5$ is —NH$_2$.

More specifically, in one embodiment, $R^5$ is selected from the group consisting of H, F, Cl, Br, I, methyl, trifluoromethyl, ethyl, propyl, isopropyl, —S-methyl, —SO$_2$-methyl and —NH$_2$, or any subset thereof.

The compounds of formula (I) include compounds of formula (Ia):

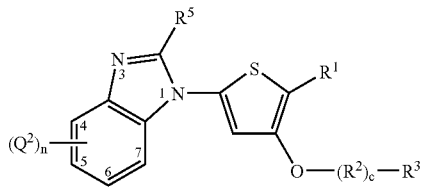

wherein all variables are as defined above, and pharmaceutically acceptable salts, solvates and physiologically functional derivatives thereof.

The compounds of formula (I) also include compounds of formula (Ib):

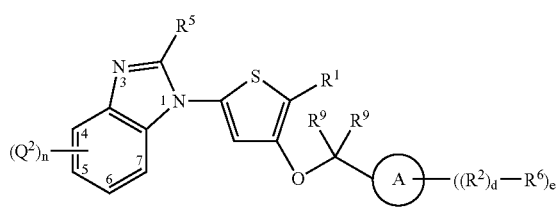

wherein each $R^9$ is the same or different and is selected from H, halo and alkyl; and all other variables are as defined above, and pharmaceutically acceptable salts, solvates and physiologically functional derivatives thereof.

It will be appreciated by those skilled in the art that the compounds of the present invention may also be utilized in the form of a pharmaceutically acceptable salt or solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like.

Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Compounds of formula (I) may be conveniently prepared by the process outlined in Scheme 1 below.

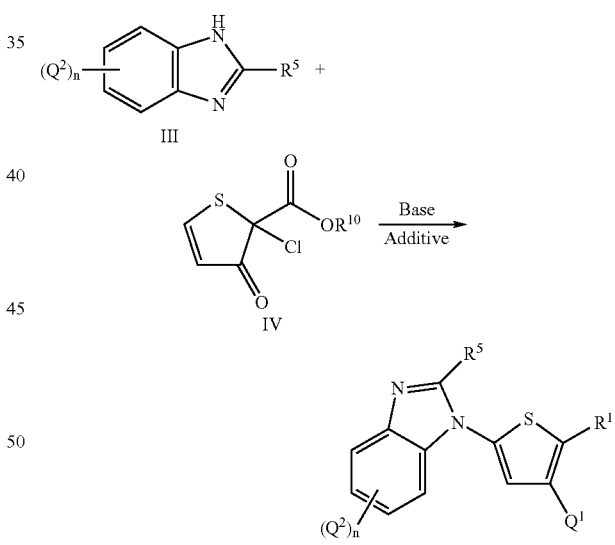

wherein:

$R^1$ is selected from the group consisting of H, alkyl, alkenyl, alkynyl, —C(O)$R^7$, —CO$_2R^7$, —C(O)NR$^7R^8$, —C(O)N(R$^7$)OR$^8$, —C(O)N(R$^7$)—R$^2$—OR$^8$, —C(O)N(R$^7$)-Ph, —C(O)N(R$^7$)—R$^2$-Ph, —C(O)N(R$^7$)C(O)R$^8$, —C(O)N(R$^7$)CO$_2R^8$, —C(O)N(R$^7$)C(O)NR$^7R^8$, —C(O)N(R$^7$)S(O)$_2R^8$, —R$^2$—OR$^7$, —R$^2$—O—C(O)R$^7$, —C(S)R$^7$, —C(S)NR$^7R^8$, —C(S)N(R$^7$)-Ph, —C(S)N(R$^7$)—R$^2$-Ph, —R$^2$—SR$^7$, —C(=NR$^7$)NR$^7R^8$, —C(=NR$^7$)N(R$^8$)-Ph, —C(=NR$^7$)N(R$^8$)—R$^2$-Ph, —$R^2$—$NR^7R^8$, —CN, —$OR^7$, —$S(O)_fR^7$, —$S(O)_2$ $NR^7R^8$, —$S(O)_2N(R^7)$-Ph, —$S(O)_2N(R^7)$—$R^2$-Ph, —$NR^7R^8$, $N(R^7)$-Ph, —$N(R^7)$—$R^2$-Ph, —$N(R^7)$—$SO_2R^8$ and Het;

Ph is phenyl optionally substituted from 1 to 3 times with a substituent selected from the group consisting of halo, alkyl, —OH, —$R^2$—OH, —O-alkyl, —$R^2$—O-alkyl, —$NH_2$, —N(H)alkyl, —$N(alkyl)_2$, —CN and —$N_3$;

Het is a 5-7 membered heterocycle having 1, 2, 3 or 4 heteroatoms selected from N, O and S, or a 5-6 membered heteroaryl having 1, 2, 3 or 4 heteroatoms selected from N, O and S, each optionally substituted from 1 to 2 times with a substituent selected from the group consisting of halo, alkyl, oxo, —OH, —$R^2$—OH, —O-alkyl, —$R^2$—O-alkyl, —$NH_2$, —N(H)alkyl, —$N(alkyl)_2$, —CN and —$N_3$;

$Q^1$ is a group of formula: —$(R^2)_a$—$(Y^1)_b(R^2)_c$—$R^3$ a, b and c are the same or different and are each independently 0 or 1 and at least one of a or b is 1;

n is 0, 1, 2, 3 or 4;

$Q^2$ is a group of formula: —$(R^2)_{aa}$—$(Y^2)_{bb}$—$(R^2)_{cc}$—$R^4$ or two adjacent $Q^2$ groups are selected from the group consisting of alkyl, alkenyl, —$OR^7$, —$S(O)_fR^7$ and —$NR^7R^8$, and together with the carbon atoms to which they are bound, they form a $C_{5-6}$cycloalkyl, $C_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S;

aa, bb and cc are the same or different and are each independently 0 or 1;

each $Y^1$ and $Y^2$ is the same or different and is independently selected from the group consisting of —O—, —$S(O)_f$—, —$N(R^7)$—, —C(O)—, —OC(O)—, —$CO_2$—, —$C(O)N(R^7)$—, —$C(O)N(R^7)S(O)_2$, —$OC(O)N(R^7)$—, —$OS(O)_2$—, —$S(O)_2N(R^7)$—, —$S(O)_2N(R^7)C(O)$—, —$N(R^7)S(O)_2$, —$N(R^7)C(O)$—, —$N(R^7)CO_2$— and —$N(R^7)C(O)N(R^7)$—;

each $R^2$ is the same or different and is independently selected from the group consisting of alkylene, alkenylene and alkynylene;

each $R^3$ and $R^4$ is the same or different and is each independently selected from the group consisting of H, halo, alkyl, alkenyl, alkynyl, —$C(O)R^7$, —$C(O)NR^7R^8$, —$CO_2R^7$, —$C(S)R^7$, —$C(S)NR^7R^8$, —$C(=NR^7)R^8$, —$C(=NR^7)NR^7R^8$, —$CR^7=N$—$OR^7$—$OR^7$, —$S(O)_f R^7$, —$S(O)_2NR^7R^8$, —$NR^7R^8$, —$N(R^7)C(O)R^8$, —$N(R^7)S(O)_2R^8$, —$NO_2$, —CN, —$N_3$ and a group of formula (ii):

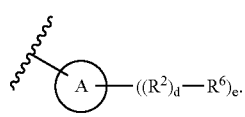

ii wherein:

Ring A is selected from the group consisting of $C_{5-10}$cycloalkyl, $C_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S each d is 0 or 1;

e is 0, 1, 2, 3 or 4;

each $R^6$ is the same or different and is independently selected from the group consisting of H, halo, alkyl, alkenyl, alkynyl, cycloalkyl, cycloalkenyl, Ph, Het, —CH(OH)—$R^2$—OH, —$C(O)R^7$, —$CO_2R^7$, —$CO_2$—$R_2$-Ph, —$CO_2$—$R^2$-Het, —$C(O)NR^7R^8$, —$C(O)N(R^7)C(O)R^7$, —$C(O)N(R^7)CO_2R^7$, —$C(O)N(R^7)C(O)NR^7R^8$, —$C(O)N(R^7)S(O)_2R^7$, —$C(S)R^7$, —$C(S)NR^7R^8$, —$C(=NR^7)R^8$, —$C(=NR^7)NR^7R^8$, —$CR^7=N$—$OR^8$, =O, —$OR^7$, —$OC(O)R^7$, —$OC(O)Ph$, —$OC(O)Het$, —$OC(O)NR^7R^8$, —O—$R^2$—$S(O)_2R^7$, —$S(O)_fR^7$, —$S(O)_2NR^7R^8$, —$S(O)_2Ph$, —$S(O)_2Het$, —$NR^7R^8$, —$N(R^7)C(O)R^8$, —$N(R^7)CO_2R^8$, —$N(R^7)$—$R^2$—$CO_2R^8$, —$N(R^7)C(O)NR^7R^8$, —$N(R^7)$—$R^2$—$C(O)NR^7R^8$, —$N(R^7)C(O)Ph$, —$N(R^7)C(O)Het$, —$N(R^7)Ph$, —$N(R^7)Het$, —$N(R^7)C(O)NR^7$—$R^2$—$NR^7R^8$, —$N(R^7)C(O)N(R^7)Ph$, —$N(R^7)C(O)N(R^7)Het$, —$N(R^7)C(O)N(R^7)$—$R^2$-Het, —$N(R^7)S(O)_2R^8$, —$N(R^7)$—$R^2$—$S(O)_2R^8$, —$NO_2$, —CN and —$N_3$;

wherein when $Q^1$ is defined where b is 1 and c is 0, $R^3$ is not halo, —$C(O)R^7$, —$C(O)NR^7R^8$, —$CO_2R^7$, —$C(S)R^7$, —$C(S)NR^7R^8$, —$C(=NR^7)R^8$, —$C(=NR^7)NR^7R^8$, —$CR^7=N$—$OR^7$, —$OR^7$, —$S(O)_fR^7$, —$S(O)_2NR^7R^8$, —$NR^7R^8$, —$N(R^7)C(O)R^8$, —$N(R^7)S(O)_2R^8$, —$NO_2$, —CN or —$N_3$;

wherein when $Q^2$ is defined where bb is 1 and cc is 0, $R^4$ is not halo, —$C(O)R^7$, —$C(O)NR^7R^8$, —$CO_2R^7$, —$C(S)R^7$, —$C(S)NR^7R^8$, —$C(=NR^7)R^8$, —$C(=NR^7)NR^7R^8$, —$CR^7=N$—$OR^7$, —$OR^7$, —$S(O)_fR^7$, —$S(O)_2NR^7R^8$, —$NR^7R^8$, —$N(R^7)C(O)R^8$, —$N(R^7)S(O)_2R^8$, —$NO_2$, —CN or —$N_3$;

$R^5$ is selected from the group consisting of H, halo, alkyl, cycloalkyl, $OR^7$, —$S(O)_fR^7$, —$NR^7R^8$, —$NHC(O)R^7$, —$NHC(O)NR^7R^8$ and —$NHS(O)_2R^7$;

f is 0, 1 or 2;

each $R^7$ and each $R^8$ are the same or different and are each independently selected from the group consisting of H, alkyl, alkenyl, alkynyl, cycloalkyl and cycloalkenyl; and $R^{10}$ is selected from alkyl, alkenyl, alkynyl, cycloalkyl, cycloalkenyl and suitable carboxylic acid protecting groups;

or a pharmaceutically acceptable salt, solvate or physiologically functional derivative thereof.

Generally, the process for preparing the compounds of formula (I) (all formulas and all variables having been defined above comprises the steps of:

a) reacting one equivalent of a compound of formula (III), or an acid addition salt thereof, with one equivalent of a compound of formula (IV) in the presence of a base additive to prepare a compound of formula (I);

b) optionally converting the compound of formula (I) to a pharmaceutically acceptable salt, solvate or physiologically functional derivative thereof; and c) optionally converting the compound of formula (I) or a pharmaceutically acceptable salt, solvate or physiologically functional derivative thereof to a different compound of formula (I) or a pharmaceutically acceptable salt, solvate or physiologically functional derivative thereof.

More specifically, compounds of formula (I) can be prepared by reacting a compound of formula (IV) with a compound of formula (III), or an acid addition salt thereof, in the presence of a base additive, to prepare a compound of formula (I-A).

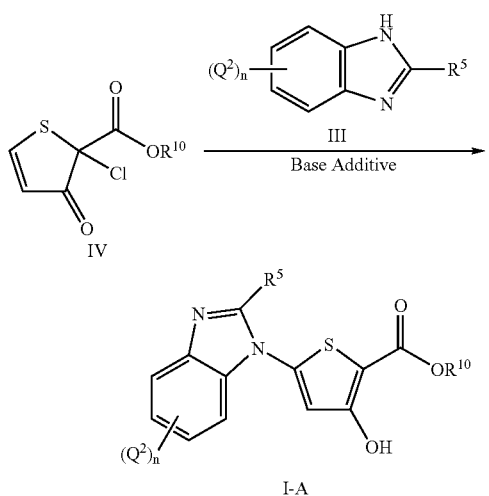

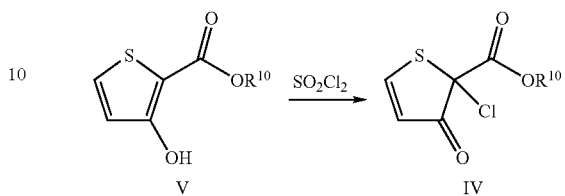

wherein all variables are as defined above.

A compound of formula (I-A) may be converted into a pharmaceutically acceptable salt, solvate or physiologically functional derivative thereof or may be converted to a different compound of formula (I) or a pharmaceutically acceptable salt, solvate or physiologically functional derivative thereof using techniques described hereinbelow and those conventional in the art.

Advantageously the process of the present invention permits the synthesis of a compound of formula (I) using one molar equivalent of a compound of formula (III) and one molar equivalent of a compound of formula (IV). Prior synthetic processes utilized two molar equivalents of the compound of formula (III). Given that the synthesis of the compounds of formula (III) requires multiple steps, the process of the instant invention has the advantage of decreased resource requirements in terms of starting materials.

Acid addition salts of the compound of formula (III) include any suitable acid addition salt, including for example the hydrochloride or acetic acid salts and can be prepared using techniques conventional in the art. See, e.g., Burger's Medicinal Chemistry And Drug Discovery 5th Edition, Vol 1: Principles And Practice.

The reaction is typically carried out in the presence of one to five equivalents of the base additive. The base additive acts a scavenger for the hydrochloric acid generated during the reaction. Examples of suitable base additives for this reaction include but are not limited to sodium bicarbonate, triethylamine, sodium acetate, N-methylimidazole, pyridine, N-methylbenzimidazole and potassium carbonate. In one embodiment, the base additive is selected from sodium bicarbonate, triethylamine, sodium acetate, N-methylimidazole, pyridine and N-methylbenzimidazole. In one particular embodiment, the base additive is sodium bicarbonate. In one particular embodiment, the base additive is N-methylimidazole.

The reaction of a compound of formula (III) with a compound of formula (IV) in the presence of the base additive may conveniently be carried out in an inert solvent at ambient temperature. Examples of suitable inert solvents for this reaction include but are not limited to, chloroform, dichloromethane, tetrahydrofuran, dioxane, toluene, and mixtures of any of the foregoing with acetic acid (e.g., a mixture of chloroform and acetic acid). In one embodiment, the inert solvent is selected from dichlorommethane, chloroform, tetrahydrofuran, diethyl ether, and toluene and a mixture of any of the foregoing and acetic acid (e.g. a mixture of chloroform and acetic acid).

A compound of formula (IV) can be prepared by reacting a compound of formula (V) with sulfuryl chloride.

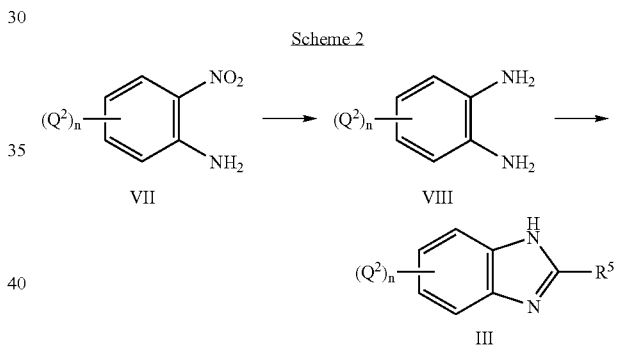

wherein all variables are as defined above.

Compounds of formula (V) are commercially available or can be prepared using conventional knowledge in the art. Typically, reaction of a compound of formula (V) with sulfuryl chloride at room temperature provides a compound of formula (IV). Excess sulfuryl chloride may be used if desired. Examples of suitable solvents include but are not limited to chloroform, dichloromethane, and toluene. See, Corral, C.; Lissavetzky, J. Synthesis 847-850 (1984).

A compound of formula (III) can be prepared by several methods. According to one method, a compound of formula (III) is prepared according to Scheme 2 below.

Scheme 2 wherein all variables are as defined in above.

Generally, this process for preparing a compound of formula (III) (all formulas and all variables having been defined above in connection with Scheme 1) comprises the steps of:
a) reducing the compound of formula (VII) to prepare a compound of formula (VIII); and
b) reacting the compound of formula (VII) with a ring forming reagent to prepare a compound of formula (III).

The order of the foregoing steps is not critical to the practice of the invention and the process may be practiced by performing the steps in any suitable order based on the knowledge of those skilled in the art.

The compound of formula (III) may be directly employed in the process of the present invention or may be converted to an acid addition salt thereof prior to use in the present invention. Methods for the conversion of a compound of formula (III) to an acid addition salt thereof are well known in the art and include, for example the methods described in Burger's Medicinal Chemistry And Drug Discovery 5th Edition, Vol 1: Principles And Practice. In one embodiment, the compound of formula (III) is converted to the acetic acid salt thereof.

More specifically, a compound of formula (III) can be prepared by reacting a compound of formula (VIII) with a ring forming reagent. There are several ring forming reagents which may be employed in this process step. In one embodiment, the compound formula (III-A) (i.e., a compound of formula (III) wherein $R^5$ is H or alkyl) is prepared by reacting a compound of formula (VIII) with a ring forming reagent of formula (IX).

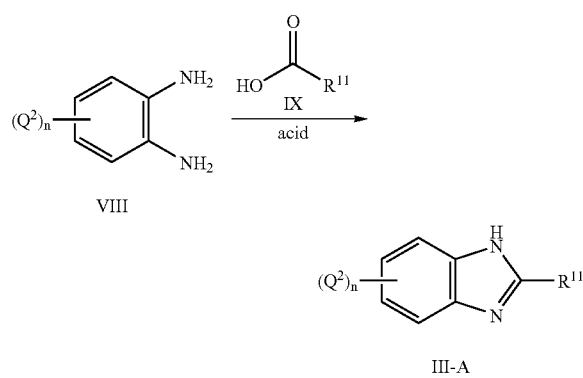

wherein $R^{11}$ is H or alkyl and all other variables are as defined above.

This reaction may be carried out using conventional techniques. See, White, A., et al., *J. Med. Chem.* 43:4084-4097 (2000); Jiang, J.-L., et al., *Synthetic Comm.* 28:4137-4142 (1998); Tanaka, A., et al., *Chem. Pharm. Bull* 42:560-569 (1994); Tian, W., et al., *Synthesis* 12:1283-1286 (1992); Buckle, D. R., et al., *J. Med. Chem.* 30:2216-2221 (1987); and Raban, M., et al., *J. Org. Chem.* 50:2205-2210 (1985). This reaction may be carried out neat or in a suitable solvent. The reaction may optionally be heated to a temperature of from about 50 to about 230° C. The reaction is typically carried out with an excess of the compound of formula (IX). An additional acid may be used. Examples of suitable acids include but are not limited to, hydrochloric acid, hydrobromic acid, perchloric acid, sulfuric acid, p-toluenesulfonic acid, methanesulfonic acid, and trifluoromethanesulfonic acid. Examples of suitable solvents for this reaction include but are not limited to water, methanol, ethanol, isopropanol, tetrahydrofuran, dichloromethane, toluene, N,N-dimethylformamide, dimethylsulfoxide, and acetonitrile. The compounds of formula (IX) are commercially available.

A compound of formula (VII) may be prepared by reducing a compound of formula (VII).

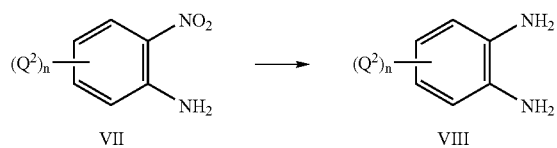

wherein all variables are as defined above.

The reduction can be carried out using conventional techniques and reducing agents. See, Rangarajan, M., et al., *Bioorg. Med. Chem.* 8:2591-2600 (2000); White, A. W., et al., *J. Med. Chem.* 43: 4084-4097 (2000); Silvestri, R., et al., *Bioorg. Med. Chem.* 8:2305-2309 (2000); Nagaraja, D., et al., *Tetrahedron Lett* 40:7855-7856 (1999); Jung, F., et al., *J. Med. Chem.* 34:1110-1116 (1991); Srivastava, R. P., et al., *Pharmazie* 45:34-37 (1990); Hankovszky, H. O., et al., *Can. J. Chem.* 67:1392-1400 (1989); Ladd, D. L., et al., *J. Org. Chem.* 53:417-420 (1988); Mertens, A., et al., *J. Med. Chem.* 30:1279-1287 (1987); and Sharma, K. S., et al., *Synthesis* 4:316-318 (1981). Examples of suitable reducing agents for this reaction include but are not limited to, palladium with hydrogen, palladium with ammonium formate, platinum oxide with hydrogen, nickel with hydrogen, tin(II) chloride, iron with acetic acid, aluminum with ammonium chloride, borane, sodium dithionite, and hydrazine. The reaction may optionally be heated to between about 50 and about 120° C. Suitable solvents for this reaction vary and include but are not limited to, water, methanol, ethanol, ethyl acetate, tetrahydrofuran, and dioxane.

A compound of formula (VII) may be prepared by several methods. In one embodiment, the compound of formula (VII) is prepared by reacting a compound of formula (VI) with ammonia.

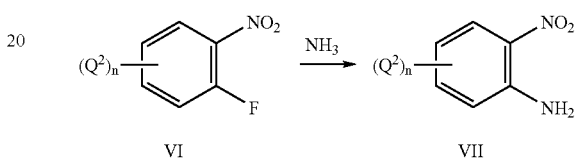

wherein all variables are as defined above.

This reaction may be carried out using conventional techniques. See, Silvestri, R., et al., *Bioorg. Med. Chem.* 8:2305-2309 (2000); Hankovszky, H. O., et al., *Can. J. Chem.* 67:1392-1400 (1989); Nasielski-Hinkens, R.; et al., *Heterocycles* 26:2433-2442 (1987); Chu, K. Y., et al., *J. Chem. Soc., Perkin Trans.* 110:1194-1198 (1978). This reaction is typically carried out with an excess of ammonia and may be optionally heated to a temperature of from about 50 to about 100° C. Examples of suitable solvents for this reaction include but are not limited to, water, methanol, ethanol, isopropanol, tetrahydrofuran, dioxane, and 1,2-dimethoxyethane.

The compounds of formula (VI) are commercially available or may be prepared using conventional techniques and reagents.

In another embodiment, the compound of formula (VII) can be prepared by reacting a protected compound of formula (X) under nitration conditions to prepare a protected compound of formula (VII) (i.e., VII-A) and then removing the protecting group from the compound of formula (VII-A).

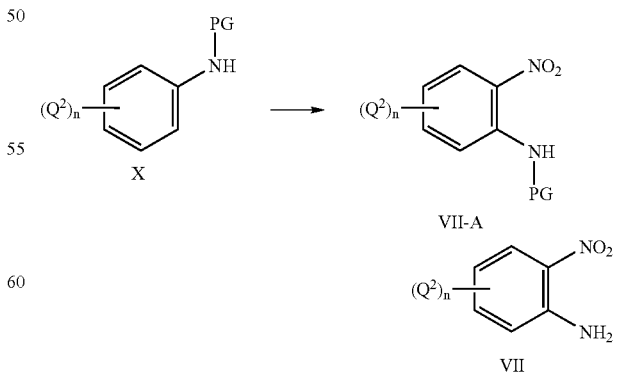

wherein PG is a protecting group and all other variables are as defined above.

The protection of anilines is a common transformation well known to one skilled in the art. See, Kocienski, P. J. *Protecting Groups*, Georg Thieme Verlag, Stuttgart, 1994; and Greene, T. W., Wuts, P. G. M. *Protecting Groups in Organic Synthesis* (2nd Edition), J. Wiley and Sons, 1991. Suitable protecting groups for this application include but are not limited to acetyl, trifluoroacetyl, benzyloxycarbonyl, allyloxycarbonyl, 2-(rimethylsilyl)ethoxycarbonyl, phenylsulfonyl, and p-toluenesulfonyl. Reagents and conditions vary according to the nature of the particular protecting group. Some typical reagents include but are not limited to acetic anhydride, trifluoroacetic anhydride, benzyl chloroformate, allyl chloroformate, 4-nitrophenyl 2-(trimethylsilyl)ethyl carbonate, phenylsulfonyl chloride, and p-toluensulfonyl chloride. In certain cases the addition of some base is required. Examples of suitable bases include but are not limited to potassium carbonate, sodium carbonate, trialkylamines, pyridine, and potassium t-butoxide. Suitable solvents for these conversions include but are not limited to dichloromethane, chloroform, tetrahydrofuran, acetic acid, methanol, ethanol, water, toluene, and diethyl ether.

The nitration of anilines is also well documented in the literature and the foregoing reaction may be carried out using these conventional techniques. See, Wissner, A., et. al., *J. Med. Chem.* 46: 49-63 (2003); Duggan, S. A., et. al., *J. Org. Chem.* 66: 4419-4426 (2001); Clews, J., et. al., *Tetrahedron* 56: 8735-8746 (2000); and Kagechika, H., *J. Med. Chem.* 31: 2182-2192 (1988). The nitration may be carried out with a variety of nitrating reagents including but not limited to 70% aqueous nitric acid, red fuming nitric acid, ammonium nitrate with trifluoroacetic anhydride, and potassium nitrate with trifluoromethanesulfonic acid. The reaction is typically conducted at room temperature, but may be optionally heated to a temperature of from about 40 to about 100° C. in certain cases. Suitable solvents include but are not limited to acetic acid, sulfuric acid, acetic anhydride, dichloromethane, and chloroform.

The nitration results in a compound of formula (VII-A), (i.e., a protected compound of formula (VII)). The cleavage of the aniline protecting group, to result in a compound of formula (VII) can be accomplished through many different conventional methods. See, Kocienski, P. J. *Protecting Groups*, Georg Thieme Verlag, Stuttgart, 1994; and Greene, T. W., Wuts, P. G. M. *Protecting Groups in Organic Synthesis* (2nd Edition), J. Wiley and Sons, 1991.

The compounds of formula (X) may be prepared by installing a protecting group on the corresponding aniline. Such Anilines are commercially available or may be prepared using conventional techniques.

A compound of formula (III-A) may optionally be converted to a compound of formula (III-B). This conversion may be effected by halogenating the compound of formula (III-A) to prepare a compound of formula (III-B).

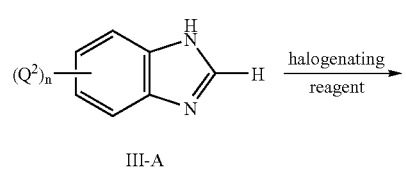

III-A

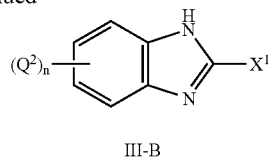

III-B wherein $X^1$ is halo (particularly Cl, Br or I) and all other variables are as defined above.

This type of transformation is well established in the literature. See, Taylor, E. C., et al., *J. Org. Chem.* 56:6937-6939 (1991); Mistry, A. G., et al., *Tetrahedron Lett.* 27:1051-1054 (1986); and Apen, P. G., et al., *Heterocycles* 29:1325-1329 (1989). Suitable halogenating agents include but are not limited to, N-chlorosuccinimide, N-bromosuccinimide, N-iodosuccinimide, chlorine, bromine, and iodine. Examples of suitable solvents include but are not limited to, dichloromethane, chloroform, diethyl ether, tetrahydrofuran, and acetone.

A compound of formula (III-B) may also be prepared directly from a compound of formula (VIII). The process comprises the steps of i) reacting a compound of formula (VIII) with a phosgene or phosgene equivalent compound to prepare a compound of formula (XII) and ii) reacting the compound of formula (XII) with phosphorous oxy halide to prepare a compound of formula (III-B).

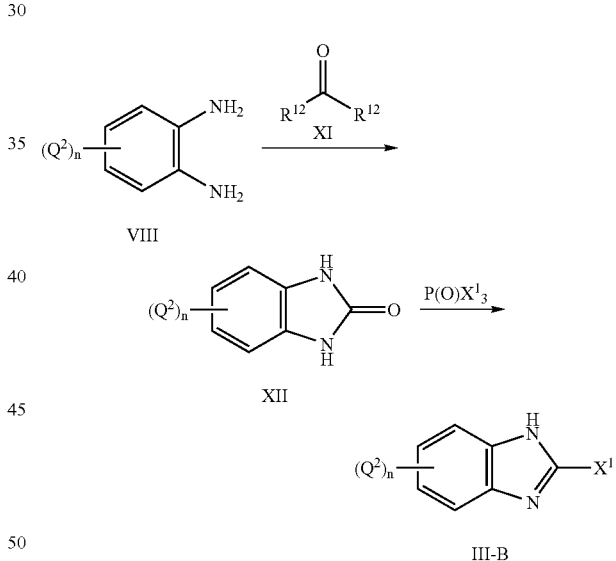

wherein:

each $R^{12}$ is the same or different and is independently selected from the group consisting of Cl, methoxy, ethoxy, trichloromethoxy, amino and N-imidazolyl;

$X^1$ is halo (particularly Cl, Br or I; more particularly Cl or Br); and all other variables are as defined above.

The phosgene or phosgene equivalent compound is the ring forming reagent and is typically a compound of formula (XI) as shown above. Phosgene and phosgene equivalent compounds of formula (XI) are commercially available. Examples of suitable compounds of formula (XI) include but are not limited to phosgene, dimethyl carbonate, diethyl carbonate, 1,1'-carbonyldiimidazole, urea, and triphosgene. The reaction of a compound of formula (VIII) with the phosgene or phosgene equivalent compound can be carried out using conventional techniques. See, Silvestri, R., et al., *Bioorg. Med. Chem.* 8:2305-2309 (2000); Wright, J. L., et al., *J. Med. Chem.* 43:3408-3419 (2000); Penieres, G. C., et al., *Synthetic Comm.* 30:2191-2195 (2000); and Von der Saal, W., et al., *J. Med. Chem.* 32:1481-1491 (1989). The reaction is typically run in an inert solvent or neat. The reaction may be optionally heated to a temperature of from about 50 to about 250° C. The optional addition of a suitable base to the reaction may be desirable. Examples of such bases include but are not limited to, trialkylamines, pyridine, 2,6-lutidine, potassium carbonate, sodium carbonate, and sodium bicarbonate. Examples of suitable solvents for this reaction include but are not limited to dichloromethane, chloroform, N,N-dimethylformamide, tetrahydrofuran, toluene, and acetone.

The reaction of the compound of formula (XII) with the phosphorous oxy halide to prepare a compound of formula (III-B) can be carried out using conventional techniques. See, Blythin, D. J., et al., *J. Med. Chem.* 29:1099-1113 (1986); and Crank, G., *Aust J. Chem.* 35:775-784 (1982). Examples of suitable reagents include but are not limited to phosphorous oxychloride and phosphorous oxybromide. Suitable solvents include but are not limited to, dichloromethane, chloroform, dichloroethane, and toluene. Optional heat ranging from about 50 to about 150° C. may be used.

A compound of formula (III-B), prepared by any method, may optionally be converted to a compound of formula (III-C) by reacting with an amine of formula $HNR^7R^8$.

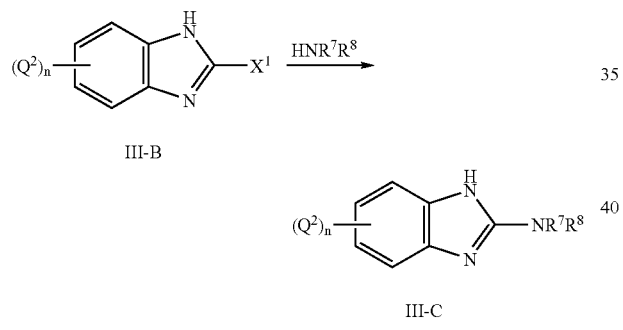

III-B

III-C wherein all variables are as defined above.

The reaction of a halo-substituted benzimidazole of formula (III-B) with an amine to prepare a compound of formula (III-C) can be carried out using conventional techniques. See, Alcalde, E., et al., *J. Org. Chem.* 56:4233-4238 (1991); Katsushima, T., et al., *J. Med. Chem.* 33:1906-1910 (1990); Young, R. C., et al., *J. Med. Chem.* 33:2073-2080 (1990); Iemura, R., et al., *J. Med. Chem.* 29:1178-1183 (1986); and Benassi, R., et al., *J. Chem. Soc., Perkin Trans.* 2 10:1513-1521 (1985). An acid catalyst may be employed if desired. Examples of suitable acid catalysts include but are not limited to, hydrochloric acid and p-toluenesulfonic acid. The reaction can optionally be heated to a temperature of from about 50 to about 220° C. Suitable solvents for this reaction include but are not limited to, water, ethanol, isopropanol, 1-methyl-2-pyrrolidinone, N,N-dimethylformamide, dimethylsulfoxide, toluene, xylenes and tetrahydrofuran.

In another embodiment, a compound of formula (III-D) (i.e., a compound of formula ((III) wherein $R^5$ is H or alkyl) is prepared according to the process outlined in Scheme 3 below.

Scheme 3

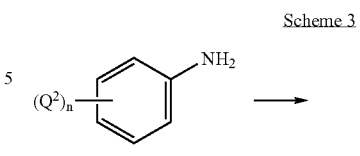

XIII

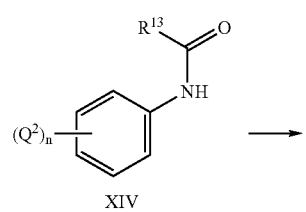

XIV

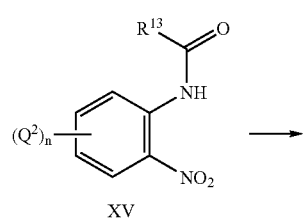

XV

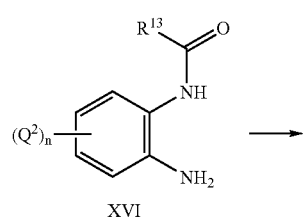

XVI

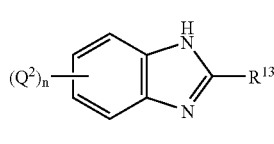

III-D wherein $R^{13}$ is H or alkyl and all other variables are as defined above.

Generally, this process for preparing the a compound of formula (III-D) (all formulas and all variables having been defined above in connection with Scheme 1) comprises the steps of:

a) reacting a compound of formula (XIII) with a suitable acylating agent to prepare a compound of the formula (XIV);

b) reacting a compound of formula (XIV) under nitration conditions to prepare a compound of the formula (XV);

c) reducing a compound of formula (XV) to prepare a compound of formula (XVI); and d) cyclizing a compound of formula (XVI) to prepare a compound of formula (III-D).

The order of the foregoing steps is not critical to the practice of the invention and the process may be practiced by performing the steps in any suitable order based on the knowledge of those skilled in the art.

More specifically, a compound of formula (III-D) can be prepared by cyclizing a compound of formula (XVI).

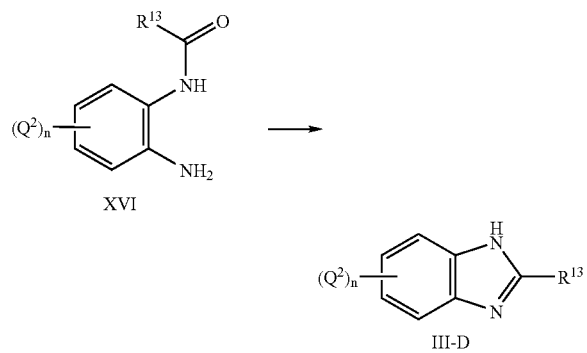

wherein all variables are as defined above.

This type of cyclization reaction is well documented in the literature. See, Braña, M. F., et. al., *J. Med. Chem.* 45: 5813-5816 (2002); Fonseca, T., et. al., *Tetrahedron* 57: 1793-1799 (2001); White, A. W., et. al., *J. Med. Chem.* 43: 4084-4097 (2000); and Tamura, S. Y., et. al., *Biorg. Med. Chem. Lett.* 7: 1359-1364 (1997). This reaction may be carried out neat or in a suitable solvent. The reaction may optionally be heated to a temperature of from about 50 to about 200° C. Typically an excess of a suitable acid is used. Examples of suitable acids include but are not limited to acetic acid, trifluoroacetic acid, hydrochloric acid, hydrobromic acid, sulfuric acid, methanesulfonic acid, p-toluenesulfonic acid, and pyridinium p-toluenesulfonate. A dehydrating reagent may optionally be used as well. Examples of suitable dehydrating reagents include but are not limited to magnesium sulfate, sodium sulfate, phosphorous pentoxide, and molecular sieves. Examples of suitable solvents include but are not limited to dichloromethane, chloroform, toluene, xylenes, methanol, ethanol, and water.

A compound of formula (XVI) may be prepared by reducing a compound of formula (XV).

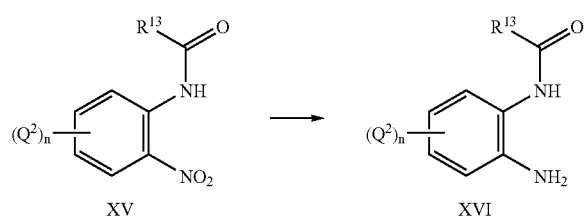

wherein all variables are as defined above.

The reduction can be carried out using conventional techniques and reducing agents. See, Rangarajan, M., et al., *Bioorg. Med. Chem.* 8:2591-2600 (2000); White, A. W., et al., *J. Med. Chem.* 43:4084-4097 (2000); Silvestri, R., et al., *Bioorg. Med. Chem.* 8:2305-2309 (2000); Nagaraja, D., et al., *Tetrahedron Lett.* 40:7855-7856 (1999); Jung, F., et al., *J. Med. Chem.* 34:1110-1116 (1991); Srivastava, R. P., et al., *Pharmazie* 45:34-37 (1990); Hankovszky, H. O., et al., *Can. J. Chem.* 67:1392-1400 (1989); Ladd, D. L., et al., *J. Org. Chem.* 53:417-420 (1988); Mertens, A., et al., *J. Med. Chem.* 30:1279-1287 (1987); and Sharma, K. S., et al., *Synthesis* 4:316-318 (1981). Examples of suitable reducing agents for this reaction include but are not limited to, palladium with hydrogen, palladium with ammonium formate, platinum oxide with hydrogen, nickel with hydrogen, tin(II) chloride, iron with acetic acid, aluminum with ammonium chloride, borane, sodium dithionite, and hydrazine. The reaction may optionally be heated to between about 50 and about 120° C. Suitable solvents for this reaction vary and include but are not limited to, water, methanol, ethanol, ethyl acetate, tetrahydrofuran, and dioxane.

A compound of formula (XV) may be prepared by reacting a compound of formula (XIV) under nitration conditions.

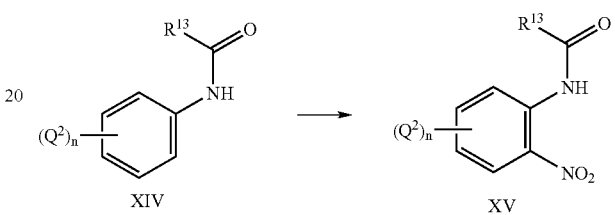

wherein all variables are as defined above.

The reaction of the compound of formula (XIV) under nitration conditions may be carried out in the same manner as described above for the nitration of a compound of formula (X).

A compound of formula (XIV) may be prepared by acylating a compound of formula (XIII).

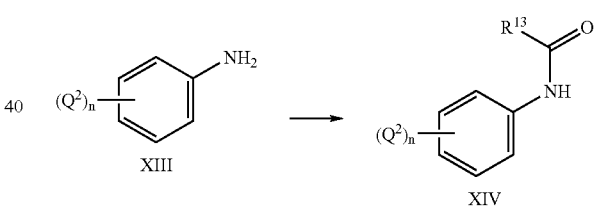

wherein all variables are as defined above.

Acylation of anilines is a common transformation well known to one skilled in the art and such conventional acylation techniques may be employed for carrying out the foregoing reaction. See, Larock, R. C. *Comprehensive Organic Transformations*, VCH Publishers, Inc., New York, pp. 972-976, 979, 981 (1989). The acylation reaction is typically carried out using an acylating agent such as an acid halide, acid anhydride, or carboxylic acid, in the presence of a coupling reagent(s). Examples of suitable coupling reagents include but are not limited to N,N-dicyclohexylcarbodiimide, 1-(3-dimethylaminopropyl)-3-ethylcarbodiimide hydrochloride, O-(7-azabenzotriazol-1-yl)-N,N,N'N'-tetramethyluronium hexafluorophosphate, and N,N'-carbonyldiimidazole. Suitable solvents include but are not limited to N,N-dimethylformamide, tetrahydrofuran, dioxane, toluene, benzene, 1,2-dimethoxyethane, and 1-methyl-2-pyrrolidinone. Anilines of formula (XIII) are commercially available or readily prepared from commercially available material using conventional techniques.

The present invention may optionally include the further step of converting the compound of formula (I) to a pharmaceutically acceptable salt, solvate or physiologically functional derivative thereof. Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, a compound of formula (I) may be converted to a different compound of formula (I) using techniques well known in the art. For example, a compound of formula (I-A) may optionally be converted to a compound of formula (I-B) or (I-C) according to the process outlined in Scheme 4.

compound of formula (XVIII). The compounds of formula (XVIII) are commercially available or can be prepared using conventional knowledge in the art. The reaction may be carried out in an inert solvent, conveniently at room temperature, in the presence of a suitable base. The compound of formula (I-A) and the compound of formula (XVIII) may be present in equimolar amounts; however, a slight excess of the compound of formula (XVIII) may be employed if desired. Examples of suitable bases for this reaction include but are not limited to, potassium carbonate, sodium carbonate, cesium carbonate, sodium hydride, and potassium hydride. Examples of suitable inert solvents for this reaction include but are not limited to, N,N-dimethylformamide, tetrahydrofuran, dioxane, and 1,2-dimethoxyethane.

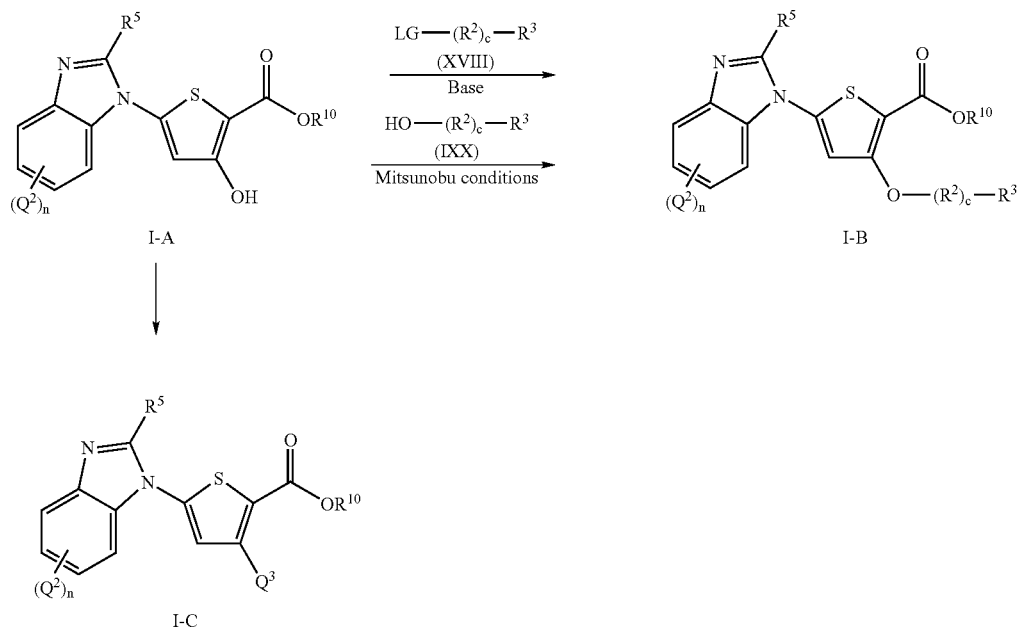

wherein
Q$^3$ is a group of formula: —(R$^2$)$_a$—(Y$^3$)$_j$—(R$^2$)$_c$—R$^3$
j is 0 or 1;
Y$^3$ is selected from the group consisting of —S(O)$_f$—, —N(R$^7$)—, —C(O)—, —OC(O)—, —CO$_2$—, —C(O)N(R$^7$)—, —C(O)N(R$^7$)S(O)$_2$—, —OC(O)N(R$^7$)—, —OS(O)$_2$—, —S(O)$_2$N(R$^7$)—, —S(O)$_2$N(R$^7$)C(O)—, —N(R$^7$)S(O)$_2$—, —N(R$^7$)C(O)—, —N(R$^7$)CO$_2$— and —N(R$^7$)C(O)N(R$^7$)—;
LG is a suitable leaving group; and
all other variables are as defined above.

In general the process for preparing a compound of formula (I-B) comprises the steps of:
a) reacting the compound of formula (I-A) with a base and a compound of formula (XVIII) to prepare a compound of the formula (I-B); or
b) reacting the compound of formula (I-A) with a compound of formula (IXX) under Mitsunobu conditions to prepare a compound of formula (I-B).

More specifically, a compound of formula (I-B) can be prepared by reacting a compound of formula (I-A) with a In another embodiment, a compound of formula (I-B) can be prepared by reacting a compound of formula (I-A) with a compound of formula (IXX). The compounds of formula (IXX) are commercially available or can be prepared using conventional knowledge in the art. The reaction is carried out in an inert solvent under standard Mitsunobu conditions. See, Hughes, D. L., Org. React. 42:335-656 (1992); and Mitsunobu, O., Synthesis 1-28 (1981). Typically the compound of formula (I-A), the compound of formula (IXX), a triarylphosphine, and a dialkyl azodicarboxylate are reacted together at room temperature. Examples of suitable triarylphosphines include but are not limited to, triphenylphosphine, tri-p-tolylphosphine, and trimesitylphosphine. Examples of suitable dialkyl azodicarboxylates include but are not limited to, diethyl azodicarboxylate, diisopropyl azodicarboxylate, and di-tert-butyl azodicarboxylate. Examples of suitable inert solvents for this reaction include but are not limited to, tetrahydrofuran, dioxane, 1,2-dimethoxyethane, dichloromethane, and toluene.

A compound of formula (I-A) may also be converted to a compound of formula (I-C) according to the following Scheme 5.

Scheme 5

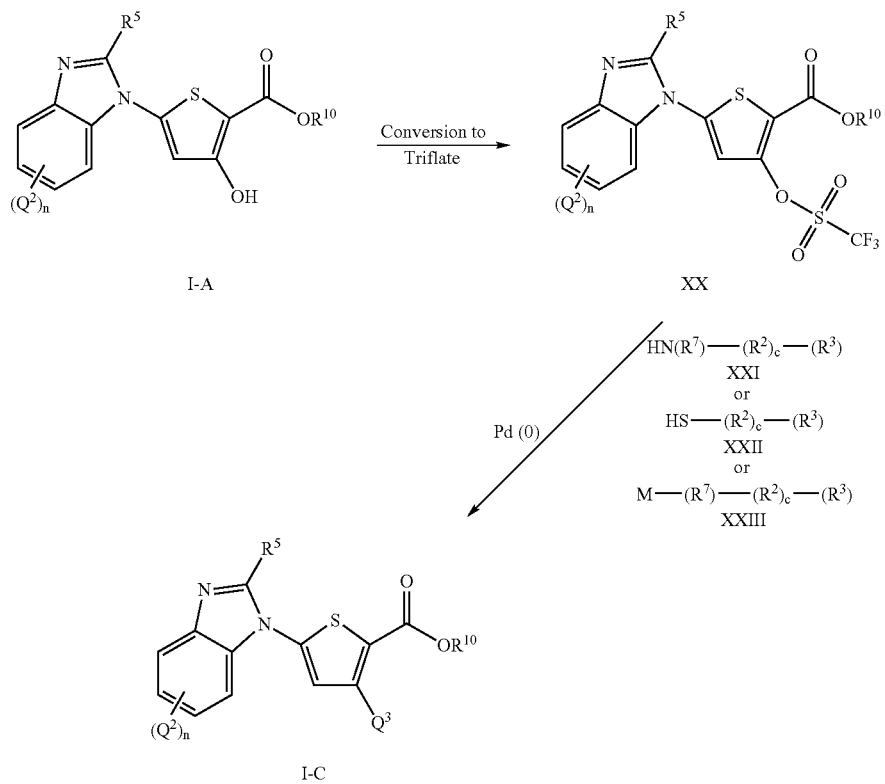

wherein M is —B(OH)$_2$, —B(OR$^{14}$)$_2$, —Sn(R$^{14}$)$_2$, Zn-halo, Zn—R$^{14}$, Mg-halo, Cu-halo, Cu—R$^{14}$ where R$^{14}$ is alkyl or cycloalkyl, and all other variables are as defined above.

Generally, the process for preparing a compound of formula (I-C) comprises the steps of:

a) reacting a compound of formula (I-A) with a suitable triflating reagent to prepare a compound of formula (XX); and b) coupling the compound of formula (XX) with a compound selected from the group consisting of a compound of formula (XXI), (XXII), and (XXIII) using a palladium (0) catalyst to prepare a compound of the formula (I-C).

More specifically, a compound of formula (I-C) can be prepared by reacting a compound of formula (XX) with a compound selected from the group consisting of a compound of formula (XXI), (XXII), and (XXIII) using a palladium (0) catalyst. This reaction may be carried out in an inert solvent, in the presence of palladium (0). The reaction may optionally be heated to a temperature of from about 50 to about 150° C. Typically, the reaction is carried out by reacting an equimolar amount of a compound of formula (XX) with an equimolar amount of the compound selected from the group consisting of compounds of formula (XXI), (XXII) and (XXIII). The palladium (0) catalyst is typically present in 1-10 mole percent compared to the compound of formula (XX). Examples of suitable palladium catalysts include but are not limited to, tetrakis(triphenylphosphine)palladium (0) and tris(dibenzylideneacetone)dipalladium (0). It is also possible to generate the palladium (0) catalyst in situ using palladium (II) sources. Examples of suitable palladium (II) sources include but are not limited to, palladium (II) acetate, palladium (II) chloride, palladium (II) trifluoroacetate, dichlorobis(triphenyl-phosphine)palladium (II), and bis(diphenylphosphino-ferrocene)palladium (II) dichloride. Suitable solvents for this reaction include but are not limited to N,N-dimethylformamide, tetrahydrofuran, dioxane, toluene, benzene, 1,2-dimethoxyethane, and 1-methyl-2-pyrrolidinone. Bases and phosphines may be included as additives in the reaction if desired. Examples of suitable bases include but are not limited to cesium carbonate, sodium carbonate, and trialkylamines. Examples of suitable phosphine additives include but are not limited to triphenylphosphine, tributylphosphine, diphenylphosphinoethane, and 2,2'-bis(diphenylphosphino)-1,1'-binaphthyl. Compounds of the formula (XXI), (XXII) and (XXIII) may be obtained from commercial sources or prepared either as discreet compounds or generated in situ using conventional knowledge in the art. See, Luker, T. J., et al., *Tetrahedron Lett* 41:7731-7735 (2000); Yin, J., et al., *Org. Lett.* 2:1101-1104 (2000); Wolfe, J. P., et al., *Can. J. Chem.* 78:957-962 (2000); Littke, A. F., et al., *J. Am. Chem. Soc.* 122:4020-4028 (2000); Hundertmark, T., et al., *Org. Lett.* 2:1729-1731 (2000); Buchwald, S. L., *Acc. Chem. Res.* 31:805-818 (1998); Suzuki, A., *J. Organomet Chem.* 576: 147-168 (1999); Negishi, E., *J. Organomet Chem.* 576:179-194 (1999); Stanforth, S. P., *Tetrahedron* 54:263-303 (1998); Littke, A. F., *Angew. Chem., Int. Ed.* 37:3387-3388 (1999); and Thorand, S., et al., *J. Org. Chem.* 63:8551-8553 (1998).

A compound of formula (XX) can be prepared from a compound of formula (I-A) using a suitable treating reagent. This reaction is typically carried out in an inert solvent using a base and a reagent designed for conversion of alcohols into triflates (i.e., a triflating reagent). Examples of suitable bases include but are not limited to sodium carbonate, trialkylamines, pyridine, sodium hydride, and lithium bis(trimethylsilyl)amide. The reaction is preferably run at a temperature of from about 0 to about 25° C. Suitable triflating reagents for this reaction include but are not limited to, trifluoromethanesulfonic anhydride, trifluoromethanesulfonyl chloride, and N-phenyltrifluoromethanesulfonimide. Suitable inert solvents for this reaction include but are not limited to tetrahydrofuran, dichloromethane, toluene, chloroform, diethyl ether, and dioxane.

As a further example of methods for converting a compound of formula (I) to another compound of formula (I), a compound of formula (I-A), (I-B), or (I-C) (collectively referred to as a compound of formula "(I-D)" may be converted to a different compound of formula (I)

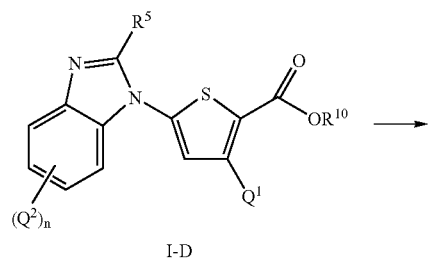

I-D

-continued

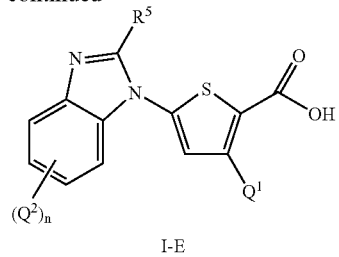

I-E wherein all variables are as defined above.

There are several options for carrying out this conversion. Examples of suitable conditions include but are not limited to, basic hydrolysis where $R^1$ is —$CO_2Me$, deprotection with protic acid where $R^1$ is —$CO_2t$-Bu, deprotection under palladium (0) catalysis where $R^1$ is $CO_2CH_2CH=CH_2$, deprotection with tetrabutylammonium fluoride where $R^1$ is $CO_2CH_2CH_2Si(CH_3)_3$, and hydrogenolysis where $R^1$ is $CO_2CH_2Ph$. Other suitable conditions for compounds with various $R^{10}$ definitions will be apparent to those skilled in the art. The choice of protecting group and deprotection conditions will be apparent to one skilled in the art and, detailed information on this subject is available in the literature. See, Kocienski, P. J. *Protecting Groups*, Georg Thieme Verlag, Stuttgart, 1994; and Greene, T. W., Wuts, P. G. M. *Protecting Groups in Organic Synthesis* ($2^{nd}$ Edition), J. Wiley and Sons, 1991.

A compound of formula (I-E) may be further converted to a compound of formula (I-F) by heating.

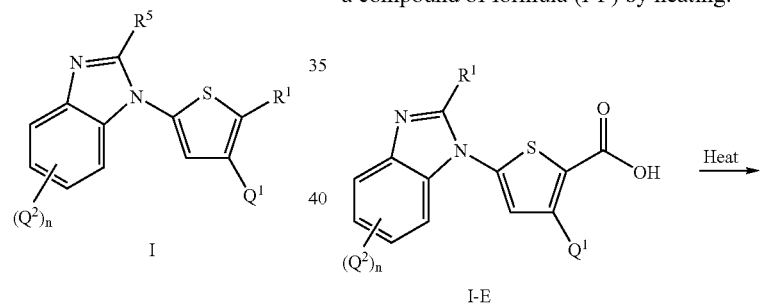

I wherein:

$R^1$ is other than —$CO_2R^{10}$;

and all other variables are as defined above.

Several methods, using conventional techniques can be employed to convert a compound of formula (I-D) to a different compound of formula (I), depending upon the particular compound of formula (I) that is desired. For example, according to one method, a compound of formula (I-D) can be converted to a compound of formula (I-E) by removal of the carboxylic acid protecting group.

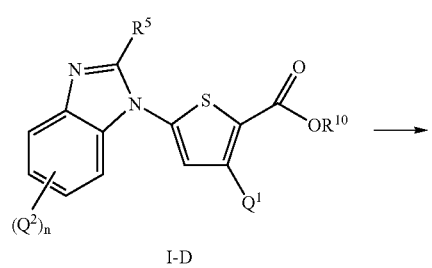

I-D

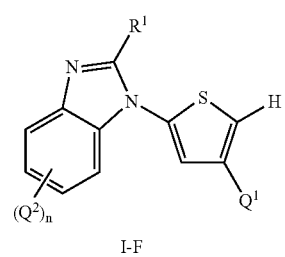

I-F wherein all variables are as defined above.

This reaction may be performed in an inert solvent. Typically, the reaction is heated to a temperature of from about 80 to about 120° C. Examples of suitable solvents for this reaction include but are not limited to acetic acid, propionic acid, N,N-dimethylformamide, dimethylsulfoxide, ethanol, dioxane and toluene.

A compound of formula (I-E) may be further converted to a compound of formula (I-G) using conventional amide bond coupling reactions with an amine of formula HNR⁷R⁸.

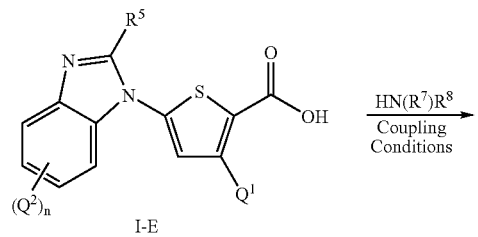

I-E

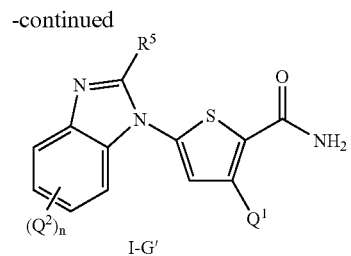

I-G' wherein all variables are as defined above.

This reaction is typically performed in a sealed vessel with an excess of ammonia. The reaction is typically heated to a temperature of from about 50 to about 120° C. Suitable solvents for this reaction include but are not limited to methanol, ethanol, isopropanol, tetrahydrofuran, and dioxane.

Dehydration of the compound of formula (I-G') may be used to prepare a compound of formula (I-H).

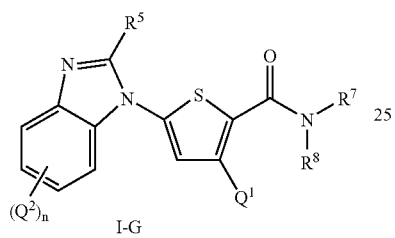

I-G wherein all variables are as defined above.

This reaction can be carried out in an inert solvent using a variety of commercially available coupling reagents. Suitable coupling reagents include but are not limited to N,N-dicyclohexylcarbodiimide, 1-(3-dimethylaminopropyl)-3-ethylcarbodiimide hydrochloride, 1,1'-carbonyldiimidazole, and benzotriazol-1-yloxytris(dimethyl-amino)phosphonium hexafluorophosphate. Other suitable coupling reagents will be readily apparent to those skilled in the art. The carboxylic acid optionally may be converted into the corresponding acid chloride and subsequently treated with the amine of formula HNR⁷R⁸. Suitable reagents for the reaction of such acid chlorides include but are not limited to oxalyl chloride, thionyl chloride, and 1-chloro-N,N,2-trimethyl-1-propenylamine. Base may be optionally added to the coupling reaction. The reaction may optionally require heating to a temperature of from about 40 to about 100° C. Suitable bases include but are not limited to trialkylamines, pyridine, and 4-(dimethylamino)pyridine. Examples of suitable solvents for this reaction include but are not limited to dichloromethane, chloroform, benzene, toluene, N,N-dimethylformamide and dichloroethane.

In an alternative embodiment, a compound of formula (I-G') is prepared directly from a compound of formula (I-D).

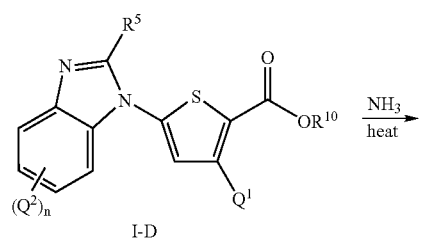

I-D

I-G' wherein all variables are as defined above.

The dehydration reaction can be carried out using a variety of reagents. Suitable dehydration reagents include but are not limited to thionyl chloride, trifluoroacetic anhydride, phosphorous oxychloride, phosphorous pentoxide, and N,N-dicyclohexyl-carbodiimide. The reaction may be optionally heated to from about 50 to about 150° C. Suitable solvents for this reaction include but are not limited to dichloromethane, chloroform, benzene, toluene, N,N-dimethylformamide, and dichloroethane.

A compound of formula (I-J) may be prepared through a two step conversion process, comprising a) converting a compound of formula (I-E) to a compound of formula (I-I) by coupling with N,O-dimethylhydroxylamine, and b) reacting the compound of formula (I-I) with a nucleophile of formula $M^1$-$R^7$.

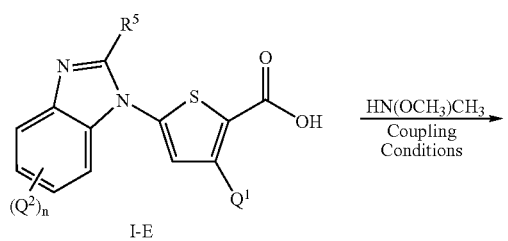
I-E

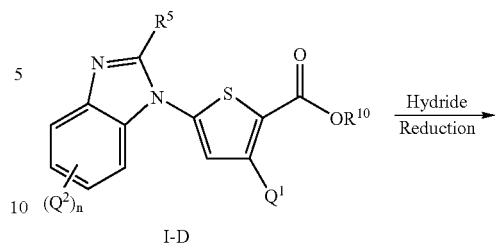
I-D

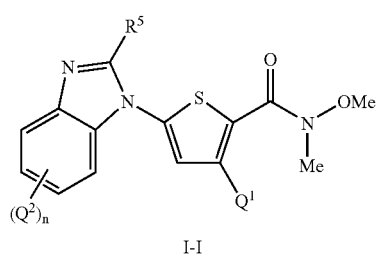
I-I

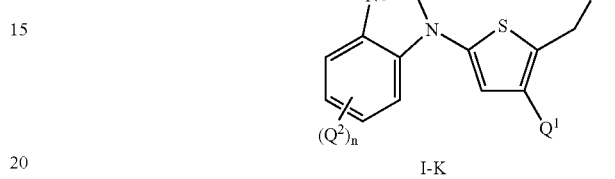

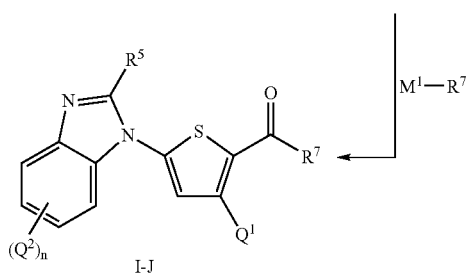
I-J

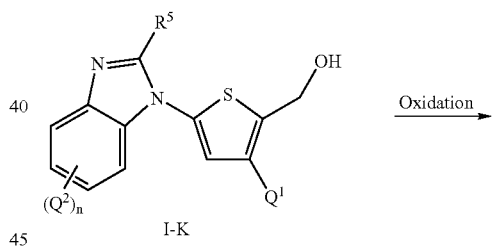
I-K wherein all variables are as defined above.

This reaction may be carried out in an inert solvent at a temperature ranging from about −78 to about 25° C. Suitable reducing agents include but are not limited to diisobutylaluminum hydride, lithium aluminum hydride, and lithium borohydride. Suitable solvents vary considerably depending on the chosen reducing agent. Appropriate selection of a solvent for this reaction will be apparent to those skilled in the art based upon the choice of reducing agent. Examples of suitable solvents include but are not limited to tetrahydrofuran, diethyl ether, 1,2-dimethoxyethane, dioxane, dichloromethane, toluene, and hexanes.

A compound of formula (I-K) may be oxidized to prepare a compound of formula (I-L).

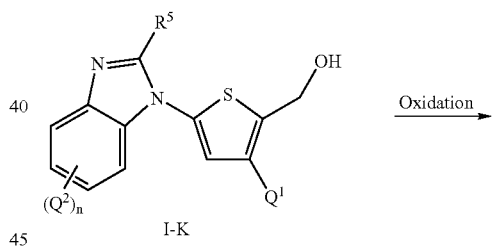
I-K

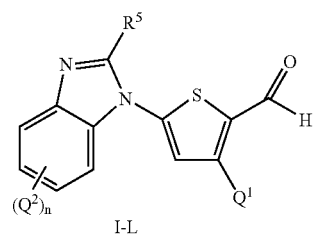
I-L wherein all variables are as defined above.

This reaction can be carried out using a wide variety of conventional oxidizing agents. Suitable oxidizing agents include but are not limited to, manganese dioxide, dimethyl sulfoxide/oxalyl chloride/triethylamine, pyridinium chlorochromate, pyridinium dichromate, and tetrapropylammonium perruthenate/4-methylmorpholine N-oxide. Examples of suitable solvents for the oxidation reaction include but are not limited to, dichloromethane, chloroform, diethyl ether, toluene, and tetrahydrofuran.

wherein $M^1$ is Li, Mg-halo, Cu-halo or Ce-halo; and all variables are as defined above.

The coupling reaction with N,O-dimethylhydroxylamine may be carried out in the same manner as described above for the conversion of a compound of formula (I-E) to a compound of formula (I-G). The addition of the nucleophile to the Weinreb amide (I-I) is typically carried out at a temperature ranging from about −30 to about 5° C. Suitable solvents for this reaction include but are not limited to, tetrahydrofuran, dioxane, diethyl ether, toluene, 1,2-dimethoxyethane, and hexanes. See, Weinreb, S. M., et al., *Tetrahedron Lett.* 22:3815-3818 (1981). Nucleophiles of formula $M^1$-$R^7$ are commercially available or can be prepared using conventional knowledge in the art.

A compound of formula (I-K) may be prepared from a compound of formula (I-D) through a hydride reduction.

A compound of formula (I-L) may be further converted to a compound of formula (I-M) by reacting with a nucleophile of formula $M^1$-$R^7$.

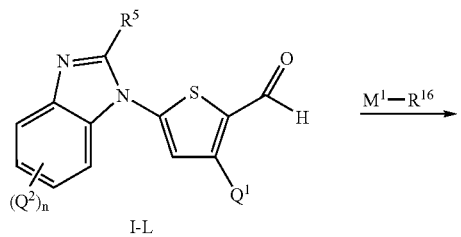

I-L

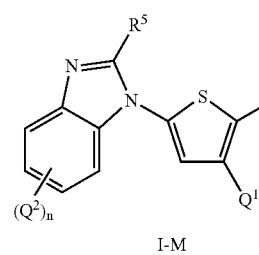

I-M wherein $M^1$ is Li, Mg-halo, Cu-halo or Ce-halo,
$R^{16}$ is H, alkyl, alkenyl or alkynyl; and
all other variables are as defined above.

The addition of the nucleophile $M^1$-$R^{16}$ to the aldehyde of formula (I-L) is typically carried out at a temperature ranging from about −78 to about 5° C. Suitable solvents for this reaction include but are not limited to, tetrahydrofuran, dioxane, diethyl ether, toluene, 1,2-dimethoxyethane, and hexanes.

As an alternative to the previously described method, a compound of the formula (I-J) may also be prepared by conversion from a compound of formula (I-M). More specifically, a compound of formula (I-J) may be prepared by oxidation of a compound of formula (I-M).

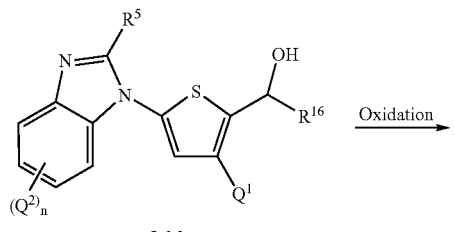

I-M

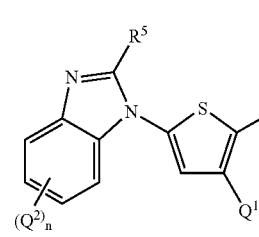

I-J wherein $R^{16}$ is H, alkyl, alkenyl or alkynyl; and
all other variables are as defined above.

This reaction can be carried out using a wide variety of conventional oxidizing agents. Examples of suitable oxidizing agents include but are not limited to, manganese dioxide, dimethyl sulfoxide/oxalyl chloride/triethylamine, pyridinium chlorochromate, pyridinium dichromate, and tetrapropylammonium perruthenate/4-methylmorpholine N-oxide. Suitable solvents for this reaction include but are not limited to, dichloromethane, chloroform, diethyl ether, toluene and tetrahydrofuran.

Further, a compound of formula (I-J) may be converted to a compound of formula (I-M') by reacting with a nucleophile of formula $M^1$-$R^{16}$.

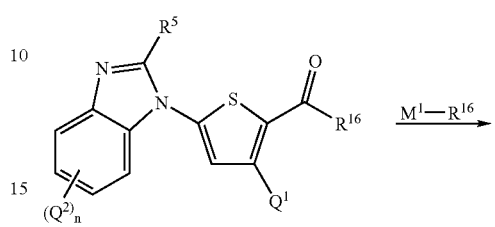

I-J

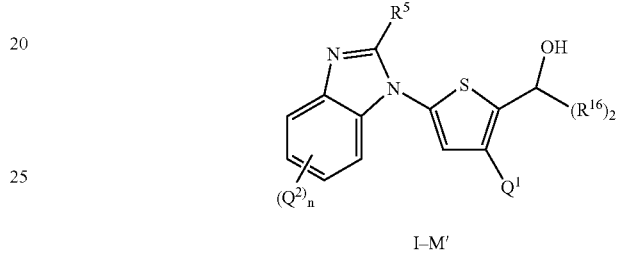

I-M' wherein $M^1$ is Li, Mg-halo, Cu-halo or Ce-halo;
$R^{16}$ is H, alkyl, alkenyl or alkynyl; and
all other variables are as defined above.

Nucleophiles of formula $M^1$-$R^{16}$ are commercially available or can be prepared using conventional knowledge in the art.

The addition of the nucleophile to the aldehyde of formula (I-J) is typically carried out at a temperature ranging from about −78 to about 5° C. Suitable solvents for this reaction include but are not limited to, tetrahydrofuran, dioxane, diethyl ether, toluene, 1,2-dimethoxyethane, and hexanes.

A compound of formula (I-M) may be further converted to a compound of formula (I-N) by halogenating the compound of formula (I-M).

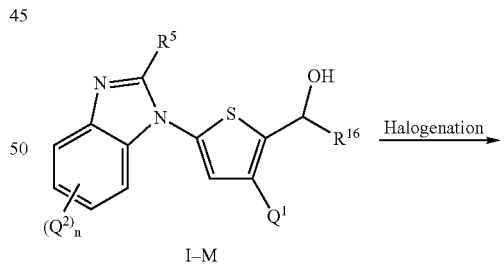

I-M

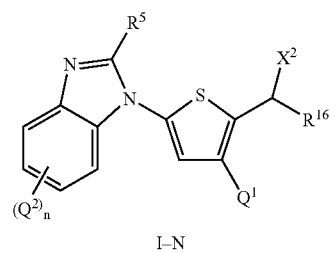

I-N wherein $X^2$ is halo;

$R^{16}$ is H, alkyl, alkenyl or alkynyl; and all other variables are as defined above.

This reaction may be carried out using any conventional halogenating reagent. Examples of suitable halogenating reagents include but are not limited to triphenylphosphine/iodine/imidazole, triphenylphosphine/carbon tetrabromide, phosphorous pentachloride, thionyl chloride, phosphorous tribromide, hydrofluoric acid/potassium fluoride, and dimethyl sulfide/N-bromosuccinimide. Suitable solvents for this reaction include but are not limited to tetrahydrofuran, dioxane, diethyl ether, dichloromethane, chloroform, acetonitrile, toluene, 1,2-dimethoxyethane, and hexanes.

A compound of formula (I-N) may be further converted to a compound of formula (I-O) using a reduction.

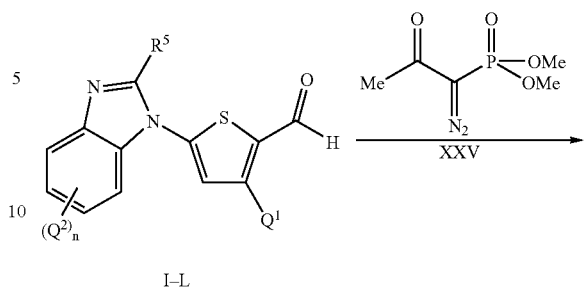

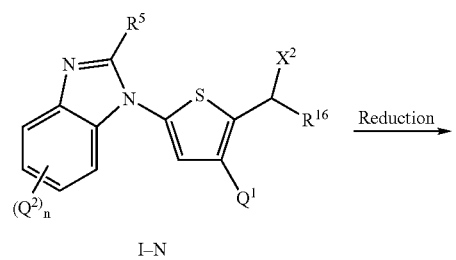

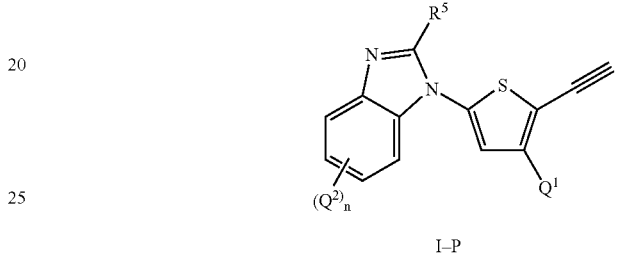

wherein all variables are as defined above.

This reaction is carried out in an inert solvent, conveniently at room temperature. The synthesis and use of the compound of formula (XXV) is analogous to that described in Mueller, S., et al., *Synlett* 6:521-522(1996). Typically, the reaction is carried out using methanol as the solvent and a base such as potassium carbonate.

In another embodiment, a compound of formula (I-Q) may be converted to a compound of formula (I-R), which may in turn be converted to a compound of formula (I-S), or a compound of formula (I-Q) may be converted directed to a compound of formula (I-S).

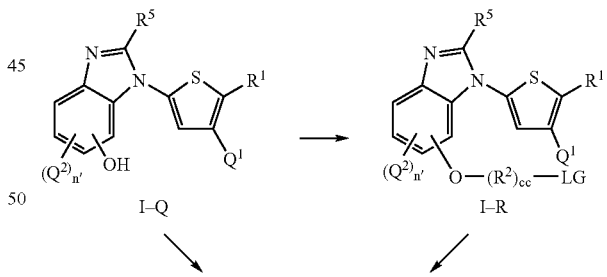

wherein $X^2$ is halo;

$R^{16}$ is H, alkyl, alkenyl or alkynyl; and all other variables are as defined above.

This reaction may be carried out in an inert solvent using a variety of conditions. Examples of suitable reducing agents for this reaction include but are not limited to, lithium/ammonia, zinc/acetic acid, lithium triethylborohydride, tributyltin hydride, lithium aluminum hydride, and samarium (II) iodide. Suitable solvents for this reaction vary considerably depending upon the chosen reducing agent. Examples of suitable solvents include but are not limited to, tetrahydrofuran, diethyl ether, 1,2-dimethoxyethane, dioxane, toluene, and hexanes.

A compound of formula (I-L) may be further converted to a compound of formula (I-P) by reacting with a compound of the formula (XXV).

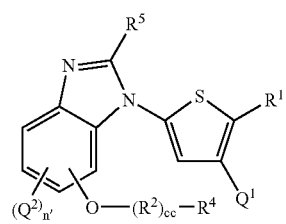

wherein n' is 0, 1, 2 or 3;

each LG is the same or different suitable leaving group; and all other variables are as defined above.

Compounds of formula (I-Q) may be prepared according to any of the methods described herein above. The compound of formula (I-Q) may then be converted to a compound of formula (I-R) or a compound of formula (I-S).

The compound of formula (I-R) may be prepared by either of two methods. According to one method, a compound of formula (I-R) is prepared by reacting a compound of formula (I-Q) with a compound of formula: LG-(R$^2$)$_{cc}$-LG (XXVII), wherein all variables are as defined above. Specific examples of suitable leaving groups include but are not limited to —Cl, —Br, —I, —OSO$_2$CH$_3$ and —OSO$_2$-Phenyl. Suitable compounds of formula (XXVII) are commercially available or may be prepared using conventional techniques. The reaction may be carried out in an inert solvent, conveniently at room temperature, in the presence of a suitable base. Examples of suitable bases for this reaction include but are not limited to, potassium carbonate, sodium carbonate, cesium carbonate, sodium hydride, and potassium hydride. Examples of suitable inert solvents for this reaction include but are not limited to, N,N-dimethylformamide, tetrahydrofuran, dioxane, and 1,2-dimethoxyethane.

According to a second method, a compound of formula (I-R) is prepared by reacting a compound of formula (I-Q) with a compound of formula: HO—(R$^2$)$_{cc}$-LG (XXVIII), wherein all variables are as defined above. Specific examples of suitable leaving groups include those described above. Compounds of formula (XXVIII) are commercially available or can be prepared using conventional techniques. The reaction is carried out in an inert solvent under standard Mitsunobu conditions. See, Hughes, D. L., *Org. React.* 42:335-656 (1992); and Mitsunobu, O., *Synthesis* 1-28 (1981). Typically the compound of formula (I-Q) and the compound of formula (XXVIII) are reacted together with a triarylphosphine, and a dialkyl azodicarboxylate at room temperature. Examples of suitable triarylphosphines include but are not limited to, triphenylphosphine, tri-tolylphosphine, and tri-mesitylphosphine. Examples of suitable dialkyl azodicarboxylates include but are not limited to, diethyl azodicarboxylate, diisopropyl azodicarboxylate, and di-tert-butyl azodicarboxylate. Examples of suitable inert solvents for this reaction include but are not limited to, tetrahydrofuran, dioxane, 1,2-dimethoxyethane, dichloromethane, and toluene.

The compound of formula (I-R) may be converted to a compound of formula (I-S) by reaction with a suitable nucleophile for installing the group R$^4$. Examples of suitable nucleophiles include but are not limited to ammonia, primary and secondary amines, metal alkoxides, metal thioalkoxides, potassium cyanide, sodium azide, organolithium reagents, organocuprates, and Grignard reagents. The specific conditions for these displacements vary, but the use of these types of nucleophiles for the installation of a group as defined by R$^4$ are conventional in the art. Displacement of the leaving group with such a nucleophile would either install the R$^4$ functionality or provide an intermediate from which the R$^4$ functional group could be readily installed according to conventional methods by one skilled in the art.

Alternatively, a compound of formula (I-S) may be prepared directly from a compound of formula (I-Q) using procedures analogous to those described above for the conversion of a compound of formula (I-Q) to a compound of formula (I-R). More specifically, a compound of formula (I-S) may be prepared by reacting a compound of formula (I-Q) with a compound of formula: LG-(R$^2$)$_{cc}$—R$^4$ (XXIX) using conditions analogous to those described above for the reaction of a compound of formula (I-Q) with a compound of formula (XXVII). Compounds of formula (XXIX) are commercially available or can be prepared using conventional techniques.

In another embodiment, a compound of formula (I-Q) is converted to a compound of formula (I-S) by reacting with a compound of formula: HO—(R$^2$)$_{cc}$—R$^4$ (XXX) under the conditions described above for the reaction of a compound of formula (I-Q) with a compound of formula (XXVIII). Compounds of formula (XXX) are commercially available or can be prepared using conventional techniques.

As a further example, a compound of formula (I-T) may be converted to a compound of formula (I-U), which may optionally be further converted to a compound of formula (I-V).

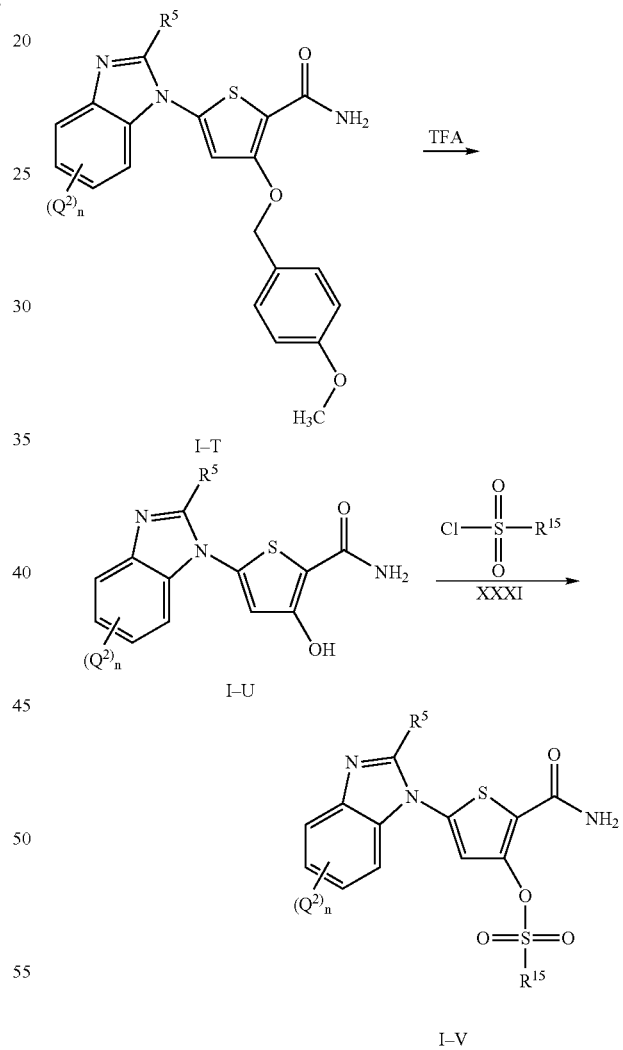

wherein:

R$^{15}$ is alkyl or phenyl; and all other variables are as defined in connection with Schemes 1-5 above.

A compound of formula (I-T) may be converted to a compound of formula (I-U) by reacting with a suitable acid, such as trifluoroacetic acid (TFA). This reaction may be carried out neat or in an inert solvent at ambient temperature. Suitable solvents for this reaction include but are not limited to, dichloromethane and chloroform.

The compound of formula (I-U) may be further converted to a compound of formula (I-V) by reacting with sulfonyl chlorides of formula (XXXI). The reaction may be carried out in an inert solvent at ambient temperature using a variety of bases. Examples of suitable bases include but are not limited to, triethylamine, N,N-diisopropylethylamine, and pyridine. Suitable solvents for this reaction include but are not limited to, dichloromethane, chloroform, tetrahydrofuran, 1,2-dimethoxyethane, dioxane, and N,N-dimethylformamide.

In another embodiment, a compound of formula (I-W) may be converted to a compound of formula (I-X). A compound of formula (I-X) may be further converted to a compound of formula (I-Y).

compound of formula (I-Y). Specific examples of suitable nucleophiles for this reaction include but are not limited to sodium hydroxide, sodium acetate, ammonia, and mono and di-substituted amines. The reaction with the nucleophile is typically carried out using equimolar or a slight excess of the nucleophile in an inert solvent, such as THF, at ambient or elevated temperatures. In another embodiment, a compound of formula (I-X) may be converted to a compound of formula (I-Y) in a sealed tube at elevated temperatures between 80° C. and 120° C., using excess ammonia in an appropriate solvent such as methanol, ethanol, isopropanol, tetrahydrofuran and dioxane.

Similarly, a compound of formula (I-AA) may also be converted to a compound of formula (I-BB) by oxidation, and the compound of formula (I-BB) may be converted to a compound of formula (I-CC) by reaction with ammonia.

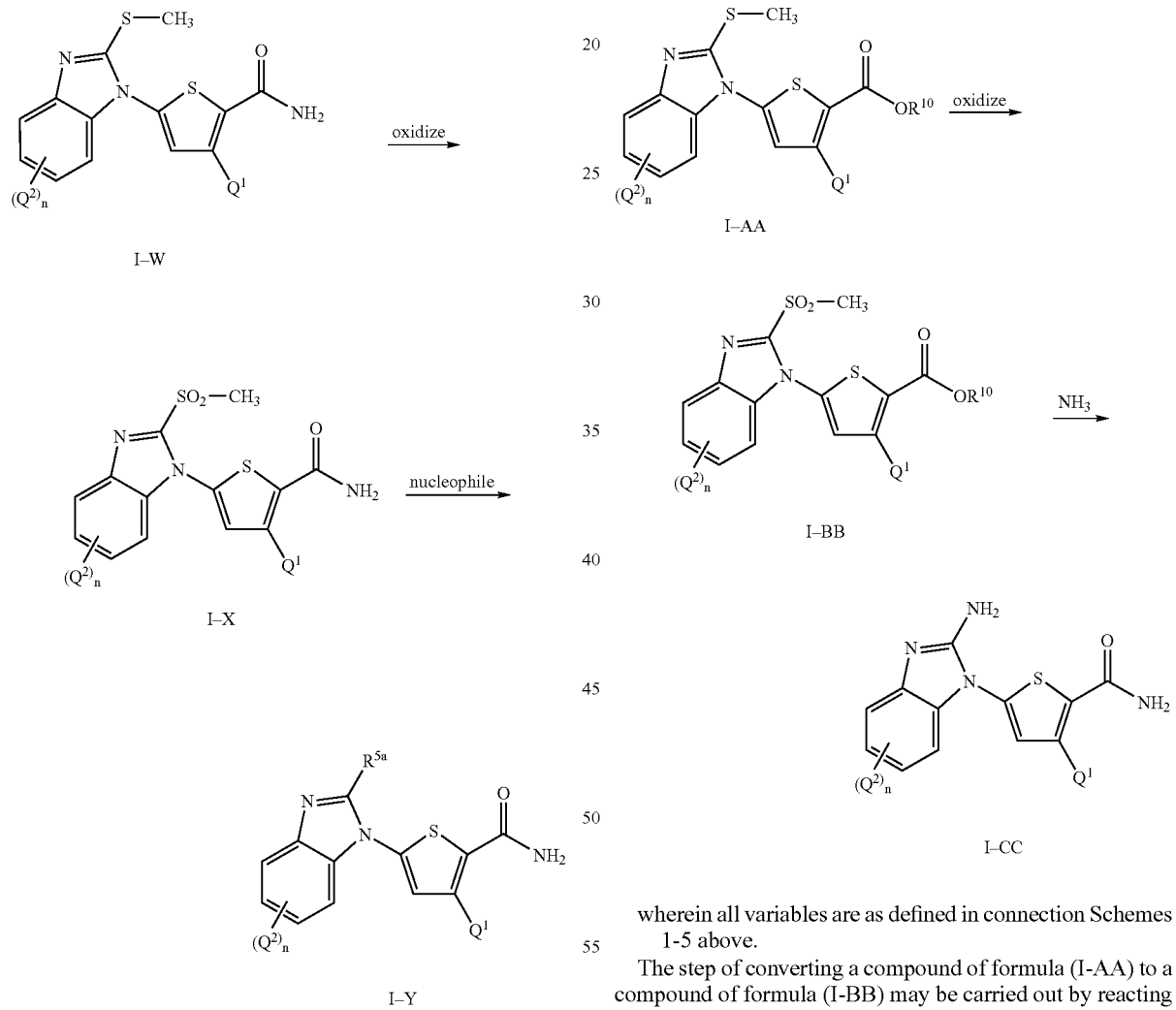

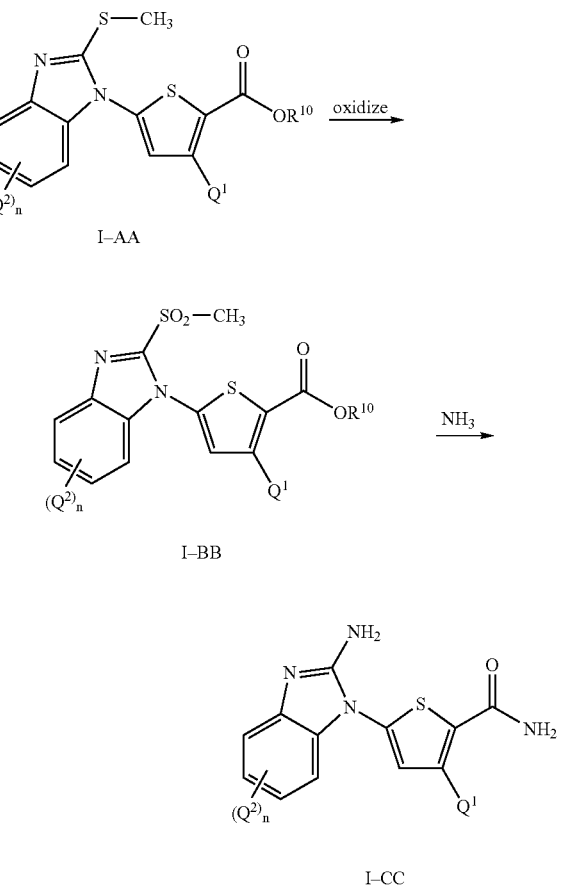

wherein $R^{5a}$ is selected from the group consisting of —$OR^7$ and —$NR^7R^8$;

and all other variables are as defined above.

A compound of formula (I-W) may be oxidized to a compound of formula (I-X) using a conventional oxidizing agent, such as for example, 3-chloroperoxybenzoic acid. Reaction of the compound of formula (I-X) with a suitable nucleophile of formula $R^{5a}$ will convert a compound of formula (I-X) to a wherein all variables are as defined in connection Schemes 1-5 above.

The step of converting a compound of formula (I-AA) to a compound of formula (I-BB) may be carried out by reacting a compound of formula (I-AA) with a suitable oxidizing agent, such as for example 3-chloroperoxybenzoic acid. The compound of formula (I-BB) may be converted to a compound of formula (I-CC) by reaction with excess ammonia in a sealed tube at elevated temperature between about 80 and about 120° C. in a suitable solvent. Suitable solvents for this reaction include but are not limited to methanol, ethanol, isopropanol, tetrahydrofuran and dioxane.

A further example of a process for converting a compound of formula (I) to a different compound of formula (I) includes the reaction of a compound of formula (I-DD) with a thionating reagent to prepare a compound of formula (I-EE).

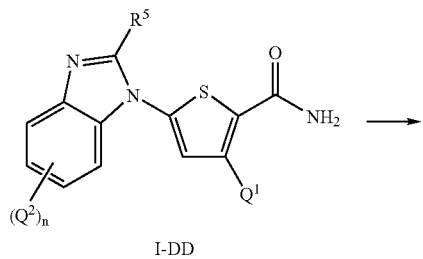

I-DD wherein all variables are as defined above.

The reaction may be carried out in an inert solvent and optionally heated to a temperature of from about 65 to above about 100° C. Examples of suitable thionating reagents include but are not limited to phosphorus pentasulfide, 2,4-bis(4-methoxyphenyl)-1,3-dithia-2,4-diphosphetane-2,4-disulfide and the like. Suitable solvents include but are not limited to xylene, dioxane and toluene.

Further, a compound of formula (I-FF) may be converted to a compound of formula (I-GG) by reaction with an azide source in an inert solvent.

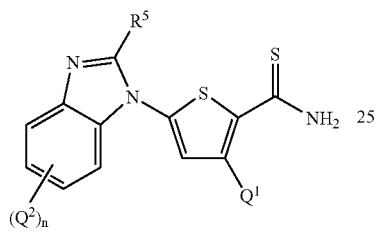

I-EE

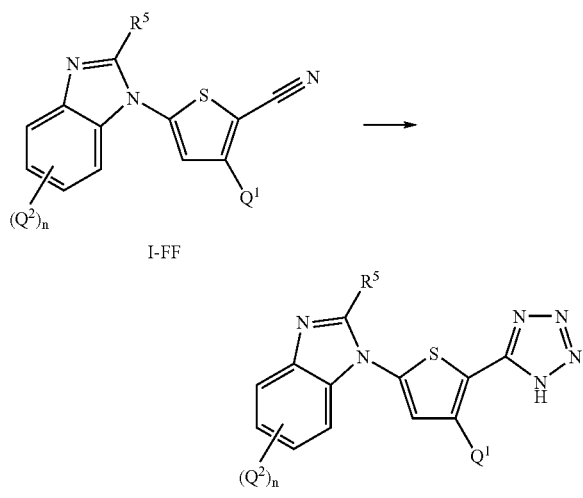

I-FF

I-GG wherein all variables are as defined above.

Examples of suitable azide sources include but are not limited to hydrazoic acid, sodium azide with ammonium chloride, sodium azide with aluminum chloride, and sodium azide with zinc(II) bromide. By way of example some preferred solvents include but are not limited to dimethylformamide, dimethylsulfoxide, N-methylpyrrolidinone, toluene and the like. The reaction may be optionally heated to a temperature of from about 23 to about 150° C.

In another embodiment, a compound of formula (I-HH) may be converted to a compound of formula (I-II) using a coupling protocol.

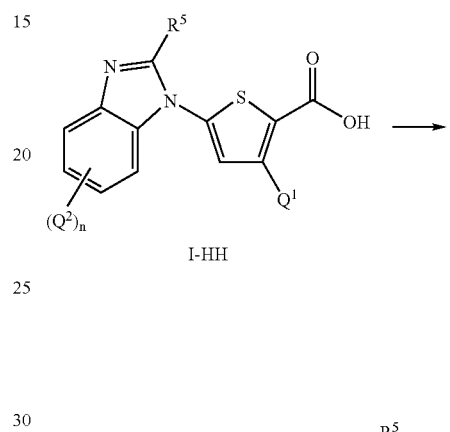

I-HH

I-II wherein all variables are as defined above.

The conversion reaction can be carried out by reacting a compound of formula (I-HH) with a suitable coupling reagent in an inert solvent, followed by the addition of a hydroxylamine source, and optionally a base. Suitable coupling reagents include but are not limited to 1,1-carbonyldiimidazole, oxalyl chloride, dicyclohexylcarbodiimide and 1-(N,N-diphenylcarbamoyl)pyridinium chloride. Preferably the hydroxylamine is hydroxylamine hydrochloride. Suitable bases include but are not limited to triethylamine, sodium methoxide and diisoproylethylamine. The reaction may be optionally heated to a temperature of from about 0° C. to about 80° C. Examples of suitable solvents for this reaction include but are not limited to dimethylformamide, dichloromethane and tetrahydrofuran.

In yet another example of a conversion using a coupling protocol a compound of formula (I-KK) is prepared from a compound of formula (I-JJ) as follows.

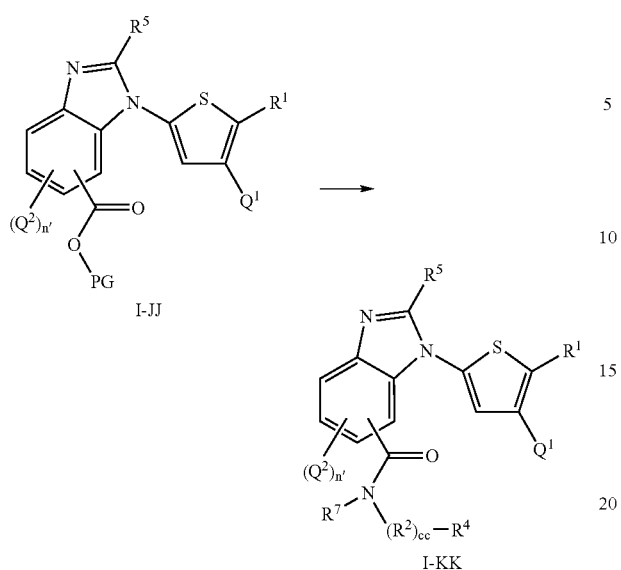

wherein n' is 0, 1, 2 or 3;
PG is a protecting group and
all other variables are as defined above.

The protecting group is typically carboxylic acid protecting group which when removed yields the acid. The cleavage of the carboxylic acid protecting group can be accomplished through many different methods conventional in the art. See, Kocienski, P. J. *Protecting Groups*, Georg Thieme Verlag, Stuttgart, 1994; and Greene, T. W., Wuts, P. G. M. *Protecting Groups in Organic Synthesis* (2$^{nd}$ Edition), J. Wiley and Sons, 1991.

Following the removal of the protecting group, the resulting carboxylic acid is reacted using a coupling protocol to yield the compound of formula (I-KK). The reaction can be carried out by reacting the deprotected compound of formula (I-JJ) with a suitable coupling reagent in an inert solvent, followed by the addition of a primary or secondary amine, and optionally a base. Suitable coupling reagents include but are not limited to 1,1-carbonyldiimidazole, oxalyl chloride, dicyclohexylcarbodiimide and O-(7-azabenzotriazol-1-yl)-1,1,3,3-tetramethyluronium hexafluorophosphate. Suitable bases include but are not limited to triethylamine, diisoproylethylamine and the like. The reaction may be optionally heated to a temperature of from about 0° C. to about 80° C. Examples of suitable solvents include but are not limited to dimethylformamide, dichloromethane and tetrahydrofuran.

In yet another example of a conversion using a coupling protocol a compound of formula (I-MM) is prepared from a compound of formula (I-LL) as follows.

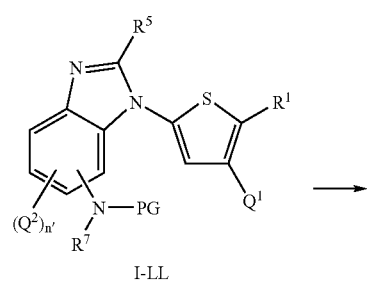

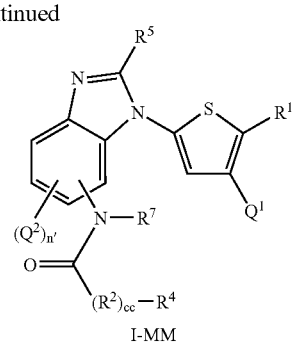

wherein n' is 0, 1, 2 or 3;
PG is a protecting group and
all other variables are as defined above.

The protecting group is amino protecting group which when removed yields the amine. The cleavage of the amino protecting group can be accomplished through many different methods conventional in the art. See, Kocienski, P. J. *Protecting Groups*, Georg Thieme Verlag, Stuttgart, 1994; and Greene, T. W., Wuts, P. G. M. *Protecting Groups in Organic Synthesis* (2$^{nd}$ Edition), J. Wiley and Sons, 1991.

Following the removal of the protecting group, the resulting amine is reacted using a coupling protocol to yield the compound of formula (I-MM). The reaction can be carried out by reacting the deprotected compound of formula (I-LL) with a carboxylic acid in the presence of a suitable coupling reagent in an inert solvent, and optionally a base. Suitable coupling reagents include but are not limited to 1,1-carbonyldiimidazole, oxalyl chloride, dicyclohexylcarbodiimide and O-(7-azabenzotriazol-1-yl)-1,1,3,3-tetramethyluronium hexafluorophosphate. Suitable bases include but are not limited to triethylamine, diisoproylethylamine and the like. The reaction may be optionally heated to a temperature of from about 0° C. to about 80° C. Examples of suitable solvents include but are not limited to dimethylformamide, dichloromethane and tetrahydrofuran.

Based upon this disclosure and the examples contained herein one skilled in the art can readily convert a compound of formula (I) or a pharmaceutically acceptable salt, solvate or physiologically functional derivative thereof into another compound of formula (I), or a pharmaceutically acceptable salt, solvate or physiologically functional derivative thereof.

The following examples are intended for illustration only and are not intended to limit the scope of the invention in any way, the invention being defined by the claims which follow.

Reagents are commercially available or are prepared according to procedures in the literature.

EXAMPLE 1

Methyl 5-(1H-benzimidazol-1-yl)-3-hydroxy-2-thiophenecarboxylate

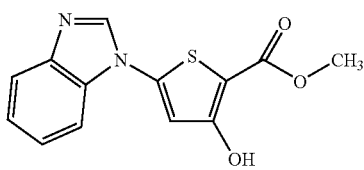

Process 1:

Benzimidazole (0.100 g, 0.846 mmol) was dissolved in 5 mL of chloroform with stirring. Methyl 2-chloro-3-oxo-2,3-dihydro-2-thiophenecarboxylate (0.179 g, 0.929 mmol) was added in a single portion followed by solid sodium bicarbonate (0.213 g, 2.52 mmol). The mixture was stirred for 16 hours at room temperature and poured into aqueous 0.1N HCl (50 mL). The mixture was extracted with dichloromethane and ethyl acetate. The combined organic layers were dried over magnesium sulfate, filtered, and concentrated in vacuo. The residue was purified by flash chromatography to afford 0.176 g of material that was shown to be >85% pure methyl 5-(1H-benzimidazol-1-yl)-3-hydroxy-2-thiophenecarboxylate. $^1$H NMR (400 MHz, CDCl$_3$) δ 10.90 (s, 1H), 8.73 (s, 1H), 7.87-7.81 (m, 2H), 7.55-7.30 (m, 2H), 7.18 (s, 1H), 3.83 (s, 3H). MS (ES+, m/z) 275 (m+1).

Process 2:

Benzimidazole (0.100 g, 0.846 mmol) is dissolved in 5 mL of chloroform with stirring. Methyl 2-chloro-3-oxo-2,3-dihydro-2-thiophenecarboxylate (0.179 g, 0.929 mmol) is added in a single portion followed by N-methylimidazole (0.20 mL, 2.5 mmol). The mixture is stirred for 16 hours at room temperature and poured into aqueous 0.1N HCl (50 mL). The mixture is extracted with dichloromethane and ethyl acetate. The combined organic layers are dried over magnesium sulfate, filtered, and concentrated in vacuo. The residue is purified by flash chromatography to afford 0.202 g of materail that is shown to be >85% pure methyl 5-(1H-benzimidazol-1-yl)-3-hydroxy-2-thiophenecarboxylate. $^1$H NMR (400 MHz, CDCl$_3$) δ 10.90 (s, 1H), 8.73 (s, 1H), 7.87-7.81 (m, 2H), 7.55-7.30 (m, 2H), 7.18 (s, 1H), 3.83 (s, 3H). MS (ES+, m/z) 275 (m+1).

EXAMPLE 2

Methyl 5-{6-[(tert-butoxycarbonyl)amino]-1H-benzimidazol-1-yl}-3-hydroxythiophene-2-carboxylate and methyl 5-{(5-[(tert-butoxycarbonyl)amino]-1H-benzimidazol-1-yl}-3-hydroxythiophene-2-carboxylate

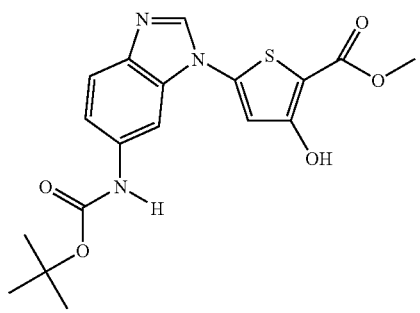

and

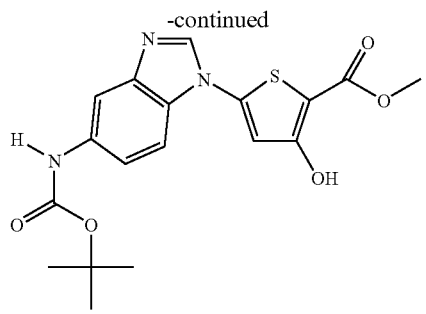

Compounds were prepared using a procedure similarly described in Example 1. MS (ES-, m/z) 388 (m-1).

EXAMPLE 3

Methyl 5-[5,6-bis(methyloxy)-1H-benzimidazol-1-yl]-3-hydroxy-2-thiophenecarboxylate

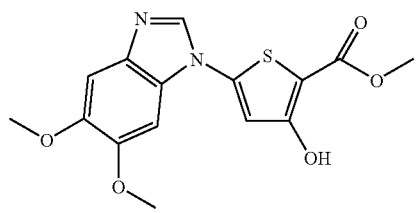

Compound was prepared using a procedure similarly described in Example 1. $^1$H NMR (DMSO-d$_6$): δ10.81 (br s, 1H), 8.54 (s, 1H), 7.59 (s, 1H), 7.56 (s, 1H), 7.11 (s, 1H), 3.79 (s, 3H), 2.37 (s, 3H), 2.33 (s, 3H). MS (ES+, m/z) 335 (M+1).

The following compounds can be prepared from appropriate substituted or unsubstituted benzimidazole and thiophene starting materials using the procedure described in Example 1 and optionally the conversion reactions described above.

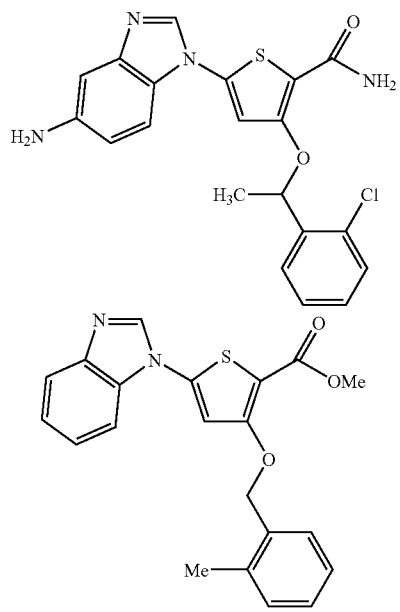

53
-continued
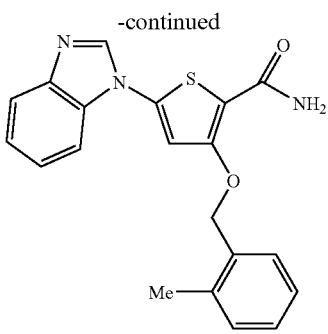
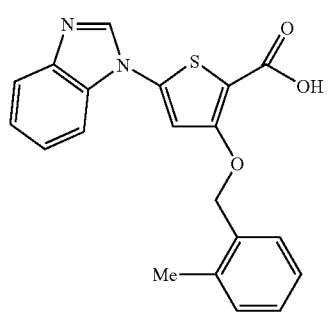
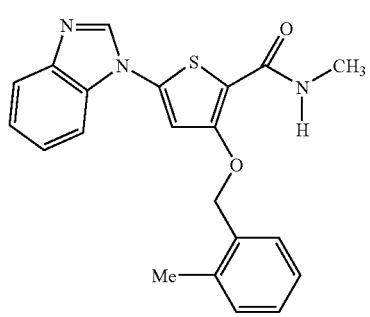
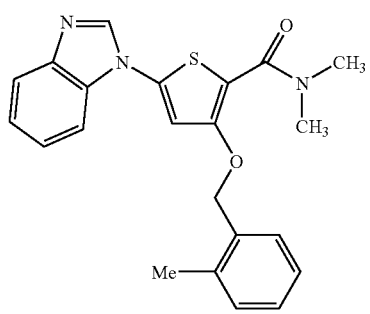
54
-continued
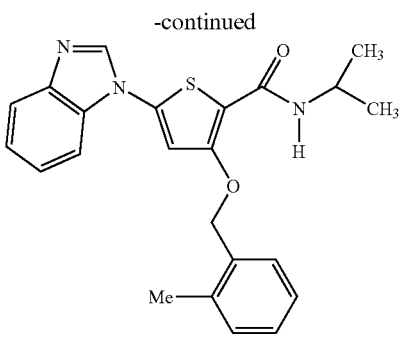
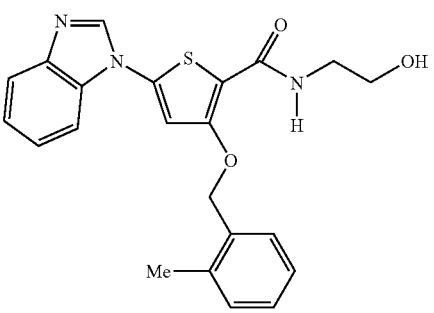
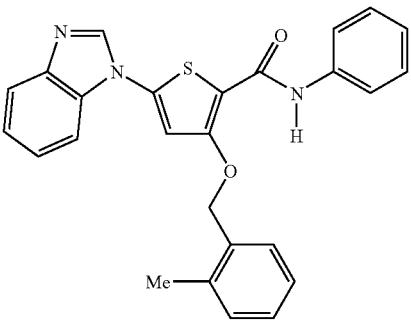
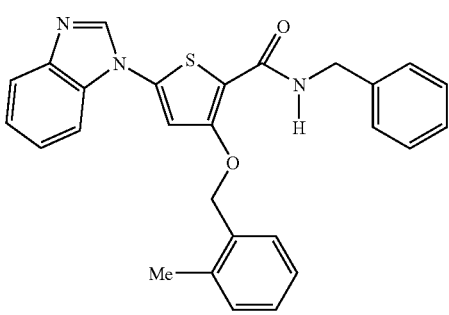

-continued
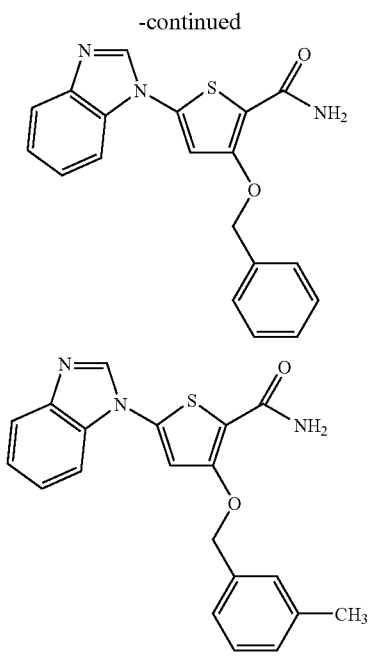
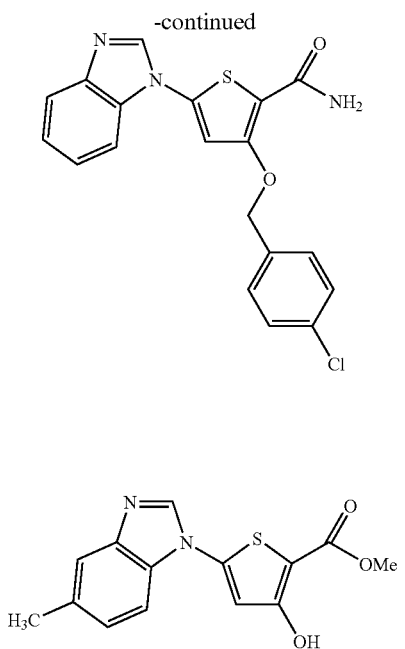
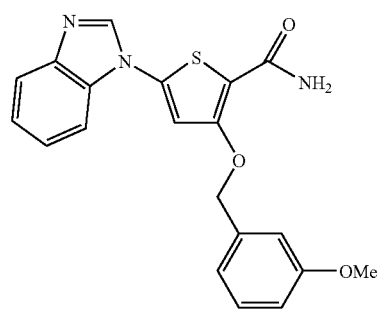
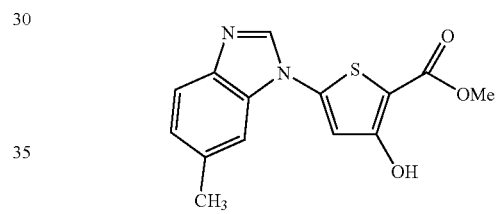
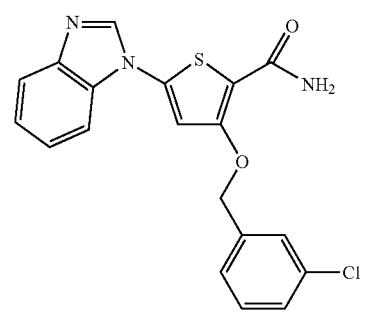
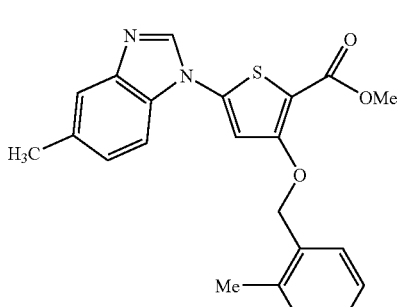
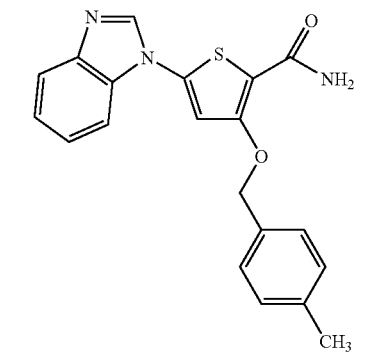
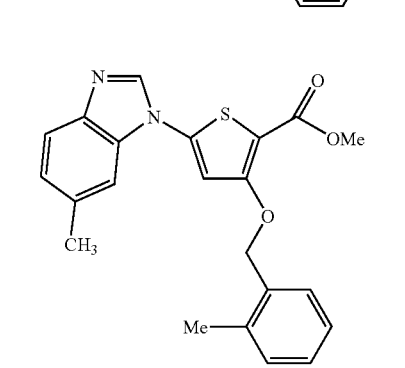

-continued
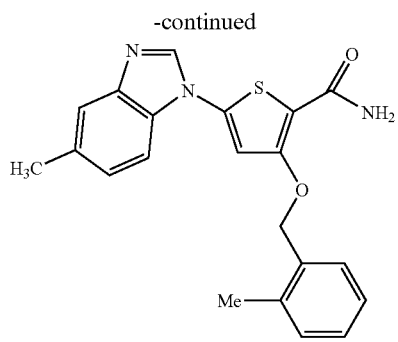
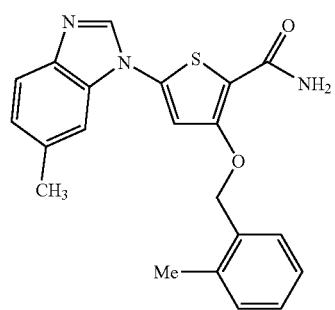
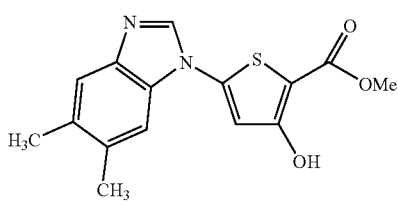
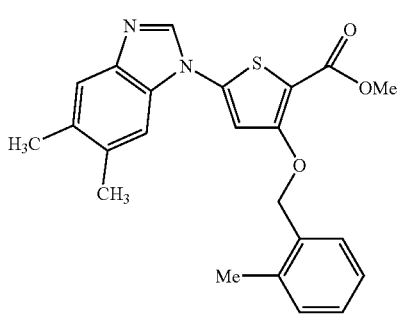
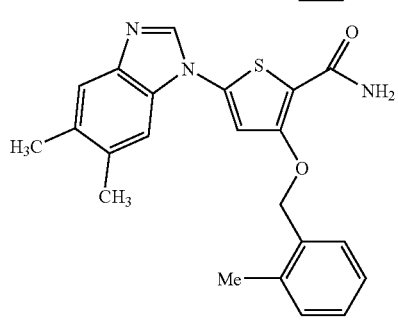
-continued
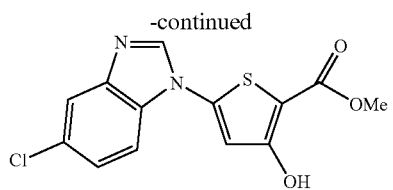
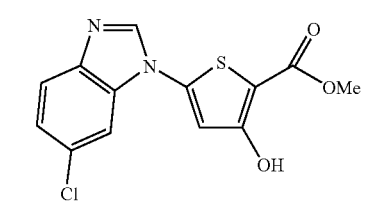
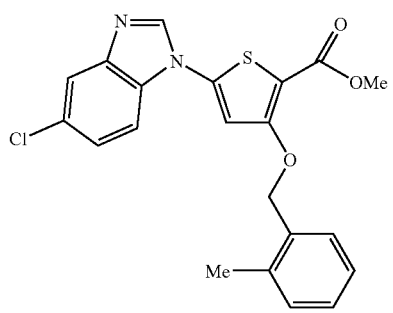
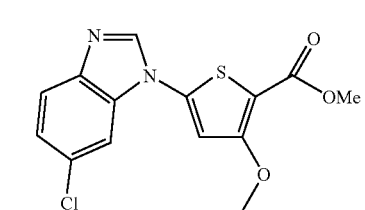
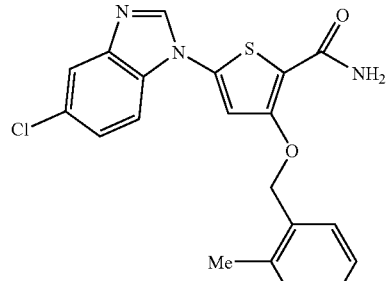
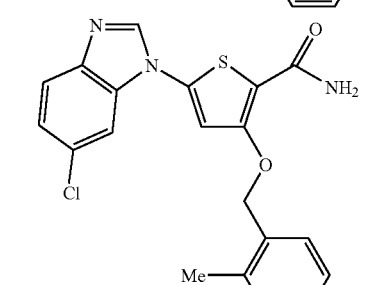

-continued
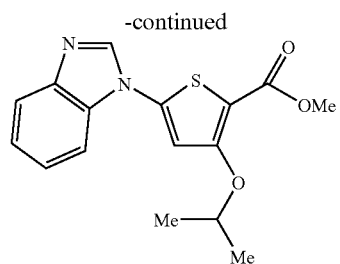
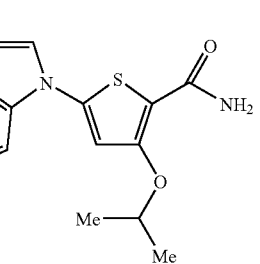
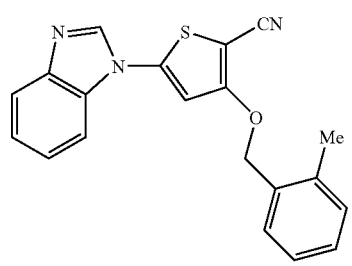
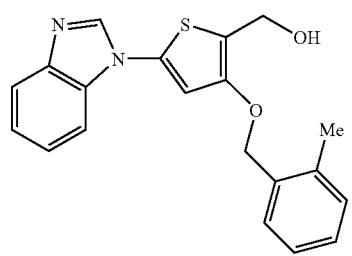
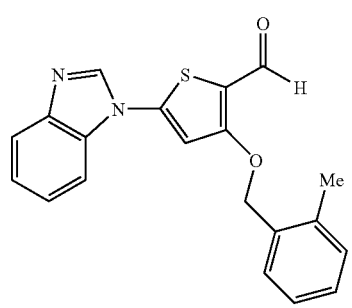
-continued
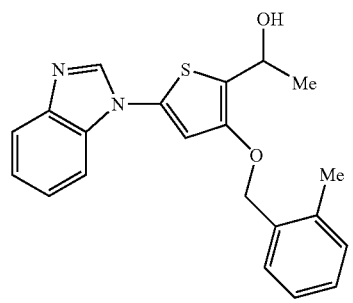
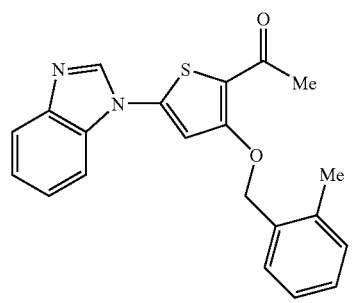
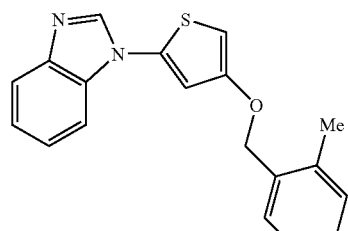
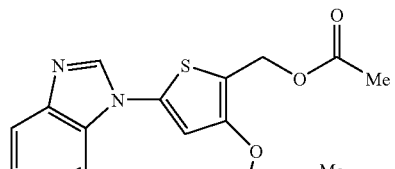
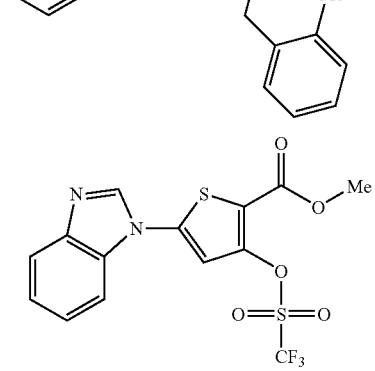
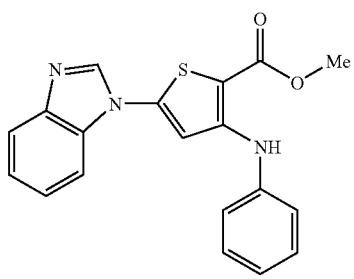

-continued
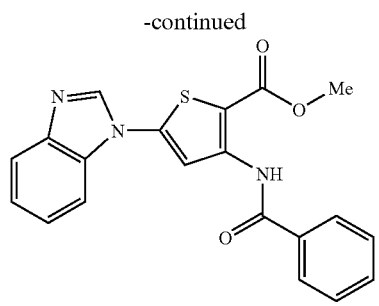
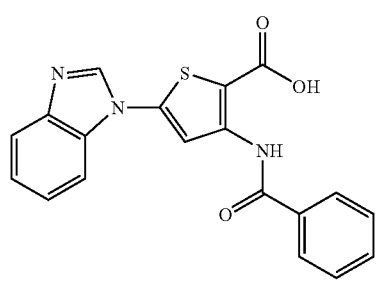
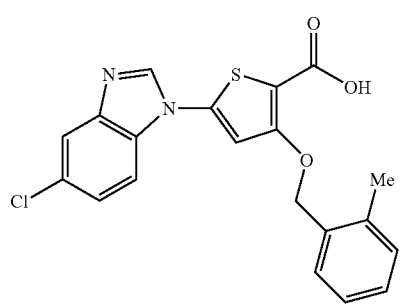
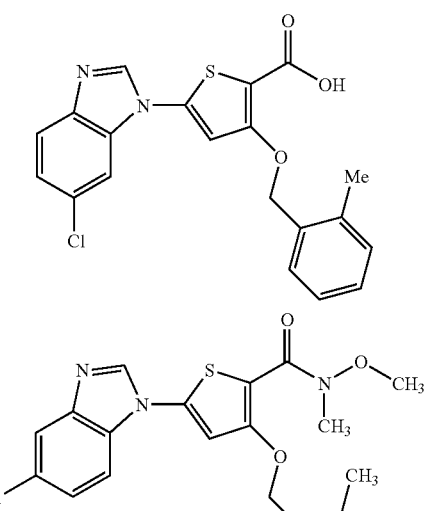
-continued
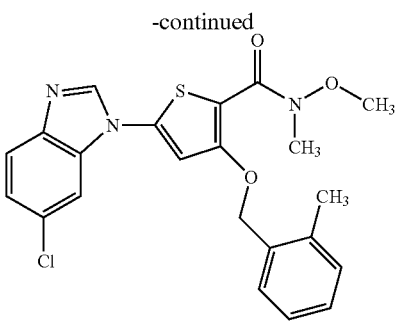
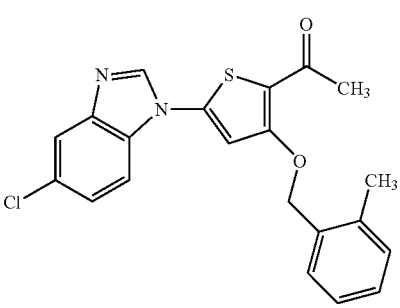
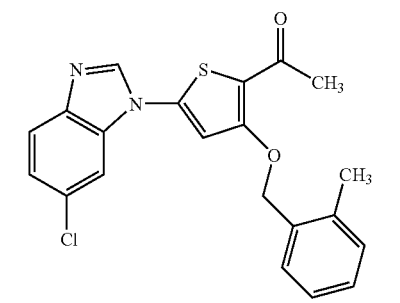
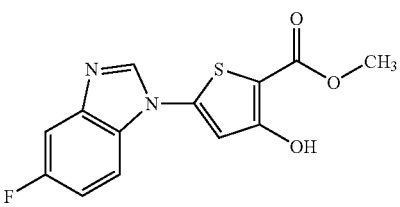
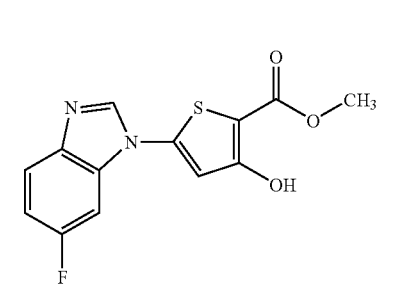

-continued
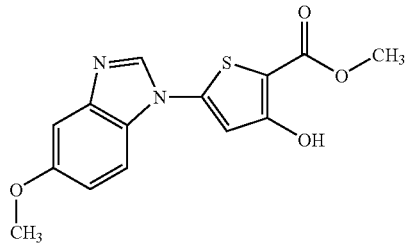
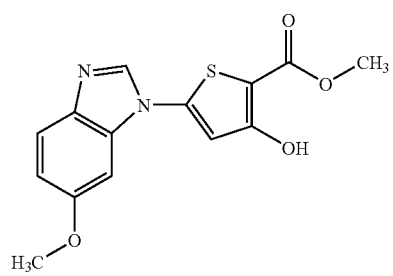
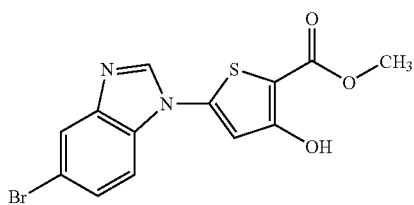
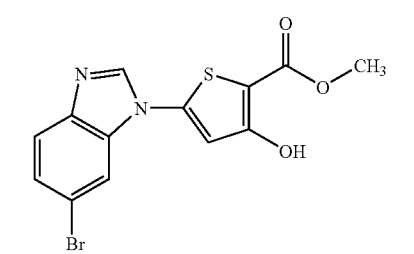
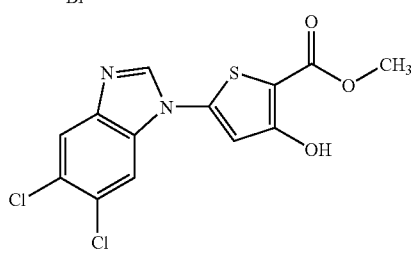
-continued
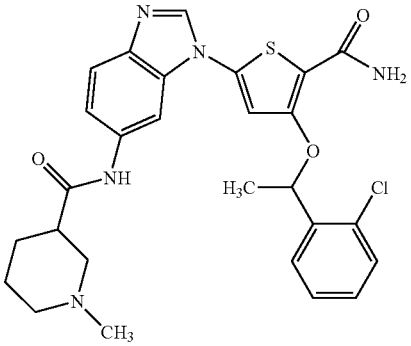
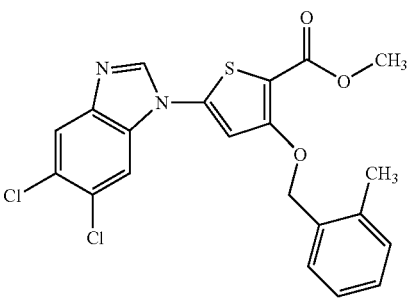
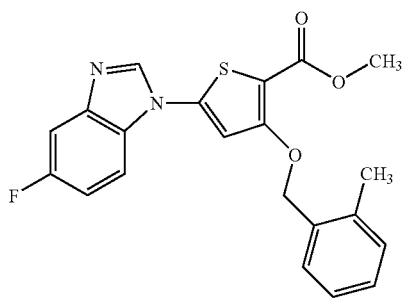
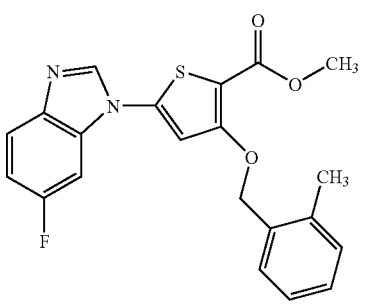

-continued
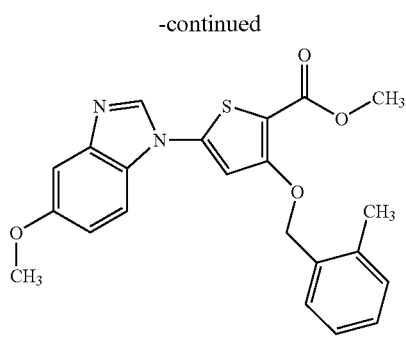
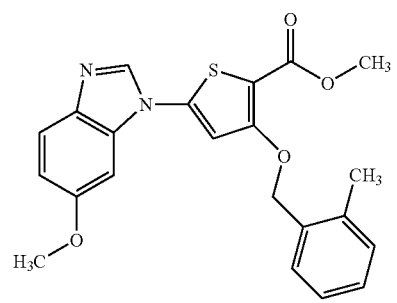
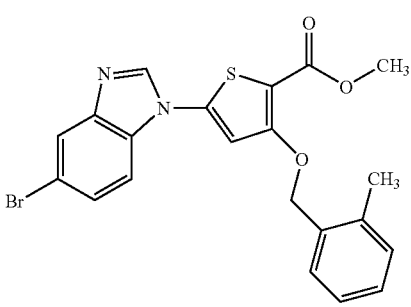
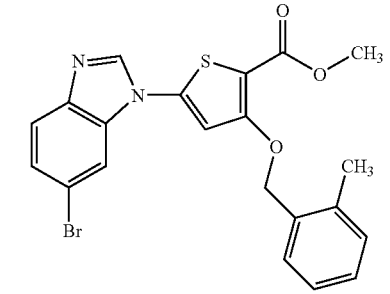
-continued
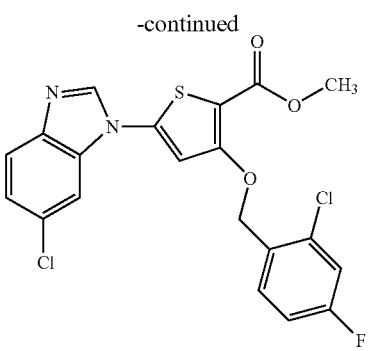
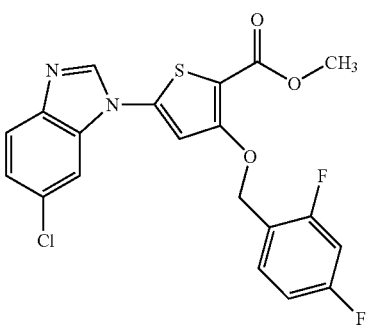
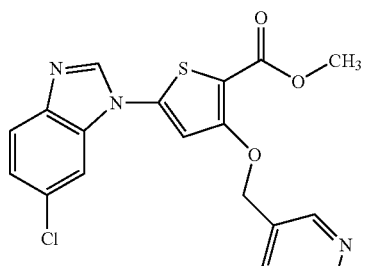
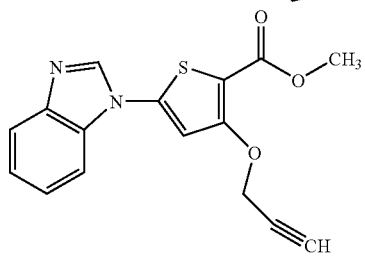
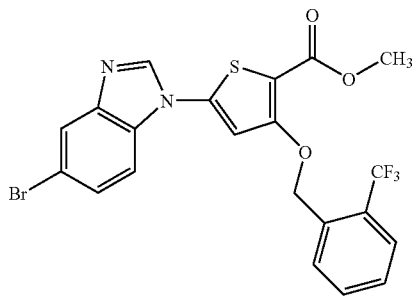

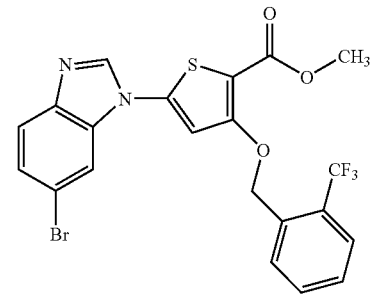
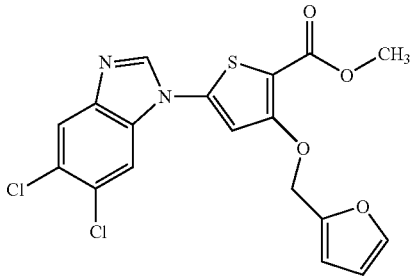

69
-continued
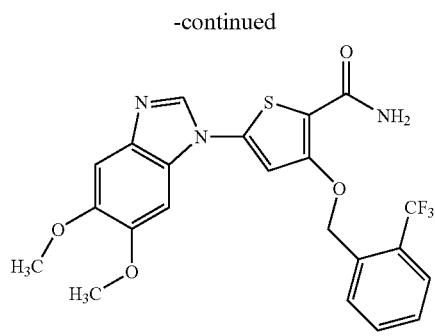
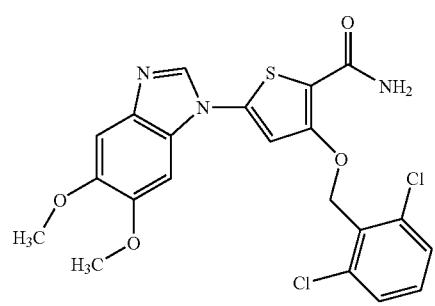
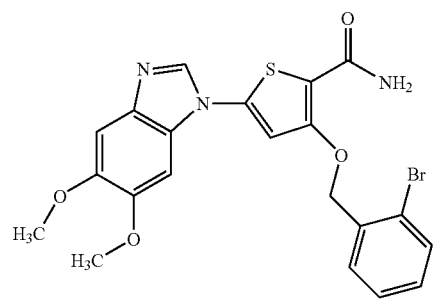
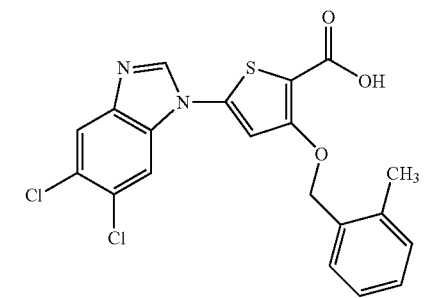
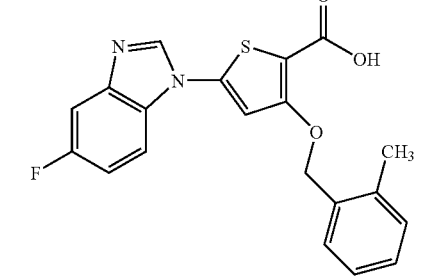
70
-continued
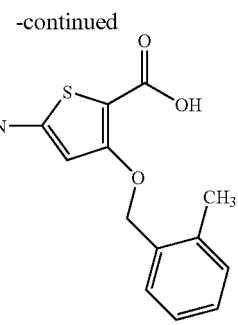
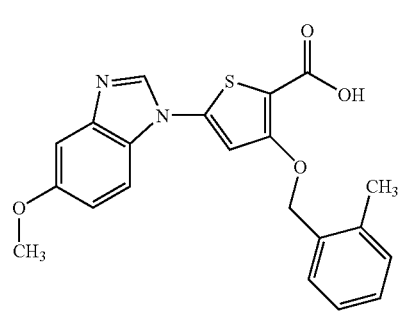
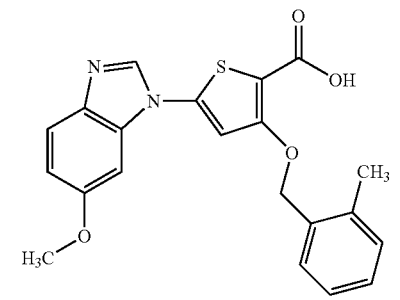
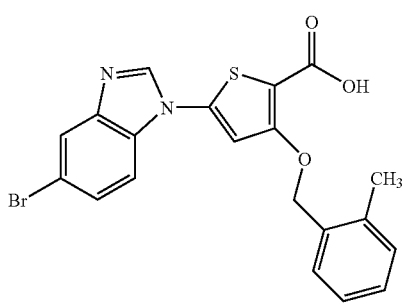
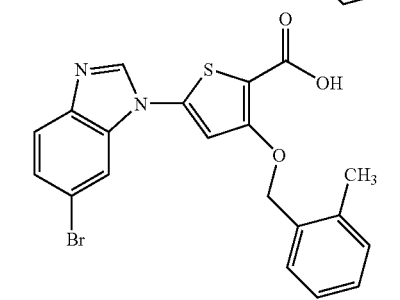

-continued
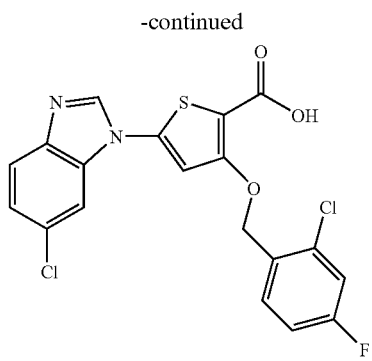
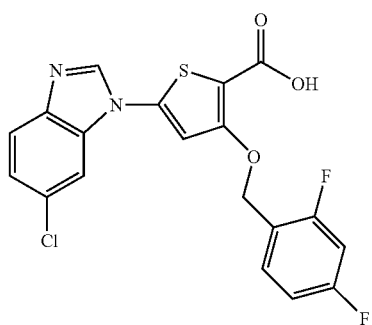
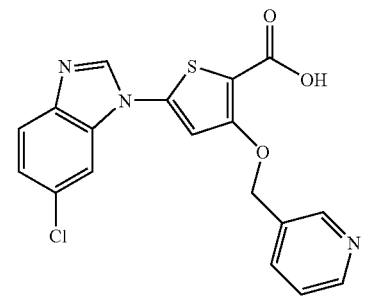
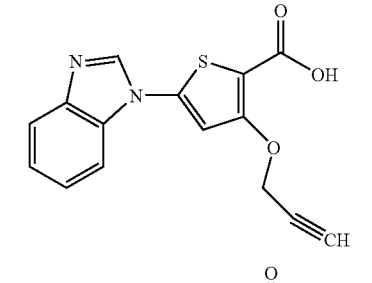
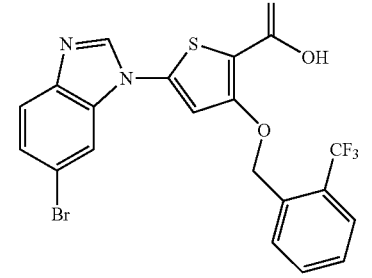
-continued
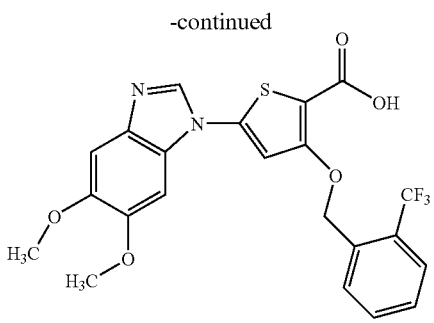
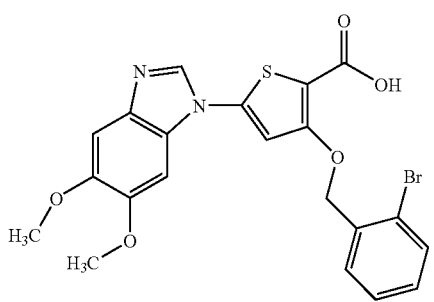
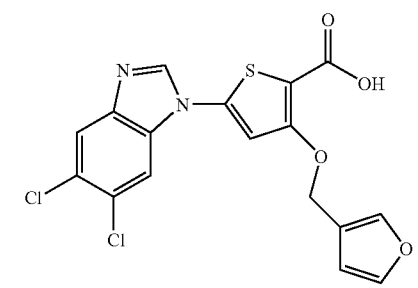
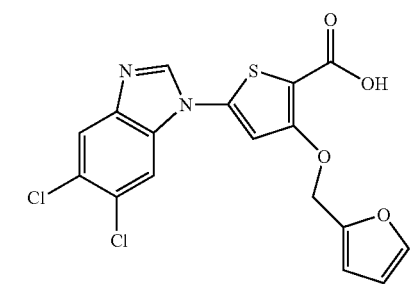
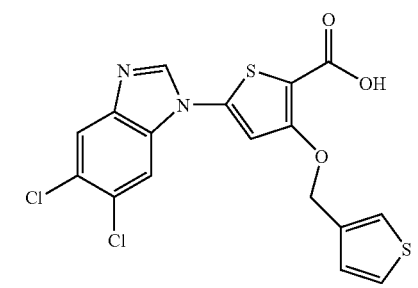

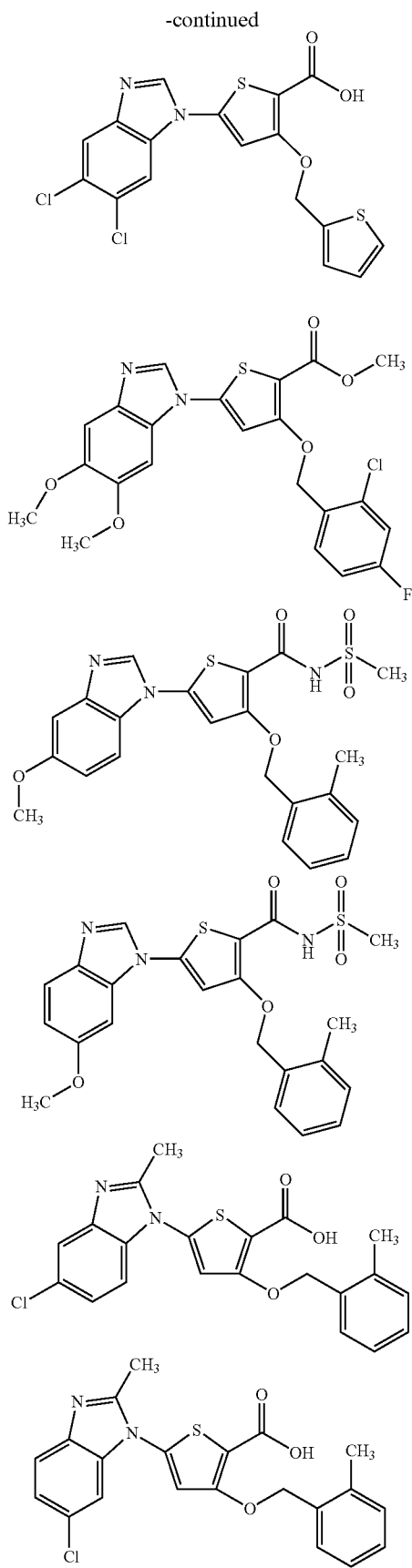
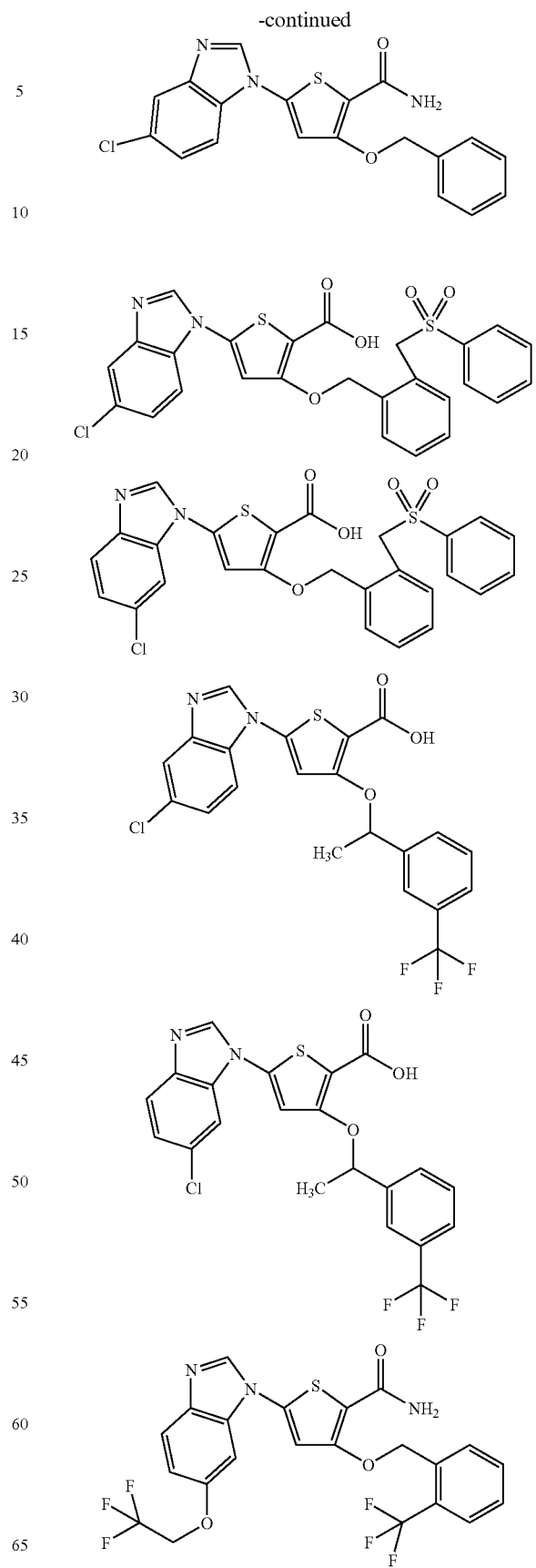

75
-continued
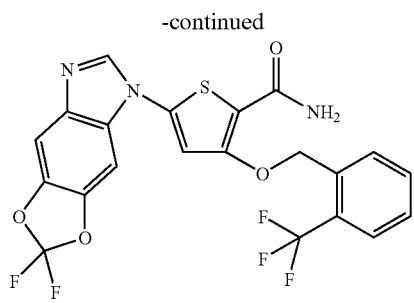
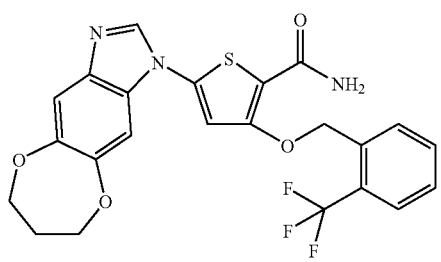
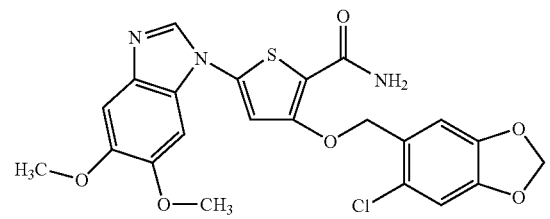
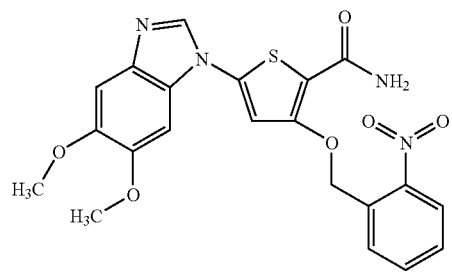
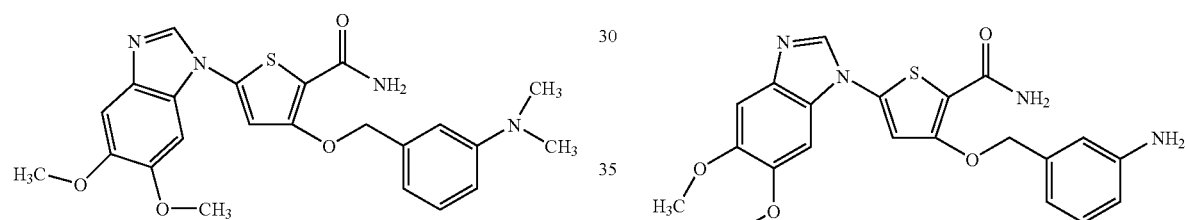
76
-continued
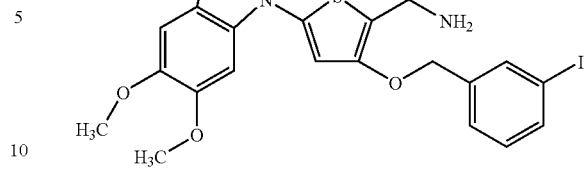
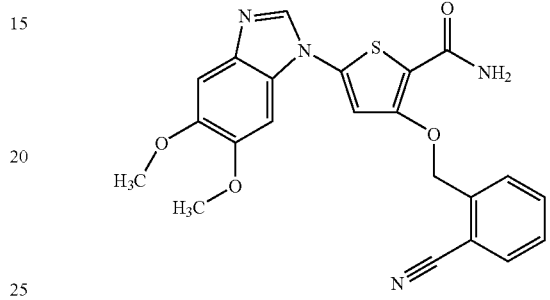
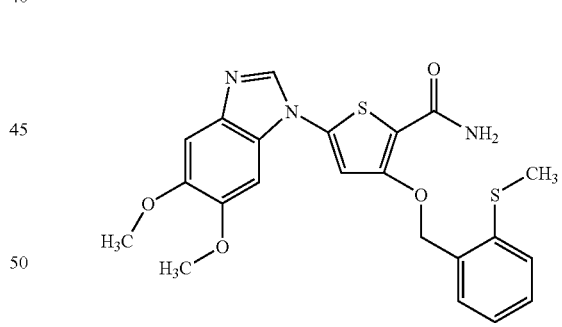
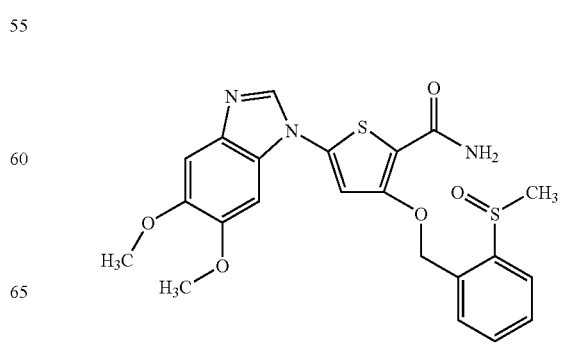

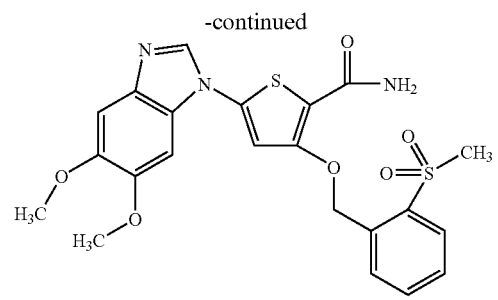
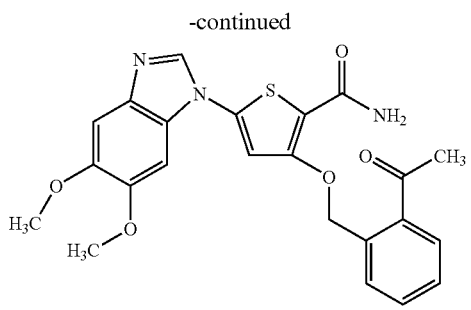
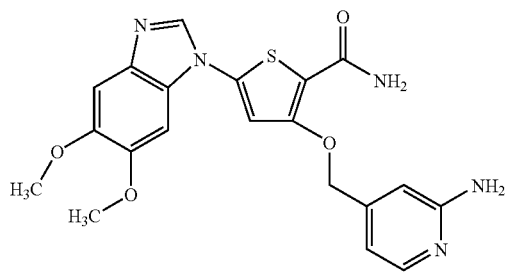
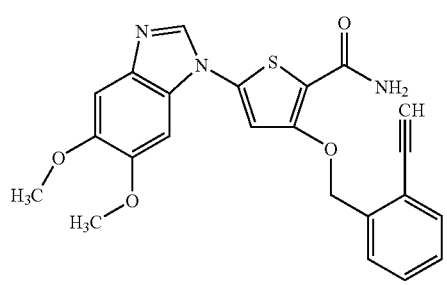
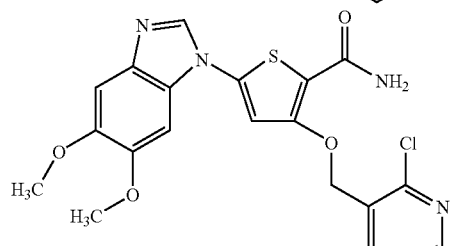
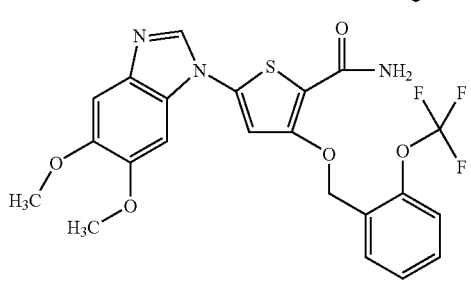
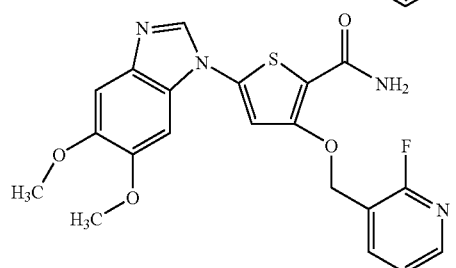
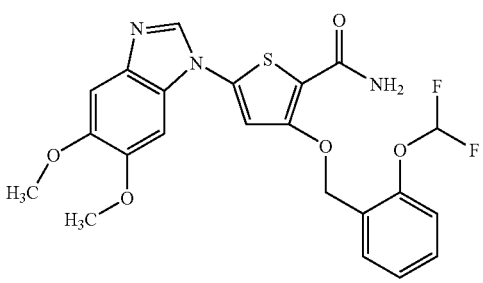
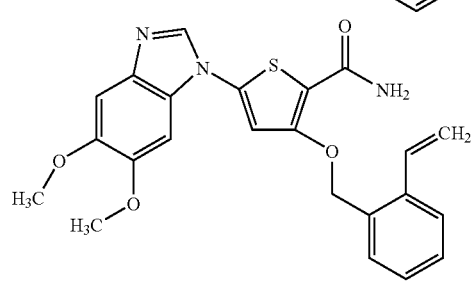
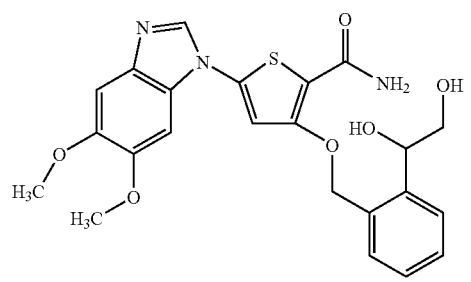
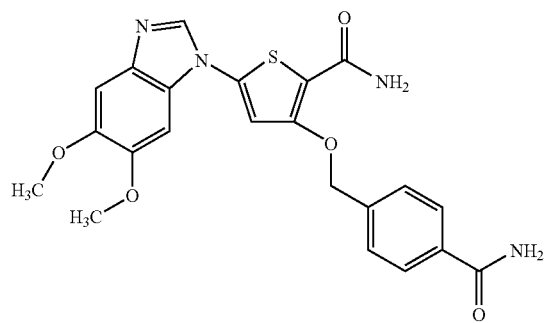
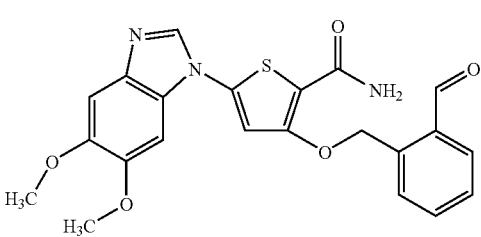

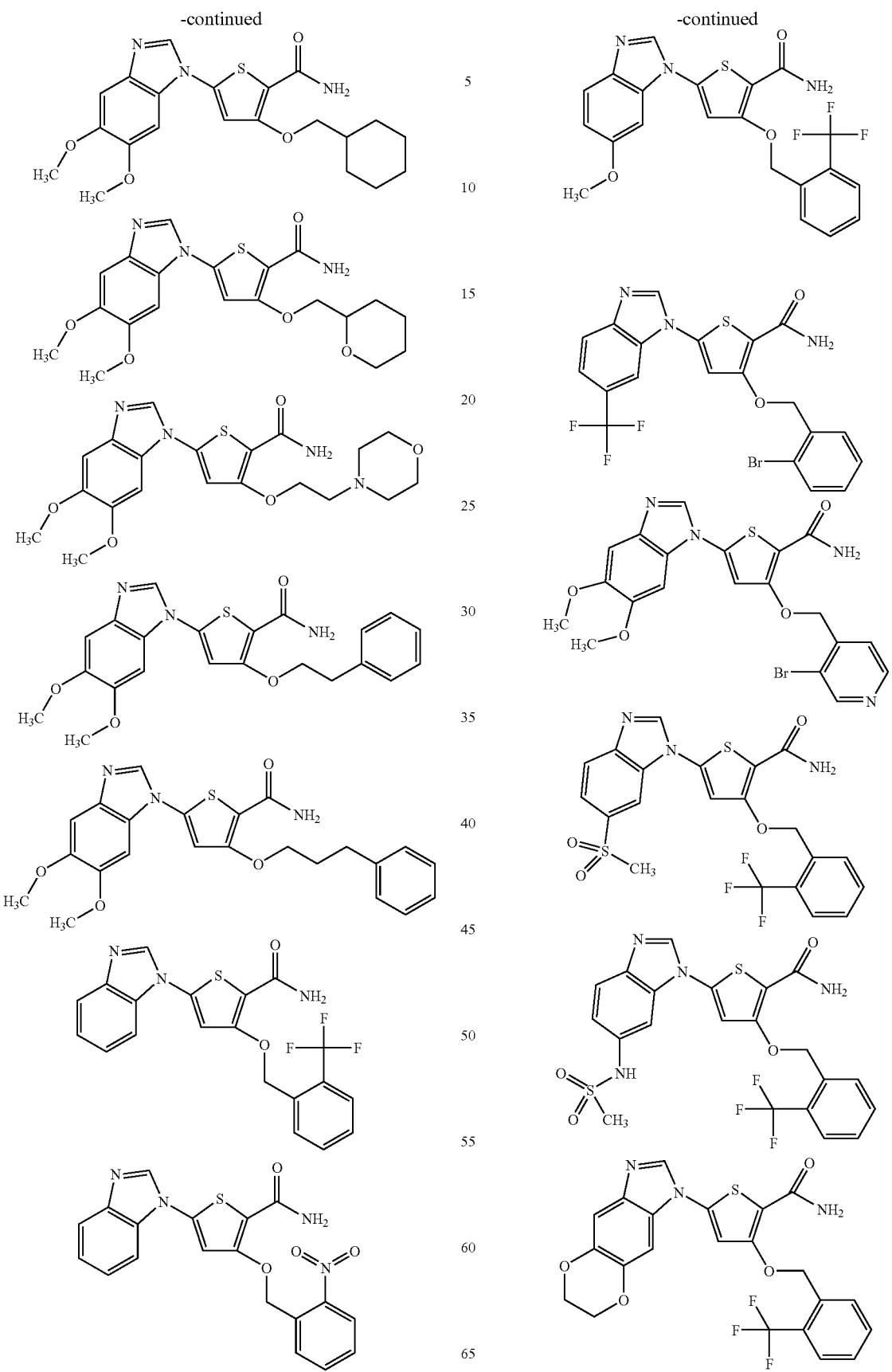

-continued
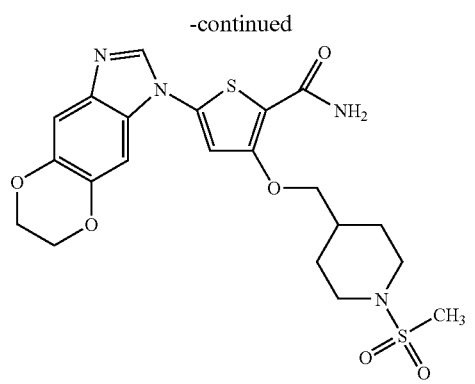
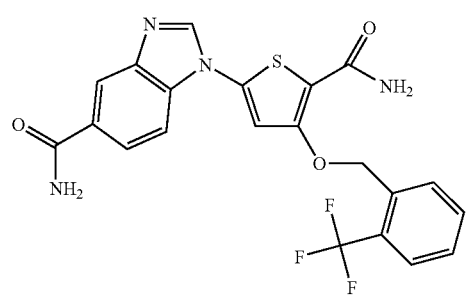
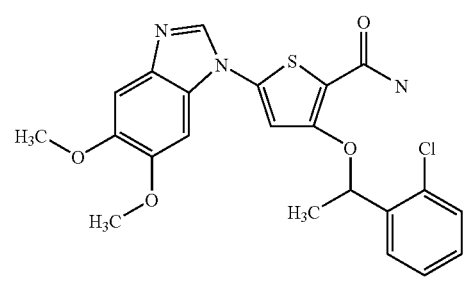
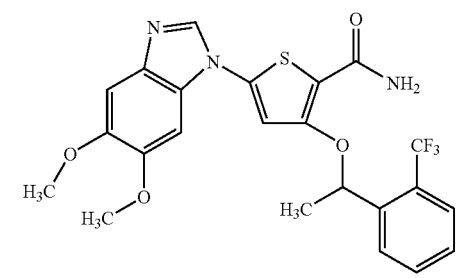
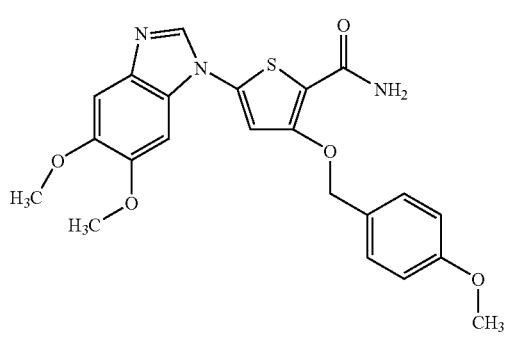
-continued
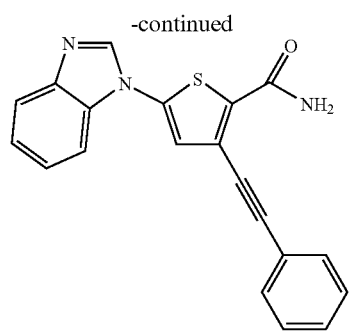
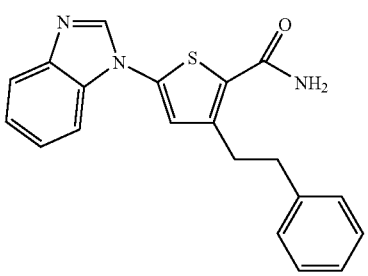
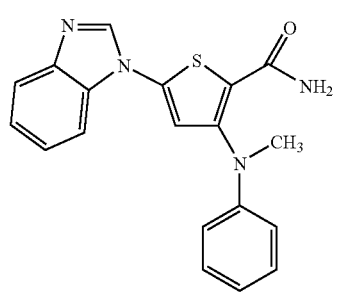
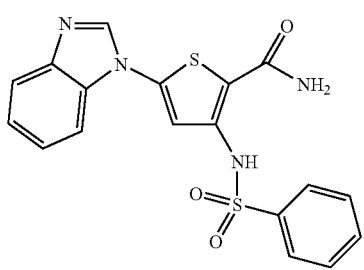
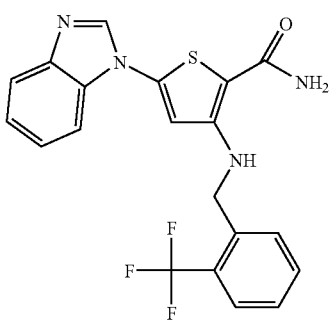

-continued
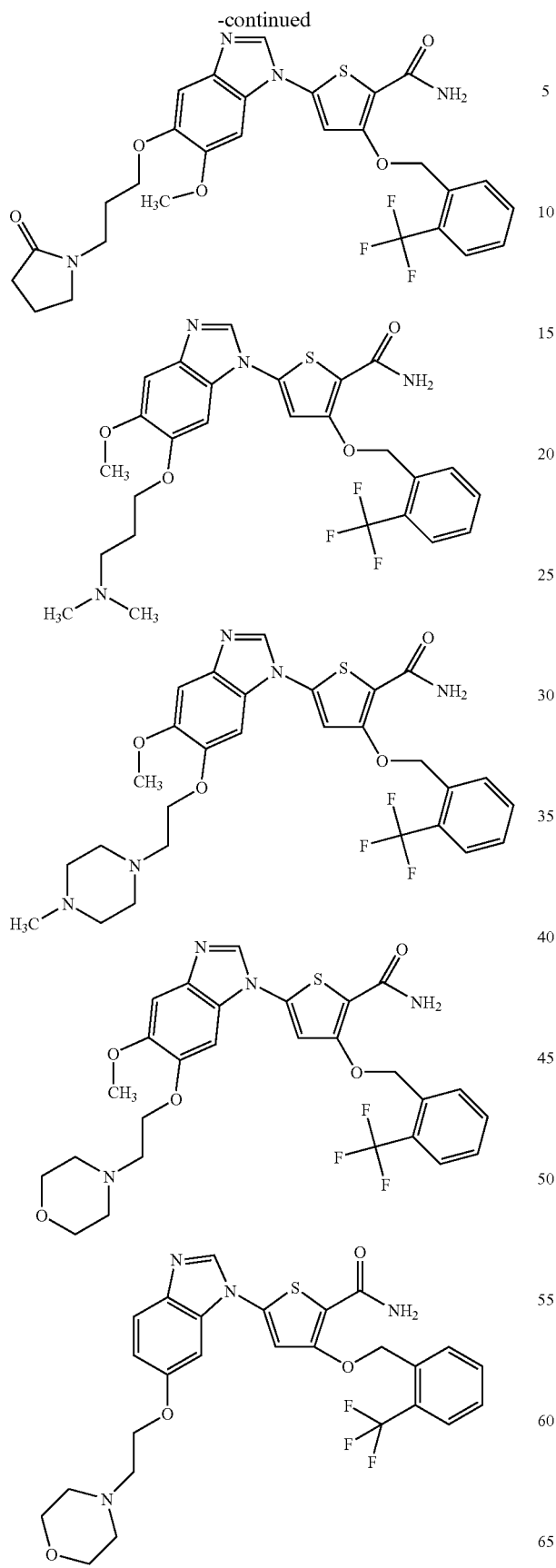
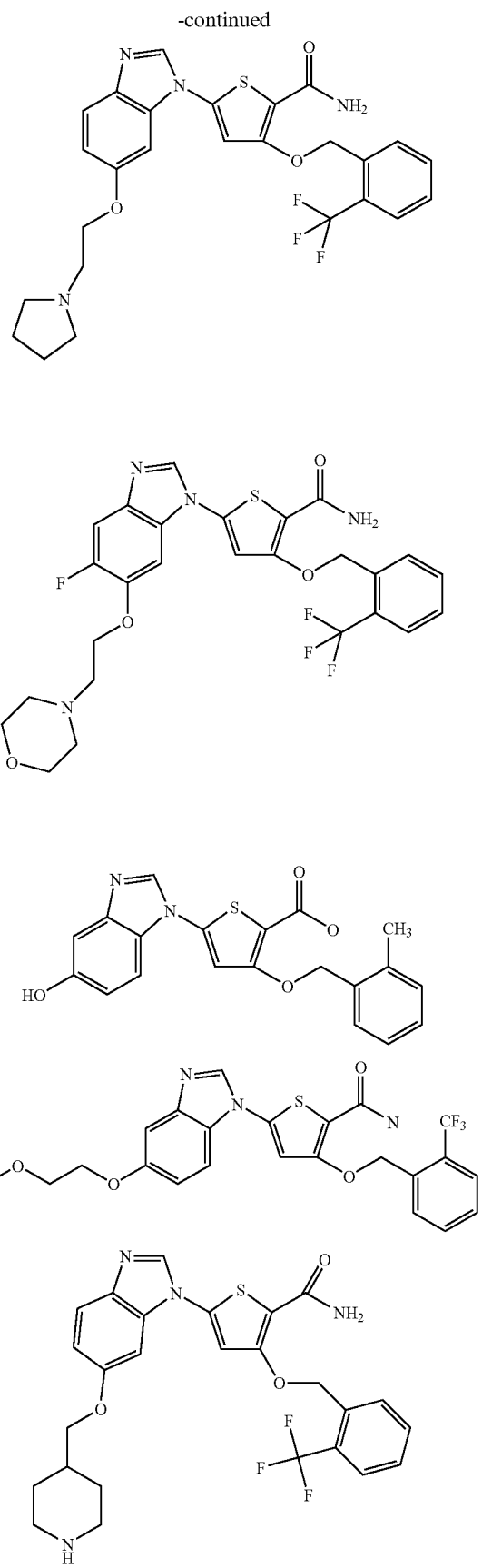

-continued
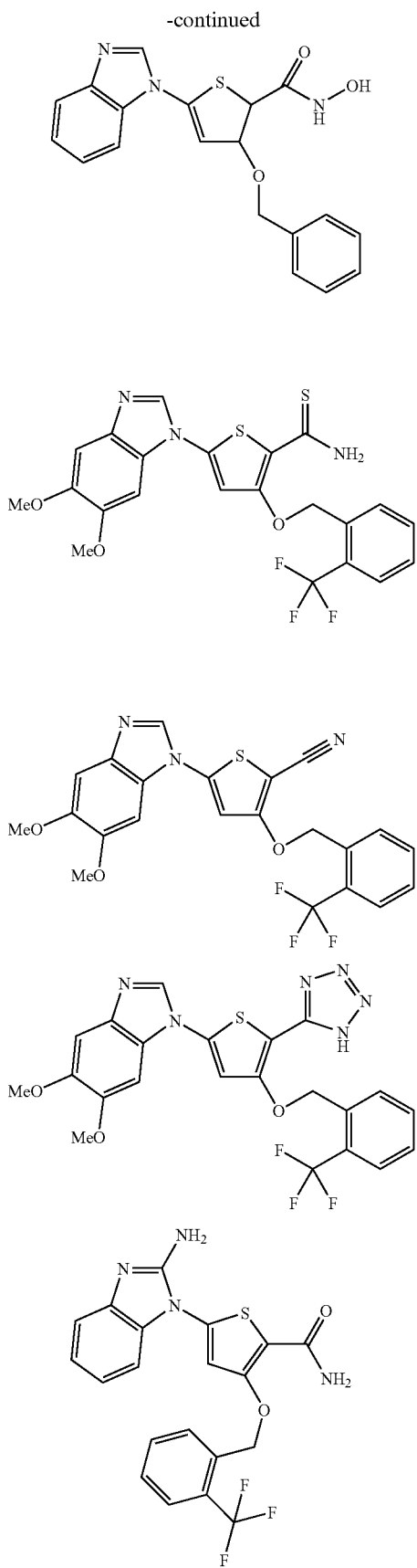
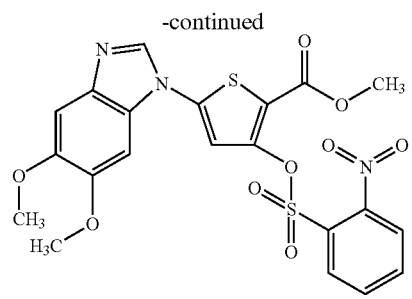
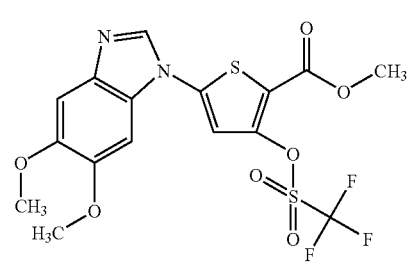
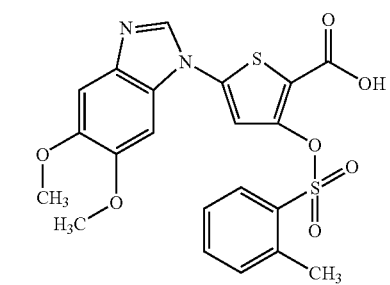
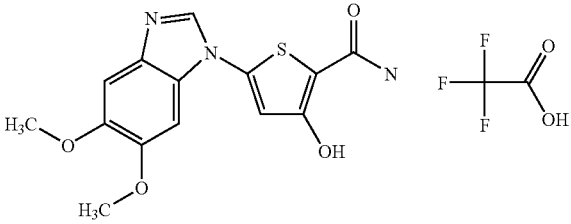
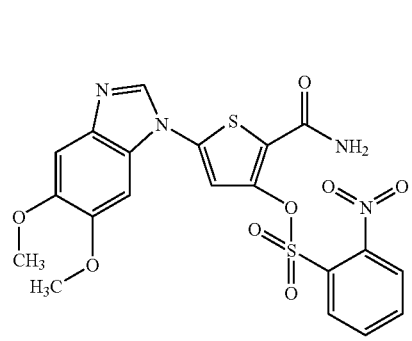

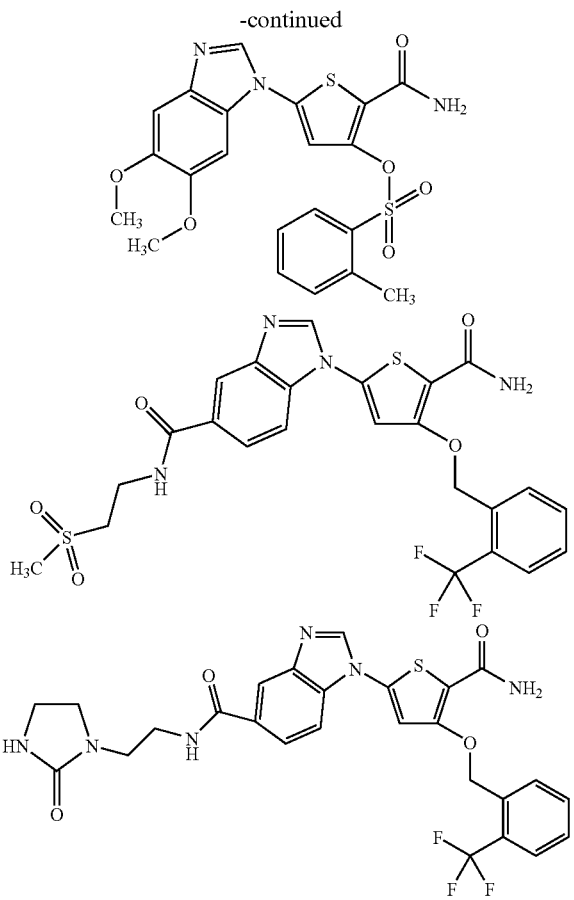

The invention claimed is:

1. A process for preparing a compound of formula (I):

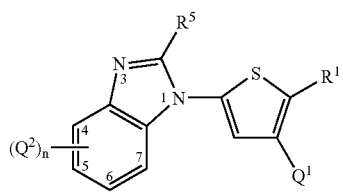

wherein:

R$^1$ is selected from the group consisting of H, alkyl, alkenyl, alkynyl, —C(O)R$^7$, —CO$_2$R$^7$, —C(O)NR$^7$R$^8$, —C(O)N(R$^7$)OR$^8$, —C(O)N(R$^7$)—R$^2$—OR$^8$, —C(O)N(R$^7$)-Ph, —C(O)N(R$^7$)—R$^2$-Ph, —C(O)N(R$^7$)C(O)R$^8$, —C(O)N(R$^7$)CO$_2$R$^8$, —C(O)N(R$^7$)C(O)NR$^7$R$^8$, —C(O)N(R$^7$)S(O)$_2$R$^8$, —R$^2$—OR$^7$, —R$^2$—O—C(O)R$^7$, —C(S)R$^7$, —C(S)NR$^7$R$^8$, —C(S)N(R$^7$)-Ph, —C(S)N(R$^7$)—R$^2$-Ph, —R$^2$—SR$^7$, —C(=NR$^7$)NR$^7$R$^8$, —C(=NR$^7$)N(R$^8$)-Ph, —C(=NR$^7$)N(R$^8$)—R$^2$-Ph, —R$^2$—NR$^7$R$^8$, —CN, —OR$^7$, —S(O)$_f$R$^7$, —S(O)$_2$NR$^7$R$^8$, —S(O)$_2$N(R$^7$)-Ph, —S(O)$_2$N(R$^7$)—R$^2$-Ph, —NR$^7$R$^8$, N(R$^7$)-Ph, —N(R$^7$)—R$^2$-Ph, —N(R$^7$)—SO$_2$R$^8$ and Het;

Ph is phenyl optionally substituted from 1 to 3 times with a substituent selected from the group consisting of halo, alkyl, —OH, —R$^2$—OH, —O-alkyl, —R$^2$—O-alkyl, —NH$_2$, —N(H)alkyl, —N(alkyl)$_2$, —CN and —N$_3$;

Het is a 5-7 membered heterocycle having 1, 2, 3 or 4 heteroatoms selected from N, O and S, or a 5-6 membered heteroaryl having 1, 2, 3 or 4 heteroatoms selected from N, O and S, each optionally substituted from 1 to 2 times with a substituent selected from the group consisting of halo, alkyl, oxo, —OH, —R$^2$—OH, —O-alkyl, —R$^2$—O-alkyl, —NH$_2$, —N(H)alkyl, —N(alkyl)$_2$, —CN and —N$_3$;

Q$^1$ is a group of formula: —(R$^2$)$_a$—(Y$^1$)$_b$—(R$^2$)$_c$—R$^3$ a, b and c are the same or different and are each independently 0 or 1 and at least one of a or b is 1;

n is 0, 1, 2, 3 or 4;

Q$^2$ is a group of formula: —(R$^2$)$_{aa}$—(Y$^2$)$_{bb}$—(R$^2$)$_{cc}$—R$^4$ or two adjacent Q$^2$ groups are selected from the group consisting of alkyl, alkenyl, —OR$^7$, —S(O)$_f$R$^7$ and —NR$^7$R$^8$ and together with the carbon atoms to which they are bound, they form a C$_{5-6}$cycloalkyl, C$_{5-6}$cycloalkenyl, phenyl, 5-7 membered heterocycle having 1 or 2 heteroatoms selected from N, O and S, or 5-6 membered heteroaryl having 1 or 2 heteroatoms selected from N, O and S;

aa, bb and cc are the same or different and are each independently 0 or 1;

each Y$^1$ and Y$^2$ is the same or different and is independently selected from the group consisting of —O—, —S(O)$_f$—, —N(R$^7$)—, —C(O)—, —OC(O)—, —CO$_2$—, —C(O)N(R$^7$)—, —C(O)N(R$^7$)S(O)$_2$—, —OC(O)N(R$^7$)—, —OS(O)$_2$—, —S(O)$_2$N(R$^7$)—, —S(O)$_2$N(R$^7$)C(O)—, —N(R$^7$)S(O)$_2$—, —N(R$^7$)C(O)—, —N(R$^7$)CO$_2$— and —N(R$^7$)C(O)N(R$^7$)—;

each R$^2$ is the same or different and is independently selected from the group consisting of alkylene, alkenylene and alkynylene;

each R$^3$ and R$^4$ is the same or different and is each independently selected from the group consisting of H, halo, alkyl, alkenyl, alkynyl, —C(O)R$^7$, —C(O)NR$^7$R$^8$, —CO$_2$R$^7$, —C(S)R$^7$, —C(S)NR$^7$R$^8$, —C(=NR$^7$)R$^8$, —C(=NR$^7$)NR$^7$R$^8$, —CR$^7$=N—OR$^7$, —OR$^7$, —S(O)$_f$R$^7$, —S(O)$_2$NR$^7$R$^8$, —NR$^7$R$^8$, —N(R$^7$)C(O)R$^8$, —N(R$^7$)S(O)$_2$R$^8$, —NO$_2$, —CN, —N$_3$ and a group of formula (ii):

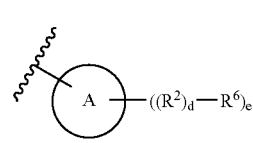

wherein:

Ring A is selected from the group consisting of C$_{5-10}$cycloalkyl, C$_{5-10}$cycloalkenyl, aryl, 5-10 membered heterocycle having 1, 2 or 3 heteroatoms selected from N, O and S and 5-10 membered heteroaryl having 1, 2 or 3 heteroatoms selected from N, O and S each d is 0 or 1;

e is 0, 1, 2, 3 or 4;

each R$^6$ is the same or different and is independently selected from the group consisting of H, halo, alkyl, alkenyl, alkynyl, cycloalkyl, cycloalkenyl, Ph, Het, —CH(OH)—R$^2$—OH, —C(O)R$^7$, —CO$_2$R$^7$, —CO$_2$—R$_2$-Ph, —CO$_2$—R$^2$-Het, —C(O)NR$^7$R$^8$, —C(O)N(R⁷)C(O)R⁷, —C(O)N(R⁷)CO₂R⁷, —C(O)N(R⁷)C(O)NR⁷R⁸, —C(O)N(R⁷)S(O)₂R⁷, —C(S)R⁷, —C(S)NR⁷R⁸, —C(=NR⁷)R⁸, —C(=NR⁷)NR⁷R⁸, —CR⁷=N—OR⁸, =O, —OR⁷, —OC(O)R⁷, —OC(O)Ph, —OC(O)Het, —OC(O)NR⁷R⁸, —O—R²—S(O)₂R⁷, —S(O)ᵣR⁷, —S(O)₂NR⁷R⁸, —S(O)₂Ph, —S(O)₂Het, —NR⁷R⁸, —N(R⁷)C(O)R⁸, —N(R⁷)CO₂R⁸, —N(R⁷)—R²—CO₂R⁸, —N(R⁷)C(O)NR⁷R⁸, —N(R⁷)—R²—C(O)NR⁷R⁸, —N(R⁷)C(O)Ph, —N(R⁷)C(O)Het, —N(R⁷)Ph, —N(R⁷)Het, —N(R⁷)C(O)NR⁷—R²—NR⁷R⁸, —N(R⁷)C(O)N(R⁷)Ph, —N(R⁷)C(O)N(R⁷)Het, —N(R⁷)C(O)N(R⁷)—R²-Het, —N(R⁷)S(O)₂R⁸, —N(R⁷)—R²—S(O)₂R⁸, —NO₂, —CN and —N₃;

wherein when Q¹ is defined where b is 1 and c is 0, R³ is not halo, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —S(O)ᵣR⁷, —S(O)₂NR⁷R⁸, —NR⁷R⁸, —N(R⁷)C(O)R⁸, —N(R⁷)S(O)₂R⁸, —NO₂, —CN or —N₃;

wherein when Q² is defined where bb is 1 and cc is 0, R⁴ is not halo, —C(O)R⁷, —C(O)NR⁷R⁸, —CO₂R⁷, —C(S)R⁷, —C(S)NR⁷R⁸, —C(=NR⁷)R⁸, —C(=NR⁷)NR⁷R⁸, —CR⁷=N—OR⁷, —OR⁷, —S(O)ᵣR⁷, —S(O)₂NR⁷R⁸, —NR⁷R⁸, —N(R⁷)C(O)R⁸, —N(R⁷)S(O)₂R⁸, —NO₂, —CN or —N₃;

R⁵ is selected from the group consisting of H, halo, alkyl, cycloalkyl, —OR⁷, —S(O)ᵣR⁷, —NR⁷R⁸, —NHC(O)R⁷, —NHC(O)NR⁷R⁸ and —NHS(O)₂R⁷;

f is 0, 1 or 2; and each R⁷ and each R⁸ are the same or different and are each independently selected from the group consisting of H, alkyl, alkenyl, alkynyl, cycloalkyl and cycloalkenyl;

or a pharmaceutically acceptable salt thereof;

said process comprising the steps of reacting one equivalent of a compound of formula (III):

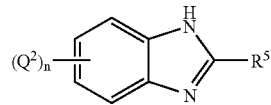

or an acid addition salt thereof,
with one equivalent of a compound of formula (IV):

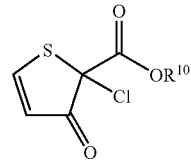

wherein R¹⁰ is selected from alkyl, alkenyl, alkynyl, cycloalkyl, cycloalkenyl and suitable carboxylic acid protecting groups;

in the presence of a base additive selected from sodium bicarbonate, triethylamine, sodium acetate, N-methylimidazole, pyridine and N-methylbenzimidazole.

2. The process according to claim 1, wherein said base additive is sodium bicarbonate.

3. The process according to claim 1, wherein said base additive is N-methylimidazole.

4. The process according to claim 1, wherein said reaction is carried out in an inert solvent.

5. The process according to claim 4, wherein said inert solvent is chloroform or a mixture of chloroform and acetic acid.

6. The process according to claim 1 further comprising the step of converting the compound of formula (I) to a pharmaceutically acceptable salt salt thereof.

7. The process according to claim 1 further comprising the step of converting the compound of formula (I) or a pharmaceutically acceptable salt or solvate thereof to a different compound of formula (I) or a pharmaceutically acceptable salt thereof.

* * * * *